United States Patent
Smith et al.

(10) Patent No.: US 11,629,150 B2
(45) Date of Patent: Apr. 18, 2023

(54) SYNTHESIS OF N-(HETEROARYL)-PYRROLO[3,2-D]PYRIMIDIN-2-AMINES

(71) Applicant: G1 Therapeutics, Inc., Research Triangle Park, NC (US)

(72) Inventors: Alexander Smith, Apex, NC (US); Hannah S. White, Chapel Hill, NC (US); Francis Xavier Tavares, Durham, NC (US); Sergiy Krasutsky, Delmar, NY (US); Jian-Xie Chen, Albany, NY (US); Roberta L. Dorrow, Kalamazoo, MI (US); Hua Zhong, Boston, MA (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 17/121,392

(22) Filed: Dec. 14, 2020

(65) Prior Publication Data
US 2021/0122755 A1    Apr. 29, 2021

Related U.S. Application Data

(60) Division of application No. 16/230,381, filed on Dec. 21, 2018, now Pat. No. 10,865,210, which is a continuation of application No. PCT/US2017/040102, filed on Jun. 29, 2017.

(60) Provisional application No. 62/357,797, filed on Jul. 1, 2016.

(51) Int. Cl.
| | | |
|---|---|---|
| *C07D 487/20* | (2006.01) | |
| *C07D 487/14* | (2006.01) | |
| *C07D 403/04* | (2006.01) | |
| *A61P 35/00* | (2006.01) | |

(52) U.S. Cl.
CPC ......... *C07D 487/20* (2013.01); *C07D 403/04* (2013.01); *C07D 487/14* (2013.01)

(58) Field of Classification Search
CPC ............... C07D 487/20; C07D 487/14; C07D 403/04; A61P 35/00; A61P 31/519
See application file for complete search history.

(56) References Cited

U.S. PATENT DOCUMENTS

| | | |
|---|---|---|
| 6,506,760 B1 | 1/2003 | Araldi et al. |
| 2005/0154000 A1 | 7/2005 | Jolidon et al. |
| 2006/0142312 A1 | 6/2006 | Flamme et al. |
| 2009/0264401 A1 | 10/2009 | Gill et al. |
| 2014/0271466 A1* | 9/2014 | Sharpless ............... A61P 35/00 514/233.2 |
| 2015/0031674 A1 | 1/2015 | Rudolph et al. |
| 2015/0297608 A1 | 10/2015 | Strum et al. |
| 2018/0208608 A1 | 7/2018 | Brodney, et al. |

FOREIGN PATENT DOCUMENTS

| | | |
|---|---|---|
| CN | 105622638 A | 6/2016 |
| WO | WO 2002/12238 A2 | 2/2002 |
| WO | WO 2004/047725 A2 | 6/2004 |
| WO | WO 2006/029153 A2 | 3/2006 |
| WO | WO 2006/031606 A2 | 3/2006 |
| WO | WO 2006/031610 A2 | 3/2006 |
| WO | WO 2007/061677 A2 | 5/2007 |
| WO | WO 2008/073251 A1 | 6/2008 |
| WO | WO 2008/109464 A1 | 9/2008 |
| WO | WO 2010/020675 A1 | 2/2010 |
| WO | WO 2013/148748 A1 | 10/2013 |
| WO | WO 2013/163239 A1 | 10/2013 |
| WO | WO 2013/169574 A2 | 11/2013 |
| WO | WO 2014168975 A1 | 10/2014 |
| WO | WO 2012/061156 A1 | 4/2015 |
| WO | WO 2015/061407 A1 | 4/2015 |

OTHER PUBLICATIONS

Reddy, M.V.R. et al., Discovery of 8-Cyclopentyl-2-[4-(4-methyl-piperazin-1-yl)-phenylamino]-7-oxo-7,8-dihydro-pyrido[2,3-d]pyrimidine-6-carbonitrile (7x) as a Potent Inhibitor of Cyclin-Dependent Kinase 4 (CDK4) and AMPK-Related Kinase 5 (ARK5), J. Med. Chem., 2014, vol. 57, pp. 578-599.
U.S. Pat. No. 8,598,186 B2, U.S. Appl. No. 13/869,520, Tavares et al., filed Dec. 3, 2013.
U.S. Pat. No. 8,598,197 B2, U.S. Appl. No. 13/869,576, Tavares et al., filed Dec. 3, 2013.
U.S. Pat. No. 8,691,830 B2, U.S. Appl. No. 13/869,594, Tavares et al., filed Apr. 8, 2014.
U.S. Pat. No. 8,822,683 B2, U.S. Appl. No. 14/162,637, Tavares et al., filed Sep. 2, 2014.
U.S. Pat. No. 8,829,012 B2, U.S. Appl. No. 14/162,649, Tavares et al., filed Sep. 9, 2014.
U.S. Pat. No. 9,102,682 B2, U.S. Appl. No. 14/452,296, Tavares et al., filed Aug. 11, 2015.
U.S. Pat. No. 9,260,442 B2, U.S. Appl. No. 14/498,796, Tavares, filed Jan. 27, 2016.
U.S. Pat. No. 9,464,092 B2, U.S. Appl. No. 14/212,911, Strum et al., filed Oct. 11, 2016.
U.S. Pat. No. 9,481,691 B2, U.S. Appl. No. 14/712,630, Tavares et al., filed Nov. 1, 2016.
U.S. Pat. No. 9,487,530 B2, U.S. Appl. No. 14/212,430, Strum et al., filed Nov. 8, 2016.
U.S. Pat. No. 9,499,564 B2, U.S. Appl. No. 14/712,582, Tavares et al., filed Nov. 22, 2016.
U.S. Pat. No. 9,527,857 B2, U.S. Appl. No. 14/214,048, Strum et al., filed Dec. 27, 2016.
U.S. Pat. No. 9,717,735 B2, U.S. Appl. No. 14/690,180, Strum et al., filed Aug. 1, 2017.
U.S. Pat. No. 9,745,316 B2, U.S. Appl. No. 14/982,443, Tavares, filed Aug. 29, 2017.
U.S. Pat. No. 9,856,268 B2, U.S. Appl. No. 15/348,862, Tavares, filed Jan. 2, 2018.

(Continued)

*Primary Examiner* — Sun Jae Yoo
(74) *Attorney, Agent, or Firm* — Knowles Intellectual Property Strategies, LLC

(57) ABSTRACT

This invention is in the area of synthesizing pyrimidine-based compounds useful in the treatment of disorders involving abnormal cellular proliferation, including but not limited to tumors and cancers.

5 Claims, 4 Drawing Sheets

(56) References Cited

OTHER PUBLICATIONS

U.S. Pat. No. 9,931,345 B2, U.S. Appl. No. 15/288,878, Strum et al., filed Apr. 3, 2018.
U.S. Pat. No. 9,957,276 B2, U.S. Appl. No. 15/348,770, Tavares et al., filed May 1, 2018.
U.S. Pat. No. 10,076,523 B2, U.S. Appl. No. 15/387,083, Strum et al., filed Sep. 18, 2018.
U.S. Pat. No. 10,085,992 B2, U.S. Appl. No. 15/342,990, Strum et al., filed Oct. 2, 2018.
U.S. Pat. No. 10,189,849 B2, U.S. Appl. No. 15/918,834, Tavares et al., filed Jan. 29, 2019.
U.S. Pat. No. 10,189,850 B2, U.S. Appl. No. 15/918,852, Tavares et al., filed Jan. 29, 2019.
U.S. Pat. No. 10,189,851 B2, U.S. Appl. No. 15/918,877, Tavares et al., filed Jan. 29, 2019.
U.S. Pat. No. 10,231,969 B2, U.S. Appl. No. 15/457,699, Strum, et al., filed Mar. 19, 2019.
U.S. Pat. No. 10,376,519 B2, U.S. Appl. No. 15/665,071, Strum, et al., filed Aug. 13, 2019.
U.S. Pat. No. 10,413,547 B2, U.S. Appl. No. 16/142,574, Strum, et al., filed Sep. 17, 2019.
U.S. Pat. No. 10,434,104 B2, U.S. Appl. No. 16/112,362, Strum, et al., filed Oct. 8, 2019.
U.S. Pat. No. 10,464,940 B2, U.S. Appl. No. 15/860,483, Tavares et al., filed Nov. 5, 2019.
U.S. Pat. No. 10,618,905 B2, U.S. Appl. No. 16/230,412, Strum, et al., filed Apr. 14, 2020.
U.S. Pat. No. 10,654,831 B2, U.S. Appl. No. 16/230,388, Strum, et al., filed May 19, 2020.
U.S. Pat. No. 10,660,896 B2, U.S. Appl. No. 15/943,278, Strum, et al., filed May 26, 2020.
U.S. Pat. No. 10,696,682 B2, U.S. Appl. No. 16/226,430, Tavares et al., filed Jun. 30, 2020.
U.S. Pat. No. 10,709,711 B2, U.S. Appl. No. 16/228,308, Strum, et al., filed Jul. 14, 2020.
U.S. Pat. No. 10,829,490 B2, U.S. Appl. No. 16/230,396, Strum, et al., filed Nov. 10, 2020.
U.S. Pat. No. 10,865,210 B2, U.S. Appl. No. 16/230,381, Smith et al., filed Dec. 15, 2020.
US 2018/0360840 A1, U.S. Appl. No. 16/112,360, Strum, et al., filed Dec. 20, 2018.
US 2019/0070185 A1, U.S. Appl. No. 16/178,419, Strum, et al., filed Mar. 7, 2019.
US 2019/0151311 A1, U.S. Appl. No. 16/254,364, Strum, et al., filed May 23, 2019.
US 2019/0321370 A1, U.S. Appl. No. 16/432,244, Sorrentino, et al., filed Oct. 24, 2019.
US 2019/0321332 A1, U.S. Appl. No. 16/460,502, Strum, filed Oct. 24, 2019.
US 2019/0374545 A1, U.S. Appl. No. 16/547,342, Sorrentino, et al., filed Dec. 12, 2019.
US 2020/0022983 A1, U.S. Appl. No. 16/572,418, Strum, et al., filed Jan. 23, 2020.
US 2020/0123168 A1, U.S. Appl. No. 16/721,631, Smith et al., filed Apr. 23, 2020.
US 2020/0239486 A1, U.S. Appl. No. 16/572,418, Strum, et al., filed Jan. 23, 2020.
US 2020/0283406 A1, U.S. Appl. No. 16/572,418, Strum, et al., filed Jan. 23, 2020.
US 2020/0331925 A1, U.S. Appl. No. 16/721,631, Smith et al., filed Apr. 23, 2020.
US 2020/0345742 A1, U.S. Appl. No. 16/572,418, Strum, et al., filed Jan. 23, 2020.
US 2020/0345743 A1, U.S. Appl. No. 16/721,631, Smith et al., filed Apr. 23, 2020.
US 2020/0405721 A1, U.S. Appl. No. 16/924,033, Beelen et al., filed Dec. 31, 2020.
U.S. Appl. No. 17/067,549, Strum, et al., filed Oct. 9, 2020.
U.S. Appl. No. 17/088,298, Strum, et al., filed Nov. 3, 2020.
U.S. Appl. No. 17/097,854, Schneider, et al., filed Nov. 13, 2020.
U.S. Appl. No. 17/102,311, Strum, et al., filed Nov. 23, 2020.
U.S. Pat. No. 10,208,011 B2, U.S. Appl. No. 15/893,295, Strum et al., filed Feb. 19, 2019.
U.S. Pat. No. 10,633,362 B2, U.S. Appl. No. 16/221,201, Strum et al., filed Apr. 28, 2020.
U.S. Pat. No. 10,927,120 B2, U.S. Appl. No. 15/931,330, Tavares et al., filed Feb. 23, 2021.
U.S. Pat. No. 10,966,984 B2, U.S. Appl. No. 16/112,360, Strum et al., filed Apr. 6, 2021.
U.S. Pat. No. 10,988,479 B1, U.S. Appl. No. 17/097,854, Schneider et al., filed Apr. 27, 2021.
US 2020/0345742 A1, U.S. Appl. No. 16/886,309, Strum et al., filed Jun. 22, 2021.
US 2019/0167691 A1, U.S. Appl. No. 16/268,317, Strum et al., filed Jun. 6, 2019.
US 2020/0239486 A1, U.S. Appl. No. 16/847,426, Strum et al., filed Jul. 30, 2020.
US 2021/0030758 A1, U.S. Appl. No. 17/067,549, Strum et al., filed Feb. 4, 2021.
US 2021/0047328 A1, U.S. Appl. No. 17/088,298, Strum et al., filed Feb. 18, 2021.
US 2021/0077498 A1, U.S. Appl. No. 17/102,311, Strum et al., filed Mar. 18, 2021.
U.S. Appl. No. 17/153,516, Tavares et al., filed Jan. 20, 2021.
U.S. Appl. No. 17/181,638, Strum et al., filed Feb. 22, 2021.
U.S. Appl. No. 17/184,354, Schneider et. al., filed Feb. 24, 2021.
U.S. Appl. No. 17/222,873, Strum et al., filed Apr. 5, 2021.
U.S. Appl. No. 17/234,686, Strum et al., filed Apr. 19, 2021.
U.S. Appl. No. 17/236,687, Schneider et. al., filed May 7, 2021.
U.S. Appl. No. 17/315,011, Sorrentino et al., filed May 7, 2021.
Duan et al., "Palbociclib Commercial Manufacturing Process Development. Part 1: Control of Regioselectivity in a Grignard-Mediated SnAr Coupling" OPR&D, DOI:10.1021/acs.oprd.6b00070.
Eary et al., "Tetrazole and ester substituted tetrahydroquinoxalines as potent cholesteryl ester transfer protein inhibitors," Bioorganic & Medicinal Chemistry Letters, 2007, vol. 17, pp. 2608-2613.
Fabris et al. "Methylcarbonate and Bicarbonate Phosphonium Salts as Catalysts for the Nitroaldol (Henry) Reaction", Journal of Organic Chemistry, 2012, vol. 77, pp. 1805-1811.
Griffith et al., "Spirolactam-Based Acetyl-CoA Carboxylase Inhibitors: Toward Improved Metabolic Stability of a Chromanone Lead Structure" Journal of Medicinal Chemistry 56(17): 7110-7119; 2013.
Kotsuki et al., "An Efficient Procedure for PalladiumCatalyzed Reduction of Aryl/Enoi Triflates," Synthesis 1995, vol. 11, pp. 1348-1350.
International Search Report and Written Opinion of PCT/US17/40102 dated Sep. 29, 2017.
International Search Report and Written Opinion of PCT/US2013/037878 dated Aug. 8, 2013.
Ono, N. "The Nitro-Aldol (Henry) Reaction", The Nitro Group in Organic Synthesis, 2001, pp. 30-69. p. 31, Scheme 3.1; p. 34, Table 3.1; p. 35.
Rajak, H. et al., "2,5-Disubstituted-1, 3, 4-oxadiazoles/thiadiazole as surface recognition moiety: Design and synthesis of novel hydroxamic acid based histone deacetylase inhibitors", Bioorganic & Medicinal Chemistry Letters, Pergamon, Amsterdam, NL, vol. 21, No. 19, Aug. 3, 2011, pp. 5735-5738, XP028286354, ISSN: 0960-894X, DOI: 10.1016/J.BNMCL.2011.09.022.
US 2021/0395259, U.S. Appl. No. 17/153,516, Tavares et al., filed Dec. 23, 2021.
US 2021/0213022, U.S. Appl. No. 17/181,638, Strum et al., filed Jul. 15, 2021.
US 2021/0179567, U.S. Appl. No. 17/184,354, Schneider et. al., filed Jun. 17, 2021.
US 2021/0299130, U.S. Appl. No. 17/222,873, Strum et al., filed Sep. 30, 2021.
US 2021/0387993, U.S. Appl. No. 17/236,687, Schneider et. al., filed Dec. 16, 2021.
US 2021/0267986, U.S. Appl. No. 17/315,011, Sorrentino et al., filed Sep. 2, 2021.

(56) References Cited

OTHER PUBLICATIONS

Rajak, Harish, et al; "2,5-Disubstituted-1,3,4-oxadiazoles/thiadiazole as surface recognition moiety: Design and synthesis of novel hydroxamic acid based histone deacetylase inhibitors," Bioorganic & Medicinal Chemistry Letters, vol. 21, Issue 19; pp. 5735-5738; Supplementary Material; 2011.

\* cited by examiner

SYNTHESIS OF N-(HETEROARYL)-PYRROLO[3,2-D]PYRIMIDIN-2-AMINES

CROSS-REFERENCE TO RELATED APPLICATIONS

This application is a divisional of U.S. patent application Ser. No. 16/230,381, filed Dec. 21, 2018, which is a continuation of International Application No. PCT/US2017/040102, filed with the International Patent Cooperation Treaty, U.S. Receiving Office on Jun. 29, 2017, which claims the benefit of U.S. Provisional Application 62/357,797 which was filed on Jul. 1, 2016. The entirety of these applications are hereby incorporated by reference herein for all purposes.

FIELD OF THE INVENTION

This invention is in the area of synthesizing pyrimidine-based compounds useful in the treatment of disorders involving abnormal cellular proliferation, including but not limited to tumors and cancers.

BACKGROUND

U.S. Pat. Nos. 8,822,683; 8,598,197; 8,598,186, 8,691,830, 8,829,102, 8,822,683, 9,102,682, 9,499,564, 9,481,591, and 9,260,442, filed by Tavares and Strum and assigned to G1 Therapeutics describe a class of N-(heteroaryl)-pyrrolo[3,2-d]pyrimidin-2-amine cyclin dependent kinase inhibitors including those of the formula (with variables as defined therein):

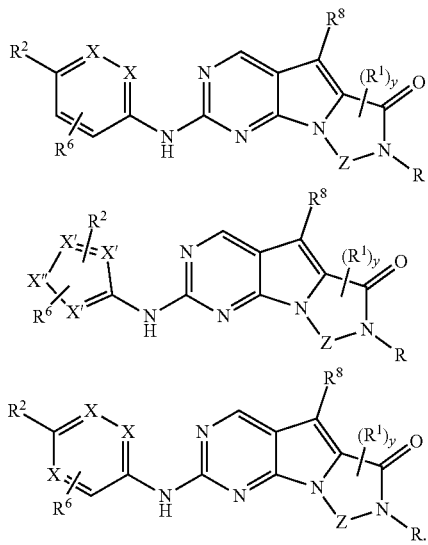

U.S. Pat. Nos. 9,464,092, 9,487,530, and 9,527,857 which are also assigned to G1 Therapeutics describe the use of the above pyrimidine-based agents in the treatment of cancer.

These patents provide a general synthesis of the compounds that is based on a coupling reaction of a fused chloropyrimidine with a heteroaryl amine to form the central disubstituted amine. Such coupling reactions are sometimes referred to as Buchwald coupling (see WO '156 paragraph 127; reference WO 2010/020675). The lactam of the fused chloropyrimidine, for example, a 2-chloro-spirocyclo-pyrrolo[2,3-d]pyrimidine-one such as Intermediate K as shown below can be prepared by dehydration of the corresponding carboxylic acid. The reported process to prepare intermediate 1K requires seven steps.

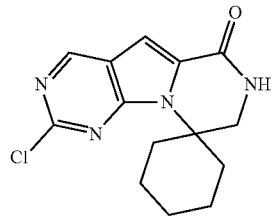 [SMILES: O=C1NCC2(CCCCC2)n2c1cc1cnc(Cl)nc12]

(Intermediate 1K; page 60, paragraph 215 of WO '156)

WO 2013/148748 (U.S. Ser. No. 61/617,657) entitled "Lactam Kinase Inhibitors" filed by Tavares, and also assigned to G1 Therapeutics likewise describes the synthesis of N-(heteroaryl)-pyrrolo[3,2-d]pyrimidin-2-amines via the coupling reaction of a fused chloropyrimidine with a heteroaryl amine to form the central disubstituted amine.

WO 2013/163239 (U.S. Ser. No. 61/638,491) "Synthesis of Lactams" describes a method for the synthesis of this class of compounds with the variation that in the lactam preparation step, a carboxylic acid can be cyclized with a protected amine in the presence of a strong acid and a dehydrating agent, which can be together in one moiety as a strong acid anhydride. The purported improvement is that cyclization can occur without losing the protecting group on the amine before cyclization. The typical leaving group is "tBOC" (t-butoxycarbonyl). The application teaches (page 2 of WO 2013/163239) that the strong acid is, for example, trifluoroacetic acid anhydride, tribromoacetic acid anhydride, trichloroacetic acid anhydride or mixed anhydrides. An additional step may be necessary to take off the N-protecting group. The dehydrating agent can be a carbodiimide-based compound such as DCC (N,N-dicyclohexylcarbodiimide), EDC (1-ethyl-3-(3-dimethylaminopropyl) carbodiimide, or DIC (N,N-diisopropylcarbodiimide). DCC and DIC are in the same class of reagents-carbodiimides. DIC is sometimes considered better because it is a liquid at room temperature, which facilitates reactions.

WO 2015/061407 filed by Tavares and licensed to G1 Therapeutics also describes the synthesis of these compounds via the coupling of a fused chloropyrimidine with a heteroaryl amine to form the central disubstituted amine. WO '407 focuses on the lactam production step and in particular describes that the fused lactams of these compounds can be prepared by treating the carboxylic acid with an acid and a dehydrating agent in a manner that a leaving group on the amine is not removed during the amide-forming ring closing step.

Other publications that describe compounds of this general class include the following. WO 2014/144326 filed by Strum et al. and assigned to G1 Therapeutics describes compounds and methods for protection of normal cells during chemotherapy using pyrimidine based CDK4/6 inhibitors. WO 2014/144596 filed by Strum et al. and assigned to G1 Therapeutics describes compounds and methods for protection of hematopoietic stem and progenitor cells against ionizing radiation using pyrimidine based CDK4/6 inhibitors. WO 2014/144847 filed by Strum et al. and assigned to G1 Therapeutics describes HSPC-sparing treatments of abnormal cellular proliferation using pyrimidine based CDK4/6 inhibitors. WO2014/144740 filed by Strum et al. and assigned to G1 Therapeutics describes highly active anti-neoplastic and anti-proliferative pyrimidine based CDK 4/6 inhibitors. WO 2015/161285 filed by Strum et al. and assigned to G1 Therapeutics describes tricyclic pyrimidine based CDK inhibitors for use in radioprotection. WO 2015/161287 filed by Strum et al. and assigned to G1 Therapeutics describes analogous tricyclic pyrimidine based CDK inhibitors for the protection of cells during chemotherapy. WO 2015/161283 filed by Strum et al. and assigned to G1 Therapeutics describes analogous tricyclic pyrimidine based CDK inhibitors for use in HSPC-sparing treatments of RB-positive abnormal cellular proliferation. WO 2015/161288 filed by Strum et al. and assigned to G1 Therapeutics describes analogous tricyclic pyrimidine based CDK inhibitors for use as anti-neoplastic and anti-proliferative agents. WO 2016/040858 filed by Strum et al. and assigned to G1 Therapeutics describes the use of combinations of pyrimidine based CDK4/6 inhibitors with other anti-neoplastic agents. WO 2016/040848 filed by Strum et al. and assigned to G1 Therapeutics describes compounds and methods for treating certain Rb-negative cancers with CDK4/6 inhibitors and topoisomerase inhibitors.

Other biologically active fused spirolactams and their syntheses are described, for example, in the following publications. Griffith, D. A., et al. (2013). "Spirolactam-Based Acetyl-CoA Carboxylase Inhibitors: Toward Improved Metabolic Stability of a Chromanone Lead Structure." Journal of Medicinal Chemistry 56(17): 7110-7119, describes metabolically stable spirolactams wherein the lactam resides on the fused ring for the inhibition of acetyl-CoA carboxylase. WO 2013/169574 filed by Bell et al. describes aliphatic spirolactams as CGRP receptor antagonists wherein the lactam resides on the spiro ring. WO 2007/061677 filed by Bell et al. describes aryl spirolactams as CGRP receptor antagonists wherein the lactam resides on the spiro ring. WO 2008/073251 filed by Bell et al. describes constrained spirolactam compounds wherein the lactam resides on the spiro ring as CGRP receptor antagonists. WO 2006/031606 filed by Bell et al. describes carboxamide spirolactam compounds wherein the spirolactam resides on the spiro ring as CGRP receptor antagonists. WO 2006/031610, WO 2006/031491, and WO 2006/029153 filed by Bell et al. describe anilide spirolactam compounds wherein the spirolactam resides on the spiro ring; WO 2008/109464 filed by Bhunai et al. describes spirolactam compounds wherein the lactam resides on the spiro ring which is optionally further fused.

Given the therapeutic activity of selected N-(heteroaryl)-pyrrolo[3,2-d]pyrimidin-2-amines, it would be useful to have additional methods for their preparation. It would also be useful to have new intermediates that can be used to prepare this class of compounds.

SUMMARY

It has been discovered that 2'-(heteroaryl)-lactam-pyrrolo[3,2-d]pyrimidines are advantageously prepared by coupling an alkyl sulfone or alkyl sulfoxide substituted fused pyrimidine with a heteroaryl amine to form the central disubstituted amine in yields above about 50%. In one embodiment the reaction is conducted at a temperature at or below about 20, 18, 16, 14, 12, or 10° C. In another embodiment the ratio of amine to sulfone is at least about 2 to 1. In another embodiment the ratio of amine to sulfone is at least about 3 to 1. Using an alkyl sulfone or alkyl sulfoxide substituted fused pyrimidine instead of a chloro substituted fused pyrimidine increases the yield of the coupled diamine product.

In another aspect of the invention, a new process is provided for the preparation of a 2'-(alkylsulfonyl or alkylsulfinyl)-pyrrolo[2,3-d]pyrimidines that can be used in the coupling reaction with the heteroaryl amine. As one illustrative example, the invention provides the 2'-(alkylsulfonyl or alkylsulfinyl)-pyrrolo[2,3-d]pyrimidine is of the following structure:

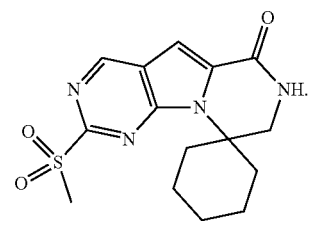 [SMILES: CS(=O)(=O)c1ncc2cc3n(c2n1)C1(CCCCC1)CNC3=O]

According to the invention, the 2'-(alkylsulfonyl or alkylsulfinyl)-pyrrolo[2,3-d]pyrimidine is prepared using either an ester or an aldehyde starting material. For example, the ester may be an alkyl 4-chloro-2-(alkylthio)pyrimidine-5-carboxylate, such as ethyl 4-chloro-2-(methylthio)pyrimidine-5-carboxylate. The aldehyde may be a 4-chloro-2-(alkylthio)pyrimidine-5-carbaldehyde, such as 4-chloro-2-(methylthio)pyrimidine-5-carbaldehyde. The reaction from the ester to the key intermediate 2'-(alkylsulfonyl or alkylsulfinyl)-pyrrolo[2,3-d]pyrimidine typically takes seven steps (some of which can be telescoped without compound isolation), each of which typically provide yields of greater than 50%. Each step is described in detail below.

The process for the preparation of the 2'-(alkylsulfonyl or alkylsulfinyl)-pyrrolo[2,3-d]pyrimidine is a facile and efficient route that consists of seven steps with only five isolations, all by crystallization. No column chromatography is required, which allows the process to be scalable for large manufacturing batches. Further, the process work-up conditions can successfully purge the majority of the palladium after Step 5. The level of residual palladium observed is below the ppm residual threshold for heavy metal content.

In addition, the invention includes new intermediates of Formula II that can be used in the process of preparing lactam-pyrrolo[2,3-d]pyrimidines of Formula IV. In another aspect of the invention, the synthesis of compounds of Formula I, Formula II, Formula III, and Formula IV is provided. In one non-limiting embodiment, compounds of Formula I, Formula II, and Formula III are synthetic precursors to Formula IV:

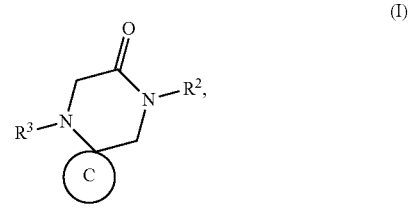

-continued

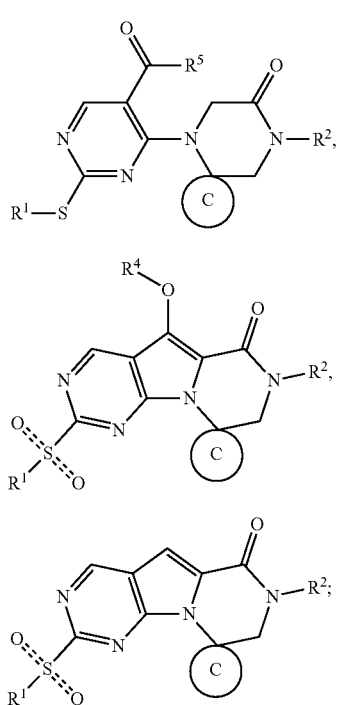

wherein:

╌╌╌╌╌ represents the presence or absence of a double bond;

represents a carbocycle of 3 to 8 carbons (including independently 3, 4, 5, 6, and 7 carbons, and in particular where the

is cyclohexyl) connected in a spiro-fashion to the lactam ring wherein the spirocycle is optionally substituted;

$R^1$ is selected from: alkyl, aryl, haloalkyl, and arylalkyl;

$R^2$ and $R^3$ are independently selected from hydrogen, carbamate, aryl, alkyl, allyl, and arylalkyl;

$R^4$ is selected from: hydrogen, silyl, haloalkyl, —C(O) alkyl, —S(O)$_2$alkyl, —S(O)$_2$haloalkyl, —S(O)$_2$aryl, and —S(O)$_2$arylalkyl; and $R^5$ is selected from: hydrogen, halogen, —N(alkyl) (alkoxy), —NCH$_3$OMe, alkoxy, aryloxy, —OCH$_2$aryl, —OC(O)alkyl, —OC(O)aryl, and —OC(O)arylalkyl.

In one embodiment, the heteroaryl amine is dissolved in a polar solvent, and the alkyl sulfone or alkyl sulfoxide is added portion-wise at temperatures at or below about 20, 18, 16, 14, 12, or 10° C., wherein, a ratio of amine to sulfone of at least about 2 to 1 and a ratio of base to sulfone of at least 2 to 1 is used to afford the central disubstituted amine in yields above about 50%.

In another embodiment, the heteroaryl amine is dissolved in a polar solvent, and the alkyl sulfone or alkyl sulfoxide is added portion-wise wherein, a ratio of amine to sulfone of at least about 2 to 1 and a ratio of base to sulfone of at least 2 to 1 is used to afford the central disubstituted amine in yields above about 50%.

In one embodiment, the heteroaryl amine is dissolved in a polar solvent, and the alkyl sulfone or alkyl sulfoxide is added portion-wise at temperatures at or below about 20, 18, 16, 14, 12, or 10° C., wherein, a ratio of amine to sulfone of at least about 3 to 1 and a ratio of base to sulfone of at least 2 to 1 is used to afford the central disubstituted amine in yields above about 50%.

In another embodiment, the heteroaryl amine is dissolved in a polar solvent, and the alkyl sulfone or alkyl sulfoxide is added portion-wise at temperatures at or below about 20, 18, 16, 14, 12, or 10° C., wherein, a ratio of amine to sulfone of at least about 3 to 1 and a ratio of base to sulfone of at least 3 to 1 is used. After complete addition the reaction mixture is quenched with ammonium chloride to recover the central disubstituted amine in yields above about 50%.

In one embodiment, after the reaction is complete the reaction mixture is quenched with ammonium chloride to recover the central disubstituted amine in yields above about 50%.

In one embodiment, the base is LiHMDS.

In one non-limiting embodiment, a 2'-(alkylsulfonyl or alkylsulfinyl)-lactam-pyrrolo[2,3-d]pyrimidine is prepared from an ester starting material and includes the following steps:

(i) nucleophilic attack of a compound of Formula V by a lactam amine to afford an alkyl 2-(alkylthio)-4-(lactam) pyrimidine-5-carboxylate;

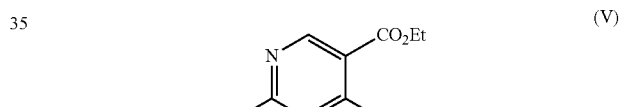

(ii) optional protection of the alkyl 2-(alkylthio)-4-(lactam)pyrimidine-5-carboxylate;
(iii) cyclization of the alkyl 2-(alkylthio)-4-(lactam)pyrimidine-5-carboxylate to afford a 5'-hydroxy-2'-(alkylthio)-lactam-pyrrolo[2,3-d]pyrimidine;
(iv) conversion of the hydroxy group of 5'-hydroxy-2'-(alkylthio)-lactam-pyrrolo[2,3-d]pyrimidine to a leaving group;
(v) dehydration of the compound produced in (iv) to afford a 2'-(alkylthio)-lactam-pyrrolo[2,3-d]pyrimidine;
(vi) optional deprotection of the 2'-(alkylthio)-lactam-pyrrolo[2,3-d]pyrimidine; and then
(vii) optional oxidation of the mercapto group of the 2'-(alkylthio)-lactam-pyrrolo[2,3-d]pyrimidine.

In an alternative embodiment, the oxidation, protection or deprotection above are reordered or removed as allowed by the reagents and substrates being used. For example, if the lactam amine of step (i) above is already protected then step (ii) is omitted.

In another embodiment, step (vi) and step (vii) are switched.

In one non-limiting embodiment, the process to synthesize a compound of Formula IV includes the following steps:
(i) nucleophilic attack of a compound of Formula V by a compound of Formula I to afford a compound of Formula II;

(ii) optional protection of the compound of Formula II;
(iii) cyclization of a compound of Formula II to afford a compound of Formula III wherein $R^4$ is H;
(iv) substitution of the hydrogen $R^4$ with a group other than hydrogen that facilitates the subsequent dehydration;
(v) dehydration of a compound of Formula III to afford a compound of Formula IV;
(vi) optional deprotection of the compound of Formula IV; and then
(vii) optional oxidation of the mercapto group of Formula IV to a sulfone.

In another embodiment, the process to synthesize a compound of Formula IV includes the following steps:
(i) cyclization of a compound of Formula II to afford a compound of Formula III wherein $R^4$ is H;
(ii) substitution of the hydrogen $R^4$ with a group other than hydrogen that facilitates the subsequent dehydration;
(iii) dehydration of a compound of Formula III to afford a compound of Formula IV;
(iv) optional deprotection of the compound of Formula IV; and
(v) optional oxidation of the mercapto group of Formula IV to a sulfone.

In another embodiment, the process to synthesize a compound of Formula IV includes the following steps:
(i) dehydration of a compound of Formula III to afford a compound of Formula IV;
(ii) optional deprotection of the compound of Formula IV; and then
(iii) optional oxidation of the mercapto group of Formula IV to a sulfone.

In one non-limiting embodiment, the process to synthesize a 2'-(alkylsulfonyl or alkylsulfinyl)-lactam-pyrrolo[2,3-d]pyrimidine from an aldehyde starting material includes the following steps:
(i) nucleophilic attack of a compound of Formula VI by a lactam amine to afford an alkyl 2-(alkylthio)-4-(lactam)pyrimidine-5-carboxylate;

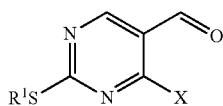

(VI)

(ii) optional protection of the alkyl 2-(alkylthio)-4-(lactam)pyrimidine-5-carboxylate;
(iii) cyclization of the alkyl 2-(alkylthio)-4-(lactam)pyrimidine-5-carboxylate to afford a 2'-(alkylthio)-lactam-pyrrolo[2,3-d]pyrimidine;
(iv) optional deprotection of the 2'-(alkylthio)-lactam-pyrrolo[2,3-d]pyrimidine; and then
(v) optional oxidation of the mercapto group of the 2'-(alkylthio)-lactam-pyrrolo[2,3-d]pyrimidine.

In an alternative embodiment, the oxidation, protection, or deprotection above are reordered or removed as allowed by the reagents and substrates being used. For example, if the lactam amine of step (i) above is already protected then step (ii) is omitted.

In another embodiment, step (iv) and step (v) are switched.

In an alternative embodiment, the process to synthesize a compound of Formula IV includes the following steps:
(i) nucleophilic attack of a compound of Formula VI by a compound of Formula I to afford a compound of Formula II;
(ii) optional protection of the compound of Formula II;
(iii) cyclization of a compound of Formula II to afford a compound of Formula IV;
(iv) optional deprotection of the compound of Formula IV; and
(v) optional oxidation of the mercapto group of Formula IV to a sulfone.

In one non-limiting embodiment, the process to synthesize a compound of Formula III includes the following steps:
(i) nucleophilic attack of a compound of Formula V by a compound of Formula I to afford a compound of Formula II;
(ii) optional protection of a compound of Formula II;
(iii) cyclization of a compound of Formula II to afford a compound of Formula III wherein $R^4$ is H;
(iv) optional substitution of the hydrogen $R^4$ with a group other than hydrogen that facilitates the subsequent dehydration; and then
(v) optional oxidation of the mercapto group of Formula III to a sulfone.

In one non-limiting embodiment, the process to synthesize a compound of Formula II includes the following steps:
(i) nucleophilic attack of a compound of Formula V by a compound of Formula I; and then
(ii) isolation of a compound of Formula II.

In an alternative embodiment, the process to synthesize a compound of Formula II includes the following steps:
(i) nucleophilic attack of a compound of Formula VI by a compound of Formula I; and then
(ii) isolation of a compound of Formula II.

In an alternative embodiment, the process to synthesize a compound of Formula I includes the following steps:
(i) reductive amination of an amine of Formula VII with alkyl 2-oxoacetate to afford a compound of Formula VIII;
(ii) optional deprotection of a compound of Formula VIII;
(iii) optional addition of a base; and then
(iv) isolation of a compound of Formula I.

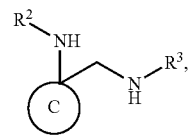

(VII)

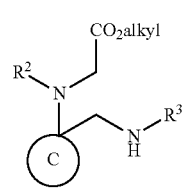

(VIII)

In another alternative embodiment, the process to synthesize a compound of Formula I includes the following steps:
(i) condensation of an alkyl glycinate with cyclohexanone in the presence of TMSCN to afford a compound of Formula IX;
(ii) reduction of the cyano compound to an amine followed by subsequent intramolecular cyclization; and then (iii) isolation of a compound of Formula I.

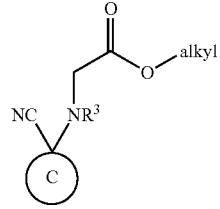

(IX)

In one non-limiting example of the present invention the coupling of a sulfone with a heteroaryl amine produces a compound of Formula X:

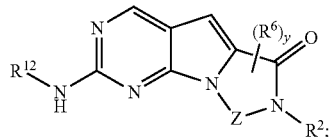

(X)

wherein:

Z is —(CH$_2$)$_x$— wherein x is 1, 2, 3 or 4 or —O—(CH$_2$)$_z$— wherein z is 2, 3 or 4;

R$^2$ is independently selected from hydrogen, carbamate, aryl, alkyl, allyl, and arylalkyl;

each R$^6$ is independently aryl, alkyl, cycloalkyl or haloalkyl, wherein each of said alkyl, cycloalkyl and haloalkyl groups optionally includes O or N heteroatoms in place of a carbon in the chain and two R$^6$'s on adjacent ring atoms or on the same ring atom together with the ring atom(s) to which they are attached optionally form a 3-8-membered cycle;

y is 0, 1, 2, 3 or 4;

R$^{12}$ is selected from:

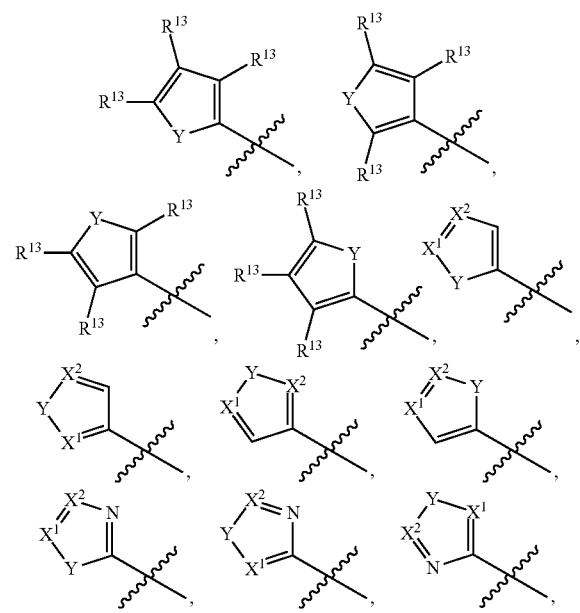

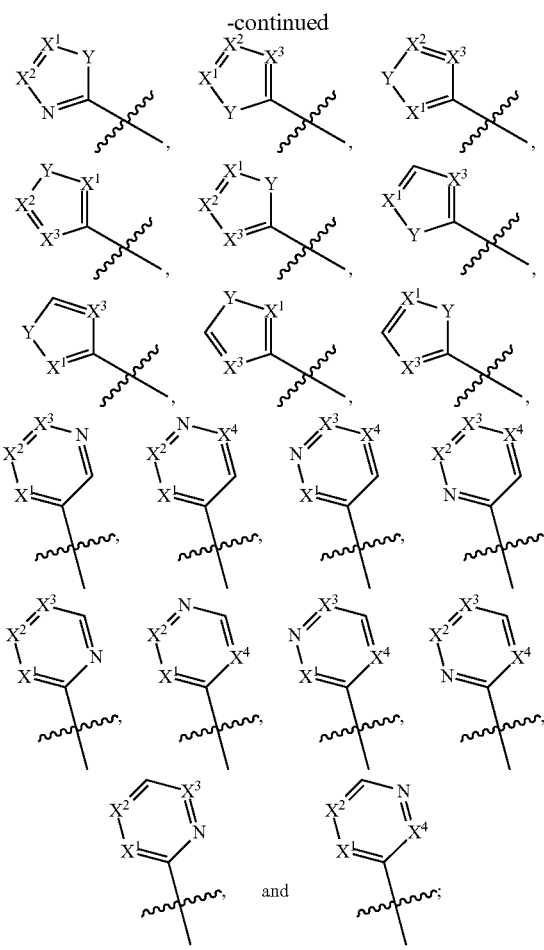

Y is NH, O, S, or NR$^{14}$;

X$^1$, X$^2$, X$^3$, X$^4$, and X$^5$ are independently N or CR$^{13}$, wherein at least one of X$^1$, X$^2$, X$^3$, X$^4$, and X$^5$ is CR$^{13}$;

R$^{13}$ is selected independently at each instance from: R$^{11}$ and R$^7$, wherein one R$^{13}$ is R$^7$;

R$^{14}$ is selected from: —C(O)H, —C(O)alkyl, —C(S) alkyl, alkyl, aryl, heteroaryl, arylalkyl, and heteroarylalkyl;

R$^7$ is -(alkylene)$_m$-heterocyclo, -(alkylene)$_m$-heteroaryl, -(alkylene)$_m$-NR$^8$R$^9$, -(alkylene)$_m$-C(O)—NR$^8$R$^9$; -(alkylene)$_m$-C(O)—O-alkyl; -(alkylene)$_m$-O—R$^{10}$, -(alkylene)$_m$-S(O)$_n$—R$^{10}$, or -(alkylene)$_m$-S(O)$_n$—NR$^8$R$^9$; any of which may be optionally independently substituted with one or more R$^x$ groups as allowed by valance, and wherein two R$^x$ groups bound to the same or adjacent atom may optionally combine to form a ring and wherein m is 0 or 1 and n is 0, 1 or 2;

R$^8$ and R$^9$ at each occurrence are independently:

(i) hydrogen or (ii) alkyl, cycloalkyl, heterocyclo, aryl, heteroaryl, cycloalkylalkyl, heterocycloalkyl, arylalkyl, or heteroarylalkyl; any of which may be optionally independently substituted with one or more R$^x$ groups as allowed by valance, and wherein two R$^x$ groups bound to the same or adjacent atom may optionally combine to form a ring; or R$^8$ and R$^9$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;

$R^{10}$ and $R^{10*}$ at each occurrence is:

(i) hydrogen or (ii) alkyl, alkenyl, alkynyl, cycloalkyl, heterocyclo, aryl, heteroaryl, cycloalkylalkyl, heterocycloalkyl, arylalkyl, or heteroarylalkyl; any of which may be optionally independently substituted with one or more $R^x$ groups as allowed by valance;

$R^x$ at each occurrence is independently halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^{10}$, -(alkylene)$_m$-O-alkylene-OR$^{10}$, -(alkylene)$_m$-S(O)$_n$—R$^{10}$, -(alkylene)$_m$-NR$^8$R$^9$, -(alkylene)$_m$-CN, -(alkylene)$_m$-C(O)—R$^{10}$, -(alkylene)$_m$-C(S)—R$^{10}$, -(alkylene)$_m$-C(O)—OR$^{10}$, -(alkylene)$_m$-O—C(O)—R$^{10}$, -(alkylene)$_m$-C(S)—OR$^{10}$, -(alkylene)$_m$-C(O)-(alkylene)$_m$-NR$^8$R$^9$, -(alkylene)$_m$-C(S)—NR$^8$R$^9$, -(alkylene)$_m$-N(R$^8$)—C(O)—NR$^8$R$^9$, -(alkylene)$_m$-N(R$^8$)—C(S)—NR$^8$R$^9$, -(alkylene)$_m$-N(R$^8$)—C(O)—R$^{10}$, -(alkylene)$_m$-N(R$^8$)—C(S)—R$^{10}$, -(alkylene)$_m$-O—C(O)—NR$^8$R$^9$, -(alkylene)$_m$-O—C(S)—NR$^8$R$^9$, -(alkylene)$_m$-SO$_2$—NR$^8$R$^9$, -(alkylene)$_m$-N(R$^8$)—SO$_2$—R$^{10}$, -(alkylene)$_m$-N(R$^8$)—SO$_2$—NR$^8$R$^9$, -(alkylene)$_m$-N(R$^8$)—C(O)—OR$^{10}$) -(alkylene)$_m$-N(R$^8$)—C(S)—OR$^{10}$, or -(alkylene)$_m$-N(R$^8$)—SO$_2$—R$^{10}$;

wherein: said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{10*}$, -(alkylene)$_m$-S(O)$_n$—R$^{10*}$, -(alkylene)$_m$-NR$^{8*}$R$^{9*}$, -(alkylene)$_m$-C(O)—R$^{10*}$, -(alkylene)$_m$-C(=S)R$^{10*}$, -(alkylene)$_m$-C(=O)OR$^{10*}$, -(alkylene)$_m$-OC(=O)R$^{10*}$, -(alkylene)$_m$-C(S)—OR$^{10*}$, -(alkylene)$_m$-C(O)—NR$^{8*}$R$^{9*}$, -(alkylene)$_m$-C(S)—NR$^{8*}$R$^{9*}$, -(alkylene)$_m$-N(R$^{8*}$)—C(O)—NR$^{8*}$R$^{9*}$, -(alkylene)$_m$-N(R$^{8*}$)—C(S)—NR$^{8*}$R$^{9*}$, -(alkylene)$_m$-N(R$^{8*}$)—C(O)—R$^{10*}$, -(alkylene)$_m$-N(R$^{8*}$)—C(S)—R$^{10*}$, -(alkylene)$_m$-O—C(O)—NR$^{8*}$R$^{9*}$, -(alkylene)$_m$-O—C(S)—NR$^{8*}$R$^{9*}$, -(alkylene)$_m$-SO$_2$—NR$^{8*}$R$^{9*}$, -(alkylene)$_m$-N(R$^{8*}$)—SO$_2$—R$^{10*}$, -(alkylene)$_m$-N(R$^{8*}$)—SO$_2$—NR$^{8*}$R$^{9*}$, -(alkylene)$_m$-N(R$^{8*}$)—C(O)—OR$^{10*}$, -(alkylene)$_m$-N(R$^{8*}$)—C(S)—OR$^{10*}$, or -(alkylene)$_m$-N(R$^{8*}$)—SO$_2$—R$^{10*}$;

n is 0, 1 or 2;

m is 0 or 1;

$R^{8*}$ and $R^{9*}$ at each occurrence are independently:

(i) hydrogen or (ii) alkyl, alkenyl, alkynyl cycloalkyl, heterocyclo, aryl, heteroaryl, cycloalkylalkyl, heterocycloalkyl, arylalkyl, or heteroarylalkyl; any of which may be optionally independently substituted with one or more $R^x$ groups as allowed by valance; or $R^{8*}$ and $R^{9*}$ together with the nitrogen atom to which they are attached may combine to form a heterocyclo ring optionally independently substituted with one or more $R^x$ groups as allowed by valance; and $R^{11}$ is selected independently at each instance from: hydrogen, halogen, alkyl, alkenyl, alkynyl cycloalkyl, heterocyclo, aryl, heteroaryl, cycloalkylalkyl, heterocycloalkyl, arylalkyl, or heteroarylalkyl.

In an additional embodiment of the present invention the coupling of a sulfone with a heteroaryl amine produces a compound of Formula X-a:

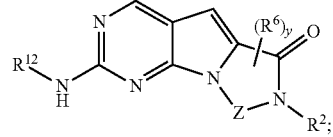

(X-a)

wherein:

Z is —(CH$_2$)$_x$— wherein x is 1, 2, 3 or 4; or —O—(CH$_2$)$_z$— wherein z is 2, 3 or 4;

$R^2$ is independently selected from hydrogen, carbamate, aryl, alkyl, allyl, and arylalkyl;

each $R^6$ is independently aryl, alkyl, cycloalkyl or haloalkyl, wherein each of said alkyl, cycloalkyl and haloalkyl groups optionally includes O or N heteroatoms in place of a carbon in the chain and two $R^6$'s on adjacent ring atoms or on the same ring atom together with the ring atom(s) to which they are attached optionally form a 3-8-membered cycle;

y is 0, 1, 2, 3 or 4;

$R^{12}$ is selected from:

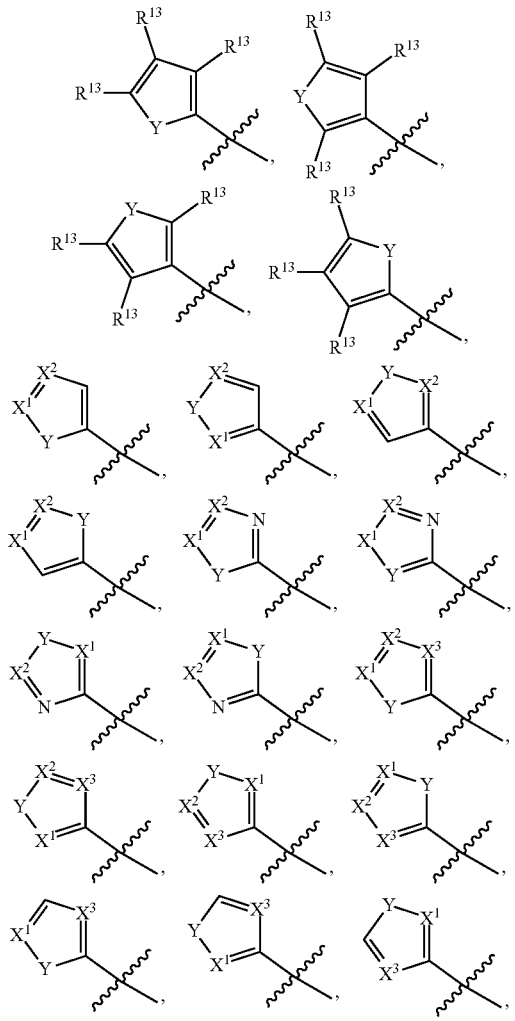

-continued

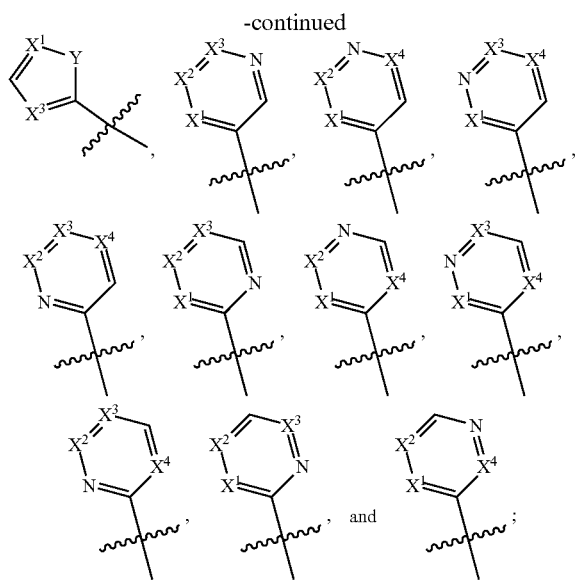

Y is NH, O, S, or NR$^{14}$;

X$^1$, X$^2$, X$^3$, and X$^4$, are independently N or CR$^{13}$, wherein at least one of X$^1$, X$^2$, X$^3$, and X$^4$, is CR$^{13}$;

R$^{13}$ is selected independently at each instance from: R$^{11}$ and R$^7$, wherein one R$^{13}$ is R$^7$;

R$^{14}$ is selected from: —C(O)H, —C(O)alkyl, —C(S)alkyl, alkyl, aryl, heteroaryl, arylalkyl, and heteroarylalkyl;

R$^7$ is -(alkylene)$_m$-heterocyclo, -(alkylene)$_m$-heteroaryl, -(alkylene)$_m$-NR$^8$R$^9$, -(alkylene)$_m$-C(O)—NR$^8$R$^9$; -(alkylene)$_m$-C(O)—O-alkyl; -(alkylene)$_m$-O—R$^{10}$, -(alkylene)$_m$-S(O)$_n$—R$^{10}$, or -(alkylene)$_m$-S(O)$_n$—NR$^8$R$^9$; any of which may be optionally independently substituted with one or more R$^x$ groups as allowed by valance, and wherein two R$^x$ groups bound to the same or adjacent atom may optionally combine to form a ring;

R$^8$ and R$^9$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl; any of which may be optionally independently substituted with one or more R$^x$ groups as allowed by valance, and wherein two R$^x$ groups bound to the same or adjacent atom may optionally combine to form a ring; or R$^8$ and R$^9$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;

R$^{10}$ is:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl; any of which may be optionally independently substituted with one or more R$^x$ groups as allowed by valance;

R$^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, or heterocycloalkyl;

n is 0, 1, or 2;

m is 0 or 1; and

R$^{11}$ is selected independently at each instance from: hydrogen, halogen, alkyl, alkenyl, alkynyl cycloalkyl, heterocyclo, aryl, heteroaryl, cycloalkylalkyl, heterocycloalkyl, arylalkyl, and heteroarylalkyl.

In an additional embodiment, R$^{12}$ is selected from:

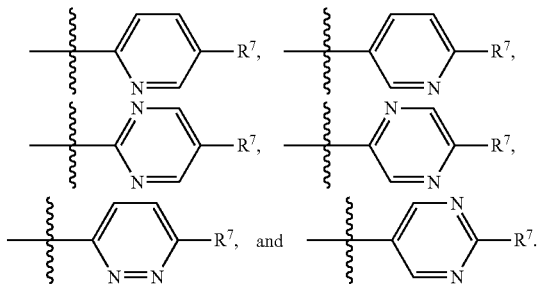

In an additional embodiment, R$^{12}$ is selected from:

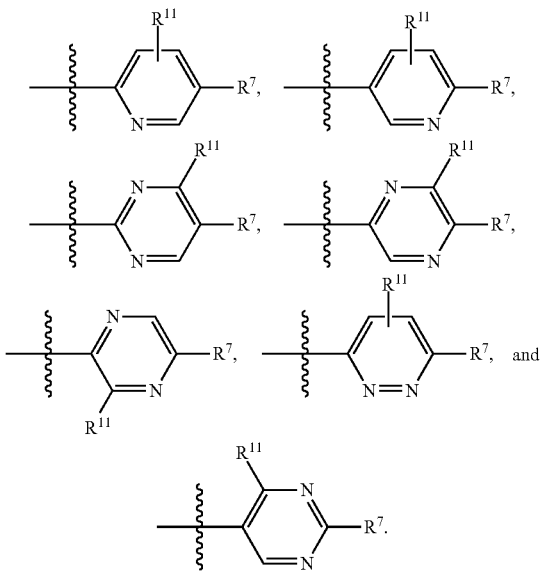

In an additional embodiment, R$^{12}$ is

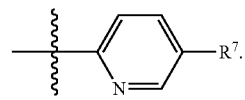

In an additional embodiment of the present invention the coupling of a sulfone with a heteroaryl amine produces a compound of Formula X-b:

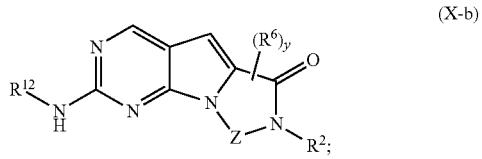

(X-b)

wherein:
R[12] is

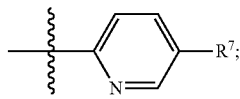

and the other variables are as defined in Formula X-a.

The present invention thus includes at least the following features:
(i) a process to synthesize a 2'-(heteroaryl)-lactam-pyrrolo[2,3-d]pyrimidine starting from an alkyl 4-halo-2-(alkylthio)pyrimidine-5-carboxylate;
(ii) a process to synthesize a 2'-(heteroaryl)-lactam-pyrrolo[2,3-d]pyrimidine starting from an 4-halo-2-(alkylthio)pyrimidine-5-carbaldehyde;
(iii) a process to synthesize a 2'-(heteroaryl)-lactam-pyrrolo[2,3-d]pyrimidine from a 2'-(alkylsulfonyl)-lactam-pyrrolo[2,3-d]pyrimidine;
(iv) a process to synthesize a 2'-(heteroaryl)-lactam-pyrrolo[2,3-d]pyrimidine from a 2'-(alkylsulfinyl)-lactam-pyrrolo[2,3-d]pyrimidine;
(v) a process to synthesize a compound of Formula IV including nucleophilic attack of a halopyrimidine by a compound of Formula I, cyclization of the resultant compound, conversion of the hydroxy group to a leaving group, dehydration of the resultant compound, and optional oxidation to the sulfoxide or sulfone;
(vi) a process to synthesize a compound of Formula III including nucleophilic attack of a halopyrimidine by a compound of Formula I, and cyclization of the resultant compound;
(vii) a process to synthesize a compound of Formula II including nucleophilic attack of a halopyrimidine by a compound of Formula I;
(viii) a process to synthesize a compound of Formula I; and
(ix) a compound of Formula II.

DETAILED DESCRIPTION

I. Terminology

Figure 1:
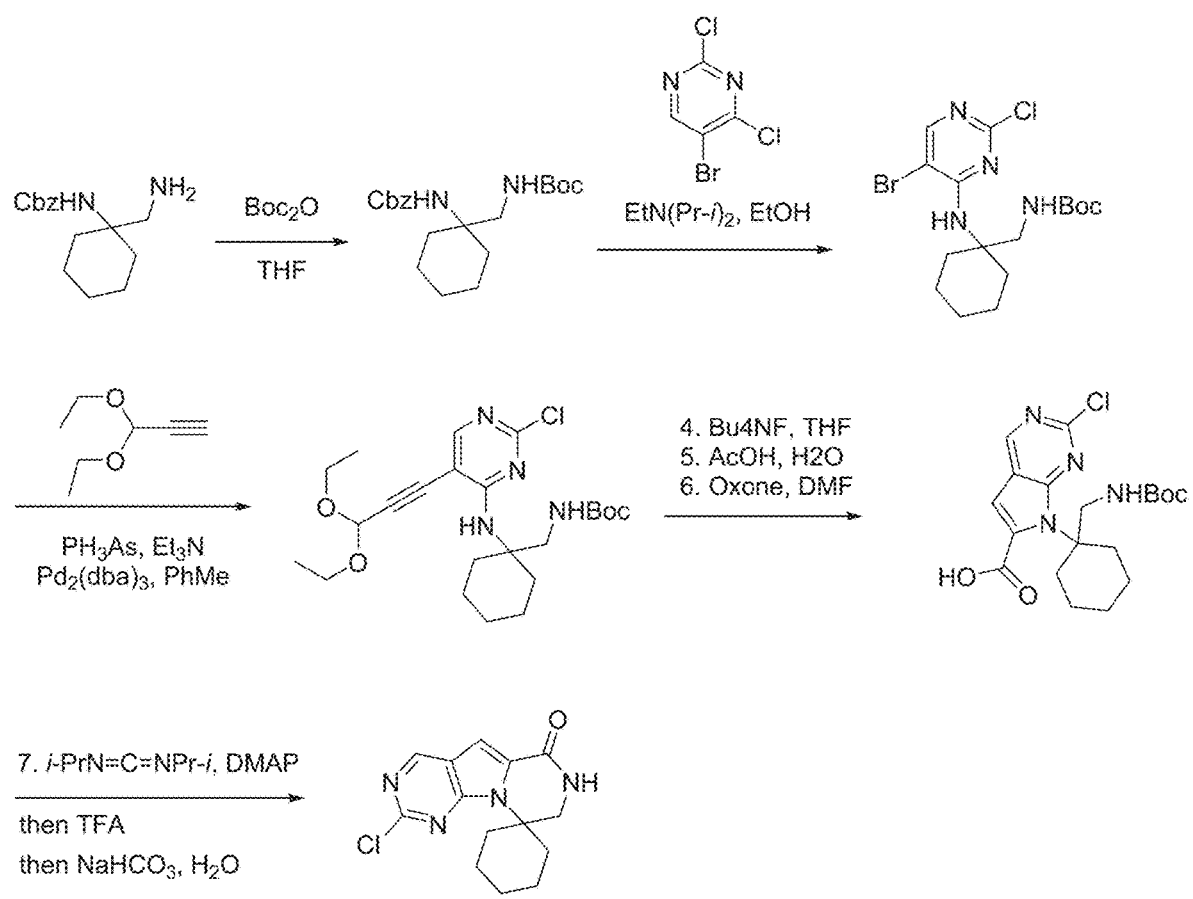
FIG. 1 illustrates the synthesis of Intermediate 1K from benzyl (1-(aminomethyl)cyclohexyl)carbamate. In Step 1 benzyl (1-(aminomethyl)cyclohexyl)carbamate is Boc-protected. In Step 2 nucleophilic attack by the Boc-protected species on 5-bromo-2,4-dichloropyrimidine affords selective displacement of chloride to afford a dihalo species. In Step 3 the dihalo species is coupled selectively to displace bromide and afford an internal alkynyl species. In Steps 4-6 internal alkynyl species is cyclized to a 6-5 heteroaryl species. In Steps 7-9 the 6-5 heteroaryl species is further cyclized to afford Intermediate 1K.
Figure 2:
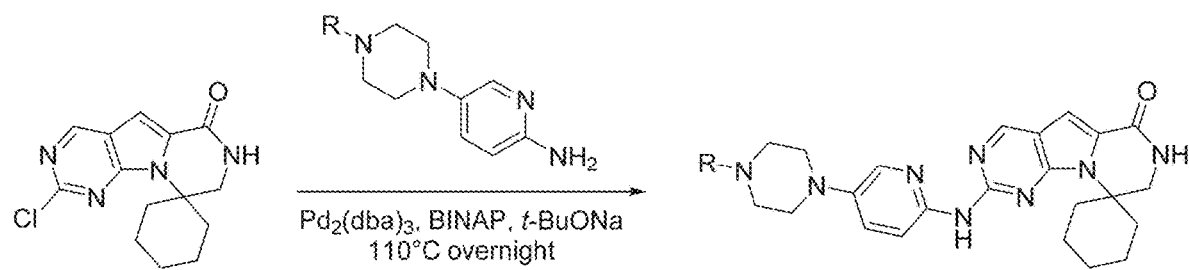
FIG. 2 illustrates the SNAr coupling of Intermediate 1K to an appropriately substituted anilino species to afford a CDK inhibitor.

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula II with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any of A, C, L or B. In one non-limiting embodiment, the substitution of a hydrogen atom for a deuterium atom occurs within an R group selected from any of $R^1$, $R^2$, $R^3$, $R^4$, $R^5$, $R^6$, $R^7$, $R^8$, $R^{8*}$, $R^9$, $R^{9*}$, $R^{10}$, $R^{10*}$, $R^{11}$, $R^{12}$, $R^{13}$, $R^{14}$, and $R^x$. For example, when any of the R groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("—") that is not between two letters or symbols is used to indicate a point of attachment for a substituent. For example, —(C=O)$NH_2$ is attached through carbon of the keto (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted.

In an alternative embodiment, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In an alternative embodiment, the alkoxy group is optionally substituted as described above. In an alternative embodiment, the thioalkyl group is optionally substituted as described above.

"Amino" is —$NH_2$.

"Amide" or "carboxamide" is —C(O)$NR^aR^b$ wherein $R^a$ and $R^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, $R^a$ and $R^b$ can form a $C_3$-$C_7$heterocyclic ring. In an alternative embodiment, the $R^a$ and $R^b$ groups are each independently optionally substituted as described above.

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the carbocyclyl group can be saturated or can contain one or more carbon-carbon double or triple bonds. In an alternative embodiment, "Carbocyclyl" also includes ring systems wherein the carbocyclyl ring, as defined above, is fused with one or more heterocyclyl, aryl or heteroaryl groups wherein the point of attachment is on the carbocyclyl ring, and in such instances, the number of carbons continue to designate the number of carbons in the carbocyclic ring system. In an alternative embodiment, each instance of carbocycle is optionally substituted with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and pentafluoroethyl.

"Haloalkoxy" indicates a haloalkyl group as defined herein attached through an oxygen bridge (oxygen of an alcohol radical).

"Halo" or "halogen" indicates independently any of fluoro, chloro, bromo or iodo.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl.

"Arylalkyl" is an aryl group as defined herein attached through an alkyl group. Non-limiting examples of arylalkyl groups include:

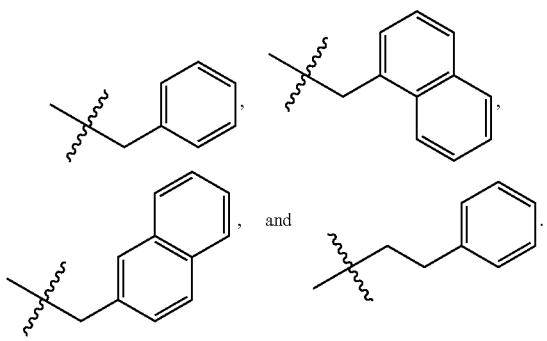

"Aryloxy" is an aryl group as defined herein attached through a —O— linker. Non-limiting examples of aryloxy groups include:

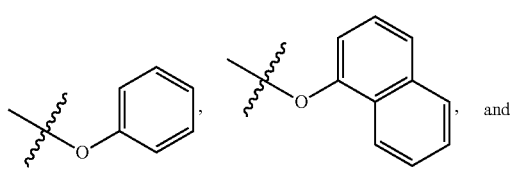

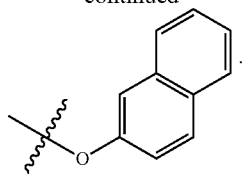

"Alkylsulfinyl" and "alkyl sulfoxide" as defined herein are represented by

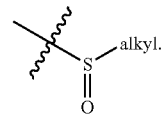

"Alkylsulfonyl" and "alkyl sulfone" as defined herein are represented by

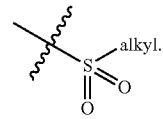

II. Coupling of Heteroaryl Amines to Sulfones/Sulfoxides

It has been discovered that 2'-(heteroaryl)-lactam-pyrrolo [2,3-d]pyrimidines are advantageously prepared by coupling an alkyl sulfone or alkyl sulfoxide substituted fused pyrimidine with a heteroaryl amine to form the central disubstituted amine. Using an alkyl sulfone or alkyl sulfoxide substituted fused pyrimidine instead of a chloro substituted fused pyrimidine increases the yield of the coupled diamine product and decreases the required temperature, resulting in fewer side products and thus impurities.

Generally, the coupling can occur in a polar aprotic solvent at a reduced temperature if desired in the presence of a base that facilitates the reaction. For example, the coupling can be achieved by adding a sulfone to a stirred solution of heteroaryl amine in THF at room temperature or lower, in the presence of LiHMDS. Though various orders of addition are possible that would achieve a comparable result, the amine is preferably added last to reduce the occurrence of dimerization side reactions.

In one non-limiting embodiment, the pyrimidine is fused to a pyrrole/spirocyclic lactam ring system. For example, the sulfone can be 2'-(methylsulfonyl)-7',8'-dihydro-6'H-spiro [cyclohexane-1,9'-pyrazino[1',2':1,5]pyrrolo[2,3-d]pyrimidin]-6'-one or a derivative thereof.

In an alternative embodiment, the pyrimidine is fused to a pyrrole/cyclic lactam system. For example, the sulfone can be 2-(methylsulfonyl)-8,9-dihydropyrazino[1',2':1,5]pyrrolo [2,3-d]pyrimidin-6(7H)-one or a derivative thereof.

Step 1: Method to Couple Heteroaryl Amines to Sulfones/Sulfoxides

In Step 1 a heteroaryl amine is reacted with an 2'-(alkylsulfonyl)-lactam-pyrrolo[2,3-d]pyrimidine or 2'-(alkylsulfinyl)-lactam-pyrrolo[2,3-d]pyrimidine in the presence of a base to afford a 2'-(heteroaryl)-lactam-pyrrolo[2,3-d]pyrimidine. The heteroaryl amine is mixed with an appropriate base in a suitable solvent, typically a neutral organic solvent that both reactants dissolve in. The 2'-(alkylsulfonyl)-lactam-pyrrolo[2,3-d]pyrimidine or 2'-(alkylsulfinyl)-lactam-pyrrolo[2,3-d]pyrimidine is then added as one or more additions. Any molar ratio of the two reactants can be used that achieves the desired results. Typically, an excess of the heteroaryl amine is useful, for example about 3 equiv. of heteroaryl amine to about 1.0 equiv. of sulfone or sulfoxide. The reaction can be carried out at any temperature that allows the reaction to take place. It has been found that the reaction can be conducted at below room temperature. The reaction is allowed sufficient time to provide the desired yield, after which the batch is purified by any suitable means, including filtration, crystallization, and column chromatography, to afford a 2'-(heteroaryl)-lactam-pyrrolo[2,3-d]pyrimidine. In one non-limiting illustrative embodiment, the heteroaryl amine is 5-(4-methylpiperazin-1-yl)pyridin-2-amine, the 2'-(alkylsulfonyl)-lactam-pyrrolo[2,3-d]pyrimidine is 2'-(methylsulfonyl)-7',8'-dihydro-6'H-spiro[cyclohexane-1,9'-pyrazino[1',2':1,5]pyrrolo[2,3-d]pyrimidin]-6'-one, the base is LiHMDS, the solvent is THF, the temperature is about 5° C., and the time is about one hour.

The base used in Step 1 can be any suitable base, including but not limited to LiHMDS, NaHMDS, NaH, KH, LDA, DIPEA (N,N-diisopropylethylamine), DMAP (4-Dimethylaminopyridine), DBU (1,8 Diazabicycloundec-7-ene), TEA (Triethylamine), pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO (1,4-diazabicyclo[2.2.2]octane), 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, or Trizma. In one non-limiting embodiment, the base is selected from LiHMDS, NaHMDS, NaH, KH, and LDA. In an alternative embodiment, multiple bases are used in Step 1.

The solvent used in Step 1 can be any suitable organic solvent, including but not limited to DMAc (N,N-dimethylacetamide), DCM (Dichloromethane), THF (Tetrahydrofuran), DMF (N,N-dimethylformamide), ACN (Acetonitrile), DMAP (4-Dimethylaminopyridine), water, acetic acid, acetone, dioxane, benzene, 1-butanol, 2-butanol, tert-butyl alcohol, carbon tetrachloride, chloroform, cyclohexane, hexanes, diethyl ether, diglyme, DME (Dimethoxyethane), DMSO (Dimethylsulfoxide), ethanol, ethyl acetate, ethylene glycol, glycerin, heptane, HMPA (Hexamethylphosphoramide), methanol, MTBE (Methyl Tertiary Butyl Ether), NMP (N-Methyl-2-Pyrrolidone), pentane, pyridine, toluene, hydrochloric acid, and triethyl amine. In one non-limiting embodiment, the solvent is selected from THF, ACN, DMAP, and DMSO. In an alternative embodiment, a mixture of solvents is used in Step 1.

In an additional embodiment the solvent used in Step 1 is dioxane. In another additional embodiment, the solvent is selected from DCM, EtOAc, ethanol, dioxane, tert-butyl alcohol, and THF.

The temperature used in Step 1 can be, for example, from about 20 to about 25° C., about 15 to about 30° C., about 10 to about 35° C., about 5 to about 40° C., or from about 0 to about 50° C. In one non-limiting embodiment, the temperature is maintained at or below room temperature. Alternatively, while less typical, the reaction can be carried out at elevated temperatures.

The reaction can be allowed to proceed for a sufficient time to obtain the desired yield of product. For example the reaction may proceed in Step 1 for about 10 minutes to about 10 hours, about 30 minutes to about 5 hours, about 45 minutes to about 3 hours, or about 1 to about 2 hours.

In one embodiment the crude reaction mixture is quenched with water. In another embodiment the crude reaction mixture is quenched with saturated ammonium chloride.

In one embodiment the sulfone is added portion-wise with at least about 5, 10, 15, or 20 minute stirring intervals. In one embodiment the sulfone is added portion-wise with an at least 10 minute stirring interval.

In one embodiment the 2'-(heteroaryl)-lactam-pyrrolo[2,3-d]pyrimidine is used as a free base. In another embodiment the 2'-(heteroaryl)-lactam-pyrrolo[2,3-d]pyrimidine is converted to a salt (for example Step 2).

In one embodiment the 2'-(heteroaryl)-lactam-pyrrolo[2,3-d]pyrimidine is a compound of Formula X.

WO 2013/163239 and WO 2015/061407 describe the coupling of a heteroaryl amine to a lactam-pyrrolo[2,3-d]pyrimidine through a leaving group selected from Cl, Br, I, —S-Me, —S-aryl, —S-heteroaryl, SOMe, $SO_2Me$, SOalkyl, $SO_2$alkyl, SOcycloalkyl, $SO_2$cycloalkyl, SOaryl, $SO_2$aryl, hydroxy, hydroxyalkyl, hydroxyaryl, and hydroxyheteroaryl.

Step 2: Method to Form Salt of 2'-(heteroaryl)-lactam-pyrrolo[2,3-d]pyrimidine

In Step 2 a 2'-(heteroaryl)-lactam-pyrrolo[2,3-d]pyrimidine is reacted with an acid to afford a 2'-(heteroaryl)-lactam-pyrrolo[2,3-d]pyrimidine salt. The 2'-(heteroaryl)-lactam-pyrrolo[2,3-d]pyrimidine is mixed with an appropriate acid in a suitable solvent, typically a neutral organic solvent that both reactants dissolve in. In one embodiment the solvent is an acid. In addition to the first solvent and acid, an anti-solvent can be used. Any molar ratio of the two reactants can be used that achieves the desired results. Typically an excess of the acid is useful. The reaction can be carried out at any temperature that allows the reaction to take place. It has been found that the reaction can be conducted at room temperature. The reaction is allowed sufficient time to provide the desired yield, after which the batch is purified by any suitable means, including filtration, crystallization, and column chromatography, to afford a 2'-(heteroaryl)-lactam-pyrrolo[2,3-d]pyrimidine salt.

In one embodiment the acid is HCl.

The solvent used in Step 2 can be any suitable organic solvent, including but not limited to DMAc (N,N-dimethylacetamide), DCM (Dichloromethane), THF (Tetrahydrofuran), DMF (N,N-dimethylformamide), ACN (Acetonitrile), DMAP (4-Dimethylaminopyridine), water, acetic acid, acetone, dioxane, benzene, 1-butanol, 2-butanol, tert-butyl alcohol, carbon tetrachloride, chloroform, cyclohexane, hexanes, diethyl ether, diglyme, DME (Dimethoxyethane), DMSO (Dimethylsulfoxide), ethanol, ethyl acetate, ethylene glycol, glycerin, heptane, HMPA (Hexamethylphosphoramide), methanol, MTBE (Methyl Tertiary Butyl Ether), NMP (N-Methyl-2-Pyrrolidone), pentane, pyridine, toluene, hydrochloric acid, and triethyl amine. In one non-limiting embodiment, the solvent is selected from DCM, methanol, acetone, and DMSO. In an alternative embodiment, a mixture of solvents is used in Step 2.

In one embodiment the solvent is about 6M aqueous HCl. In another embodiment the solvent is about 4M HCl in dioxane. In another embodiment the solvent is a mixture of solvents. In one embodiment the mixture of solvents is a mixture of DCM and methanol.

In an additional embodiment the solvent is about 2M aqueous HCl. In another additional embodiment the solvent is 2M aqueous HCl.

The anti-solvent used in Step 2 can be any suitable organic solvent, including but not limited to DMAc (N,N-dimethylacetamide), DCM (Dichloromethane), THF (Tetrahydrofuran), DMF (N,N-dimethylformamide), ACN (Acetonitrile), DMAP (4-Dimethylaminopyridine), water, acetic acid, acetone, dioxane, benzene, 1-butanol, 2-butanol, tert-butyl alcohol, carbon tetrachloride, chloroform, cyclohexane, hexanes, diethyl ether, diglyme, DME (Dimethoxyethane), DMSO (Dimethylsulfoxide), ethanol, ethyl acetate, ethylene glycol, glycerin, heptane, HMPA (Hexamethylphosphoramide), methanol, MTBE (Methyl Tertiary Butyl Ether), NMP (N-Methyl-2-Pyrrolidone), pentane, pyridine, toluene, hydrochloric acid, and triethyl amine. In one non-limiting embodiment, the solvent is selected from DCM, methanol, acetone, and DMSO. In an alternative embodiment, a mixture of solvents is used in Step 2.

The temperature used in Step 2 can be, for example, from about 20 to about 25° C., about 15 to about 30° C., about 10 to about 35° C., about 5 to about 40° C., about 0 to about 50° C., or from about 0 to about 70° C. In one non-limiting embodiment, the temperature is maintained at or below room temperature. Alternatively, while less typical, the reaction can be carried out at elevated temperatures.

The reaction can be allowed to proceed for a sufficient time to obtain the desired yield of product. For example, the reaction may proceed in Step 2 for about 10 minutes to about 10 hours, about 30 minutes to about 5 hours, about 45 minutes to about 3 hours, or about 1 to about 2 hours.

In one embodiment the salt is a di-HCl salt.

IIIA. Process of Preparing Sulfone/Sulfoxide from Pyrimidine Ester

It has been discovered that 2'-(alkylsulfonyl)-lactam-pyrrolo[2,3-d]pyrimidines and the sulfoxide and sulfide analogs as well can be prepared in seven or fewer steps from alkyl 4-halo-2-(alkylthio)pyrimidine-5-carboxylates. In one non-limiting embodiment, the 2'-(alkylsulfonyl)-lactam-pyrrolo[2,3-d]pyrimidine is a spirocycle, for example, 2'-(methylsulfonyl)-7',8'-dihydro-6'H-spiro[cyclohexane-1,9'-pyrazino[1',2':1,5]pyrrolo[2,3-d]pyrimidin]-6'-one.

Step 1: Preparation of alkyl 2-(alkylthio)-4-(lactam)pyrimidine-5-carboxylate

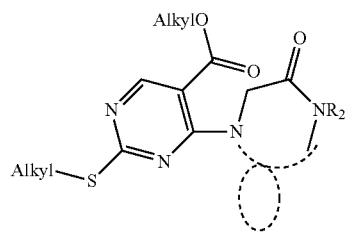

In Step 1 an alkyl 4-halo-2-(alkylthio)pyrimidine-5-carboxylate is reacted with a lactam amine in nucleophilic substitution reaction to afford an alkyl 2-(alkylthio)-4-(lactam)pyrimidine-5-carboxylate. The alkyl 4-halo-2-(alkylthio)pyrimidine-5-carboxylate and lactam amine are mixed in a suitable solvent, typically a neutral organic solvent that both reactants dissolve in along with a base that will facilitate the nucleophilic substitution reaction. Any molar ratio of the two reactants can be used that achieves the desired results. Typically a small molar excess of the lactam amine is useful, for example about 1.1 equiv. of lactam amine to about 1.0 equiv. of carboxylate. The reaction can be carried out at any temperature that allows the reaction to take place. It has been found that the reaction can be facilitated with heat, including up to reflux. The reaction is allowed sufficient time to provide the desired yield, after which the batch is optionally cooled and purified by any suitable means, including filtration, crystallization, and column chromatography, to afford an alkyl 2-(alkylthio)-4-(lactam)pyrimidine-5-carboxylate. In one non-limiting illustrative embodiment, the alkyl 4-halo-2-(alkylthio)pyrimidine-5-carboxylate is ethyl 4-chloro-2-(methylthio)pyrimidine-5-carboxylate, the lactam amine is a spirolactam, the base is DIPEA, the solvent is DMAc, the temperature is about 95° C., and the time is about 60 hours.

The base used in Step 1 can be any suitable organic base, including but not limited to DIPEA (N,N-diisopropylethylamine), DMAP (4-Dimethylaminopyridine), DBU (1,8 Diazabicycloundec-7-ene), TEA (Triethylamine), pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO (1,4-diazabicyclo[2.2.2]octane), 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, or Trizma. In one non-limiting embodiment, the base is selected from DIPEA, DMAP, DBU, TEA, and pyridine. In an alternative embodiment, multiple bases are used in Step 1.

The solvent used in Step 1 can be any suitable organic solvent, including but not limited to DMAc (N,N-dimethylacetamide), DCM (Dichloromethane), THF (Tetrahydrofuran), DMF (N,N-dimethylformamide), TFA (Trifluoroacetic acid), ACN (Acetonitrile), DMAP (4-Dimethylaminopyridine), water, acetic acid, acetone, dioxane, benzene, 1-butanol, 2-butanol, tert-butyl alcohol, carbon tetrachloride, chloroform, cyclohexane, hexanes, diethyl ether, diglyme, DME (Dimethoxyethane), DMSO (Dimethylsulfoxide), ethanol, ethyl acetate, ethylene glycol, glycerin, heptane, HMPA (Hexamethylphosphoramide), methanol, MTBE (Methyl Tertiary Butyl Ether), NMP (N-Methyl-2-Pyrrolidone), pentane, pyridine, toluene, hydrochloric acid, and triethyl amine. In one non-limiting embodiment, the solvent is selected from DMAc, ACN, DMAP, and DMSO. In an alternative embodiment, a mixture of solvents is used in Step 1.

In an additional embodiment the solvent used in Step 1 is dioxane. In another additional embodiment, the solvent is selected from DCM, EtOAc, ethanol, dioxane, tert-butyl alcohol, and THF.

The temperature used in Step 1 can be, for example, from about 50 to about 150° C., about 60 to about 125° C., about 70 to about 110° C., about 80 to about 100° C., or from about 90 to about 100° C. In one non-limiting embodiment, the temperature is selected from about 80 to about 100° C. In an alternative embodiment, the reaction temperature is higher than the solvent reflux by use of a reaction vessel that can maintain elevated pressures. Alternatively, while less typical, the reaction can be carried out at room temperature or below.

The reaction can be allowed to proceed for a sufficient time to obtain the desired yield of product. For example, the reaction may proceed in Step 1 for about 5 to about 110 hours, about 15 to about 100 hours, about 25 to about 90 hours, about 35 to about 80 hours, or about 50 to about 70 hours. It should be understood by those of skill in the art that the time and temperature of the reaction are related. For example, if a higher temperature is used a lower reaction time may obtain the desired yield.

Step 2: Optional Protection of alkyl 2-(alkylthio)-4-(lactam)pyrimidine-5-carboxylate

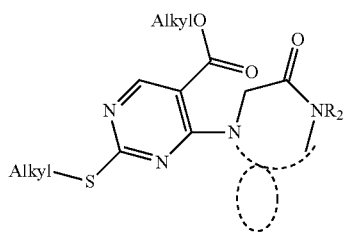

In Step 2 an alkyl 2-(alkylthio)-4-(lactam)pyrimidine-5-carboxylate is reacted with a protecting group reagent to afford a protected alkyl 2-(alkylthio)-4-(lactam)pyrimidine-5-carboxylate. The alkyl 2-(alkylthio)-4-(lactam)pyrimidine-5-carboxylate and protecting group reagent are mixed in a suitable solvent, typically a neutral organic solvent that both reactants dissolve in along with a base that will facilitate the installation of the protecting group. Any molar ratio of the two reactants can be used that achieves the desired results. Typically, a small molar excess of the protecting group reagent is useful, for example about 1.5 equiv. of protecting group reagent to about 1.0 equiv. of alkyl 2-(alkylthio)-4-(lactam)pyrimidine-5-carboxylate. The reaction can be carried out at any temperature that allows the reaction to take place. The reaction is allowed sufficient time to provide the desired yield, after which the batch is purified by any suitable means, including filtration, crystallization, and column chromatography, to afford a protected alkyl 2-(alkylthio)-4-(lactam)pyrimidine-5-carboxylate. In one non-limiting embodiment, the alkyl 2-(alkylthio)-4-(lactam) pyrimidine-5-carboxylate is ethyl 2-(methylthio)-4-(3-oxo-1,4-diazaspiro[5.5]undecan-1-yl)pyrimidine-5-carboxylate, the protecting group reagent is Boc-anhydride, the base is DMAP, the solvent is dichloromethane, the temperature is about 25° C., and the time is about 3 hours.

In one non-limiting embodiment, the initial lactam amine used was already protected. In an alternative embodiment, the lactam substituted pyrimidine reacts appropriately without needing a protecting group.

The protecting group reagent used in Step 2 can be any suitable reagent that allows installation of any suitable protecting group, including but not limited to Boc-anhydride (tert-butyloxycarbonyl anhydride), Boc-Cl, CBz-Cl, (Carboxybenzyl chloride) methyl chloroformate, benzyl chloride, benzoyl chloride, allylic chloride, triflic anhydride, Tf-Cl, tosyl anhydride, and Ts-Cl. In one non-limiting embodiment, the protecting group is Boc and the suitable reagent is either Boc-anhydride or Boc-Cl. In an alternative embodiment, the protecting group is CBz and the suitable reagent is CBz-Cl.

The base used in Step 2 can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0] non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, and Trizma. In one non-limiting embodiment, the base is selected from DIPEA, DMAP, DBU, TEA, and pyridine. In an alternative embodiment, multiple bases are used in Step 2.

The solvent used in Step 2 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 2.

The temperature used in Step 2 can be, for example, from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 2 for about 0.1 to about 20 hours, about 0.5 to about 15 hours, about 1 to about 10 hours, about 1.5 to about 5 hours, or about 2 to about 4 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 3: Preparation of 5'-hydroxy-2'-(alkylthio)-lactam-pyrrolo[2,3-d]pyrimidine

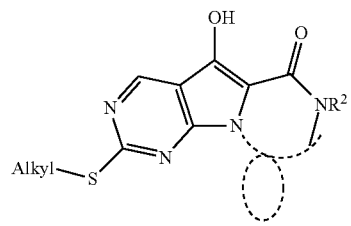

In Step 3 a protected alkyl 2-(alkylthio)-4-(lactam)pyrimidine-5-carboxylate is reacted with a base in an intramolecular cyclization to afford a 5'-hydroxy-2'-(alkylthio)- lactam-pyrrolo[2,3-d]pyrimidine. The protected alkyl 2-(alkylthio)-4-(lactam)pyrimidine-5-carboxylate and base are mixed in a suitable solvent, typically a neutral organic solvent that both the reactant and reagent dissolve in. Any molar ratio of the reactant and reagent can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford a 5'-hydroxy-2'-(alkylthio)-lactam-pyrrolo[2,3-d]pyrimidine. In one non-limiting embodiment, the protected alkyl 2-(alkylthio)-4-(lactam)pyrimidine-5-carboxylate is tert-butyl 1-(5-(ethoxycarbonyl)-2-(methylthio)pyrimidin-4-yl)-3-oxo-1,4-diazaspiro[5.5]undecane-4-carboxylate, the base is DBU, the solvent is THF, the temperature is about 5° C., and the time is about 2 hours.

The base used in Step 3 can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, or Trizma. In one non-limiting embodiment, the base is selected from DIPEA, DMAP, DBU, DABCO, TEA, and pyridine. In an alternative embodiment, multiple bases are used in Step 3.

The solvent used in Step 3 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 3.

The temperature used in Step 3 can be, for example, from about −50° C. to about 50° C., about −35° C. to about 40° C., about −10° C. to about 30° C., about −5° C. to about 20° C., or from about 0° C. to about 10° C. In one non-limiting embodiment, the temperature is selected from about 0° C. to about 10° C.

The reaction can be allowed to proceed for a sufficient time to obtain the desired yield of product. For example, the reaction may proceed in Step 3 for about 0.1 to about 20 hours, about 0.5 to about 15 hours, about 1 to about 10 hours, about 1.5 to about 5 hours, or about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 4: Preparation of 5'-Leaving Group-2'-(alkylthio)-lactam-pyrrolo[2,3-d]pyrimidine

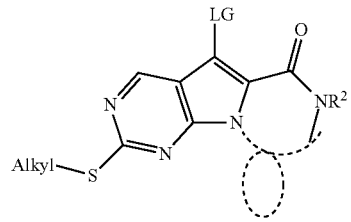

In Step 4 a 5'-hydroxy-2'-(alkylthio)-lactam-pyrrolo[2,3-d]pyrimidine is reacted with a leaving group reagent to afford a 5'-leaving group-2'-(alkylthio)-lactam-pyrrolo[2,3-d]pyrimidine. The 5'-hydroxy-2'-(alkylthio)-lactam-pyrrolo[2,3-d]pyrimidine and leaving group reagent are mixed in a suitable solvent, typically a neutral organic solvent that both the reactants dissolve in along with a base that will facilitate the reaction. Any molar ratio of the reactants can be used that achieves the desired results. Typically a small molar excess of the protecting group reagent is useful, for example about 1.6 equiv. of leaving group reagent to about 1.0 equiv. of 5'-hydroxy-2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford a 5'-leaving group-2'-(alkylthio)-lactam-pyrrolo[2,3-d]pyrimidine. In one non-limiting embodiment, the 5'-hydroxy-2'-(alkylthio)-lactam-pyrrolo[2,3-d]pyrimidine is tert-butyl 5'-hydroxy-2'-(methylthio)-6'-oxo-6'H-spiro[cyclohexane-1,9'-pyrazino[1',2':1,5]pyrrolo[2,3-d]pyrimidine]-7'(8'H)-carboxylate, the leaving group reagent is triflic anhydride, the base is TEA, the solvent is DCM, the temperature is about 0° C., and the time is about 3 hours.

The leaving group reagent used in Step 4 can be any suitable reagent that allows conversion of the hydroxyl group to any suitable leaving group, including but not limited to triflic anhydride, Tf-Cl, tosyl anhydride, and Ts-Cl. In one non-limiting embodiment, the protecting group is triflate and the suitable reagent is either triflic anhydride or Tf-Cl.

The base used in Step 4 can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, or Trizma. In one non-limiting embodiment, the base is selected from DIPEA, DMAP, DBU, trimethylamine, TEA, and pyridine. In an alternative embodiment, multiple bases are used in Step 4.

The solvent used in Step 4 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, diethyl ether, and THF. In an alternative embodiment, a mixture of solvents is used in Step 4. Typically, the solvent or mixture of solvents is aprotic so as to avoid reaction with the leaving group reagent.

The temperature used in Step 4 can be, for example, from about −50° C. to about 50° C., about −35° C. to about 35° C., about −25° C. to about 25° C., about −15° C. to about 15° C., or from about −5° C. to about 5° C. In one non-limiting embodiment, the temperature is selected from about −5° C. to about 5° C.

The reaction can be allowed to proceed for a sufficient time to obtain the desired yield of product. For example, the reaction may proceed in Step 4 for about 0.1 to about 20 hours, about 0.5 to about 15 hours, about 1 to about 10 hours, about 1.5 to about 5 hours, or about 2 to about 4 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 5: Preparation of 2'-(alkylthio)-lactam-pyrrolo [2,3-d]pyrimidine

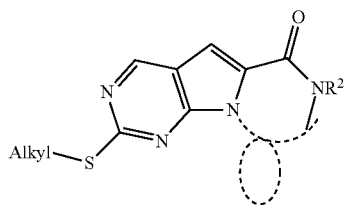

In Step 5 a 5'-leaving group-2'-(alkylthio)-lactam-pyrrolo [2,3-d]pyrimidine is reacted with a leaving group cleaving reagent to remove the leaving group and afford a 2'-(alkylthio)-lactam-pyrrolo[2,3-d]pyrimidine. The 5'-leaving group-2'-(alkylthio)-lactam-pyrrolo[2,3-d]pyrimidine and leaving group cleaving reagent are mixed in a suitable solvent, typically a neutral organic solvent that both the reactants dissolve in along with a catalyst that will facilitate the reaction. Any molar ratio of the reactants can be used that achieves the desired results. Typically a molar excess of the leaving group cleaving reagent is useful, for example about 2.0 equiv. of leaving group cleaving reagent to about 1.0 equiv. of 5'-leaving group-2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford a 2'-(alkylthio)-lactam-pyrrolo[2,3-d]pyrimidine. In one non-limiting embodiment, the 5'-leaving group-2'-(alkylthio)-lactam-pyrrolo[2,3-d]pyrimidine is tert-butyl 2'-(methylthio)-6'-oxo-5'-(((trifluoromethyl)sulfonyl)oxy)-6'H-spiro[cyclohexane-1,9'-pyrazino[1',2':1,5]pyrrolo[2,3-d]pyrimidine]-7'(8'H)-carboxylate, the leaving group cleaving reagent is triethylsilane, the catalyst is palladium tetrakis, the solvent is DMF, the temperature is about 50° C., and the time is about 14 hours.

The leaving group cleaving reagent used in Step 5 can be any suitable reagent that allows removal of the leaving group, including but not limited to trialkylsilanes. In one non-limiting embodiment, the leaving group cleaving reagent is triethylsilane.

The catalyst used in Step 5 can be any suitable organometallic catalyst, including but not limited to Pd/C, palladium tetrakis, palladium acetate, [1,1'-Bis(diphenylphosphino)ferrocene]dichloropalladium(II), Tris(dibenzylideneacetone)dipalladium(0), and allylpalladium (II) chloride. In an alternative embodiment, multiple catalysts or a catalyst and cocatalyst are used in Step 5.

The solvent used in Step 5 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DMF, DMSO, ACN, and NMP. In an alternative embodiment, a mixture of solvents is used in Step 5. Typically, the solvent or mixture of solvents is aprotic so as to avoid reaction with the reagent.

The temperature used in Step 5 can be, for example, from about 0° C. to about 100° C., about 15° C. to about 85° C., about 25° C. to about 75° C., about 35° C. to about 65° C., or from about 45° C. to about 55° C. In one non-limiting embodiment, the temperature is selected from about 45° C. to about 55° C.

The reaction can be allowed to proceed for a sufficient time to obtain the desired yield of product. For example, the reaction may proceed in Step 5 for about 1 to about 30 hours, about 3 to about 25 hours, about 6 to about 20 hours, about 9 to about 16 hours, or about 12 to about 15 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 6: Optional Deprotection of 2'-(alkylthio)-lactam-pyrrolo[2,3-d]pyrimidine

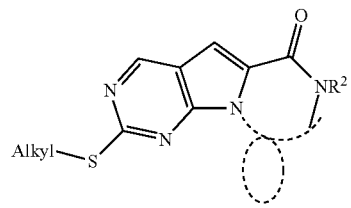

In Step 6 a 2'-(alkylthio)-lactam-pyrrolo[2,3-d]pyrimidine is deprotected to afford a deprotected alkyl 2-(alkylthio)-4-(lactam)pyrimidine-5-carboxylate. The 2'-(alkylthio)-lactam-pyrrolo[2,3-d]pyrimidine and deprotecting reagent are mixed in a suitable solvent, typically an organic solvent that both reactants dissolve in. Any molar ratio of the reactant and deprotecting reagent can be used that achieves the desired results. Typically a large molar excess of the deprotecting reagent is useful, for example about 5 equiv. of deprotecting reagent to about 1.0 equiv. of 2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford a deprotected 2'-(alkylthio)-lactam-pyrrolo[2,3-d]pyrimidine. In one non-limiting embodiment, the 2'-(alkylthio)-lactam-pyrrolo[2,3-d]pyrimidine is tert-butyl 2'-(methylthio)-6'-oxo-6'H-spiro[cyclohexane-1,9'-pyrazino[1',2':1,5]pyrrolo[2,3-d]pyrimidine]-7'(8'H)-carboxylate, the deprotecting reagent is TFA, the solvent is dichloromethane, the temperature is about 25° C., and the time is about 2 hours.

In one non-limiting embodiment, the 2'-(alkylthio)-lactam-pyrrolo[2,3-d]pyrimidine was already deprotected because it was suitable for the prior reactions in the absence of a protecting group. In an alternative embodiment, the protecting group is left on to be removed at a later step.

The deprotecting reagent used in Step 6 can be any suitable reagent that allows deprotection of any suitable protecting group, including but not limited to TFA, acetic acid, aminomethanesulfonic acid, ascorbic acid, benzene sulfonic acid, benzoic acid, formic acid, lactic acid, malic acid, malonic acid, methane sulfonic acid, oxalic acid, phthalic acid, salicyclic acid, succinic acid, sulfamic acid, p-toluenesulfonic acid, trichloroacetic acid, trifluoromethanesulfonic acid, boric acid, hydroiodic acid, hydrobromic acid, hydrochloric acid, hydrofluoric acid, iodic acid, nitric acid, perchloric acid, periodic acid, phosphinic acid, phosphoric acid, palladium on carbon with or without hydrogen gas, platinum on carbon with our without hydrogen gas, triethylsilane, TBAF, and HF. In one non-limiting embodiment, the protecting group is Boc and the suitable reagent is TFA. In an alternative embodiment, the protecting group is CBz and the suitable reagent is palladium on carbon with hydrogen gas.

In an additional embodiment the deprotecting reagent used in Step 6 is a basic deprotecting reagent, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0] non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, NaOH, tBuOK, NaH, KH, or Trizma. In one non-limiting embodiment, the base is selected from DIPEA, DMAP, DBU, DABCO, TEA, and tBuOK.

In an additional embodiment the deprotecting reagent used in Step 6 is NaOMe.

In another additional embodiment the deprotection uses MeOH as a solvent with NaOMe as a base. In one embodiment the reaction is heated for about 1, 2, 3, 4, 5, 6, 7, or 8 hours. In one embodiment the reaction is cooled below room temperature before isolation. In one embodiment the reaction is refluxed for about 3 hours, cooled to about 0° C., isolated, and washed with MeOH.

The solvent used in Step 6 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from TFA, DCM, THF, and chloroform. In an alternative embodiment, a mixture of solvents is used in Step 6. In another alternative embodiment, the deprotecting reagent is used as the solvent.

The temperature used in Step 6 can be, for example, from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 6 for about 1 to about 40 hours, about 3 to about 35 hours, about 5 to about 30 hours, about 10 to about 25 hours, or about 13 to about 20 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 7: Optional Oxidation of 2'-(alkylthio)-lactam-pyrrolo[2,3-d]pyrimidine

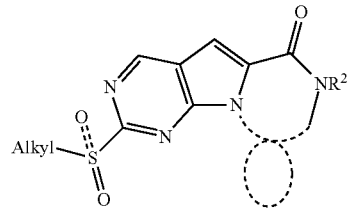

In Step 7 a 2'-(alkylthio)-lactam-pyrrolo[2,3-d]pyrimidine is reacted with an oxidant to afford an 2'-(alkylsulfonyl)-lactam-pyrrolo[2,3-d]pyrimidine or 2'-(alkylsulfinyl)-lactam-pyrrolo[2,3-d]pyrimidine. The 2'-(alkylthio)-lactam-pyrrolo[2,3-d]pyrimidine and oxidant are mixed in a suitable solvent, typically a neutral organic solvent that both reactants dissolve. Any molar ratio of the reactant and oxidant can be used that achieves the desired results. Typically, a large molar excess of the oxidant is useful, for example about 5 equiv. of oxidant to about 1.0 equiv. of 2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford either a 2'-(alkylsulfonyl)-lactam-pyrrolo[2,3-d]pyrimidine or 2'-(alkylsulfinyl)-lactam-pyrrolo[2,3-d]pyrimidine. In one non-limiting embodiment, the 2'-(alkylthio)-lactam-pyrrolo[2,3-d]pyrimidine is 2'-(methylthio)-7',8'-dihydro-6'H-spiro[cyclohexane-1,9'-pyrazino[1',2':1,5]pyrrolo[2,3-d]pyrimidin]-6'-one, the oxidant is oxone, the solvent is a mixture of water and acetonitrile, the temperature is about 25° C., and the time is about 2 hours.

The oxidant used in Step 7 can be any suitable reagent that allows oxidation to either the sulfone or sulfoxide oxidation state, including but not limited to oxone, hydrogen peroxide, mCPBA, sodium hypochlorite, and sodium chlorite. In one non-limiting embodiment, the product is a sulfone and the oxidant is oxone.

In an additional embodiment the oxidant used is catalyzed with an additive. In one embodiment the additive is $Na_2WO_4$. In one embodiment the additive is $Na_2WO_4$ and the oxidant is hydrogen peroxide. In one embodiment the additive is $Na_2WO_4$ and the oxidant is hydrogen peroxide and the reaction is conducted in a mixture of $H_2O$ and EtOH with heat. In one embodiment the additive is $Na_2WO_4$ and the oxidant is hydrogen peroxide and the reaction is conducted in a mixture of $H_2O$ and EtOH at about 60° C. for about 1, 2, 3, 4, 5, 6, 7, 8, or 9 hours.

In an additional embodiment the oxidant is added slowly to the reaction mixture. In one embodiment the oxidant is added over the course of about 10, 20, 30, 40, 50, 60, 70, 80, 90, or 100 minutes. In one embodiment the oxidant is added over the course of about 50 minutes. In one embodiment the addition over the course of 50 minutes results in a higher yield than a faster addition such as one over the course of 10 minutes.

The solvent used in Step 7 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from ACN, water, and dioxane. In an alternative embodiment, a mixture of solvents is used in Step 7, for example, water and ACN.

The temperature used in Step 7 can be, for example, from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 7 for about 1 to about 40 hours, about 3 to about 35 hours, about 5 to about 30 hours, about 10 to about 25 hours, or about 13 to about 20 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

It should be recognized by one skilled in the art, that the order of steps prescribed herein can be switched while still reaching the same final product. For example, the oxidation can be carried out in between Step 3 and Step 4, in between Step 4 and Step 5, or in between Step 5 and Step 6; the protection step can be carried out before Step 1, in between Step 3 and Step 4, or in between Step 4 and Step 5; the deprotection step can be carried out in between Step 3 and Step 4, in between Step 4 and Step 5, or after Step 7.

In one non-limiting embodiment, the lactam amine is already appropriately protected and Step 2 is not necessary. In another embodiment, the reagents and starting materials chosen do not need protection to proceed to the desired product, and Step 2 and Step 6 are not necessary.

In another embodiment, the lactam amine is a compound of Formula I, the alkyl 2-(alkylthio)-4-(lactam)pyrimidine-5-carboxylate is a compound of Formula II, the 5'-hydroxy-2'-(alkylthio)-lactam-pyrrolo[2,3-d]pyrimidine and 5'-leaving group-2'-(alkylthio)-lactam-pyrrolo[2,3-d]pyrimidine are compounds of Formula III, and the 2'-(alkylthio)-lactam-pyrrolo[2,3-d]pyrimidine is a compound of Formula IV.

IIIB. Process of Preparing Sulfone/Sulfoxide from Pyrimidine Aldehyde

It has been discovered that 2'-(alkylthio)-lactam-pyrrolo[2,3-d]pyrimidines and their sulfoxide and sulfide analogs as well can be prepared in five or fewer steps from 4-halo-2-(alkylthio)pyrimidine-5-carbaldehydes. In one non-limiting embodiment, the 2'-(alkylthio)-lactam-pyrrolo[2,3-d]pyrimidine is a spirocycle, for example, 2'-(methylsulfonyl)-7',8'-dihydro-6'H-spiro[cyclohexane-1,9'-pyrazino[1',2':1,5]pyrrolo[2,3-d]pyrimidin]-6'-one.

Step 1: Preparation of 2-(alkylthio)-4-(lactam)pyrimidine-5-carbaldehyde

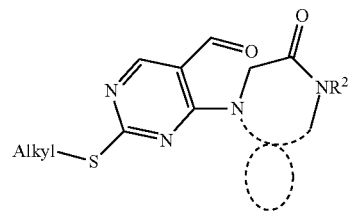

In Step 1 a 4-halo-2-(alkylthio)pyrimidine-5-carbaldehyde is reacted with a lactam amine in a nucleophilic substitution reaction to afford a 2-(alkylthio)-4-(lactam)pyrimidine-5-carbaldehyde. The 4-halo-2-(alkylthio)pyrimidine-5-carbaldehyde and lactam amine are mixed in a suitable solvent, typically a neutral organic solvent that both reactants dissolve in along with a base that will facilitate the nucleophilic substitution reaction. Any molar ratio of the two reactants can be used that achieves the desired results. Typically, a small molar excess of the lactam amine is useful, for example about 1.1 equiv. of lactam amine to about 1.0 equiv. of carbaldehyde. The reaction can be carried out at any temperature that allows the reaction to take place. It has been found that the reaction can be facilitated with heat, including up to reflux. The reaction is allowed sufficient time to provide the desired yield, after which the batch is optionally cooled and purified by any suitable means, including filtration, crystallization, and column chromatography, to afford a 2-(alkylthio)-4-(lactam)pyrimidine-5-carbaldehyde. In one non-limiting embodiment, the 4-halo-2-(alkylthio)pyrimidine-5-carbaldehyde is 4-chloro-2-(methylthio)pyrimidine-5-carbaldehyde, the lactam amine is a spirolactam, the base is DIPEA, the solvent is tert-butanol, the temperature is about 85° C., and the time is about 24 hours.

The base used in Step 1 can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, or Trizma. In one non-limiting embodiment, the base is selected from DIPEA, DMAP, DBU, TEA, and pyridine. In an alternative embodiment, multiple bases are used in Step 1.

The solvent used in Step 1 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DMAc, tert-butanol, DMAP, and DMSO. In an alternative embodiment, a mixture of solvents is used in Step 1.

In an additional embodiment the solvent used in Step 1 is dioxane. In another additional embodiment, the solvent is selected from DCM, EtOAc, ethanol, dioxane, tert-butyl alcohol, and THF.

The temperature used in Step 1 in non-limiting examples can be from about 50° C. to about 150° C., about 60° C. to about 125° C., about 70° C. to about 110° C., about 80° C. to about 100° C., or from about 90° C. to about 100° C. In one non-limiting embodiment, the temperature is selected from about 80° C. to about 100° C. In an alternative embodiment, the reaction temperature is higher than the solvent reflux by use of a reaction vessel that can maintain elevated pressures. Alternatively, while less typical, the reaction can be carried out at room temperature or below.

The reaction can be allowed to proceed for a sufficient time to obtain the desired yield of product. For example, the reaction may proceed in Step 1 for about 1 to about 65 hours, about 7 to about 55 hours, about 12 to about 45 hours, about 17 to about 35 hours, or about 22 to about 25 hours. It should be understood by those of skill in the art that the time and temperature of the reaction are related. For example, if a higher temperature is used a lower reaction time may obtain the desired yield.

Step 2: Optional Protection of
2-(alkylthio)-4-(lactam)pyrimidine-5-carbaldehyde

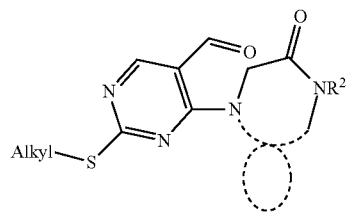

In Step 2 a 2-(alkylthio)-4-(lactam)pyrimidine-5-carbaldehyde is reacted with a protecting group reagent to afford a protected 2-(alkylthio)-4-(lactam)pyrimidine-5-carbaldehyde. The 2-(alkylthio)-4-(lactam)pyrimidine-5-carbaldehyde and protecting group reagent are mixed in a suitable solvent, typically a neutral organic solvent that both reactants dissolve in along with a base that will facilitate the installation of the protecting group. Any molar ratio of the two reactants can be used that achieves the desired results. Typically, a large molar excess of the protecting group reagent is useful, for example about 7 equiv. of protecting group reagent to about 1 equiv. of 2-(alkylthio)-4-(lactam) pyrimidine-5-carbaldehyde. The reaction can be carried out at any temperature that allows the reaction to take place. The reaction is allowed sufficient time to provide the desired yield, after which the batch is purified by any suitable means, including filtration, crystallization, and column chromatography, to afford a protected 2-(alkylthio)-4-(lactam) pyrimidine-5-carbaldehyde. In one non-limiting embodiment, the 2-(alkylthio)-4-(lactam)pyrimidine-5-carbaldehyde is 2-(methylthio)-4-(3-oxo-1,4-diazaspiro[5.5] undecan-1-yl)pyrimidine-5-carbaldehyde, the protecting group reagent is Boc-anhydride, the base is DMAP, the solvent is dichloromethane, the temperature is about 25° C., and the time is about 3 hours.

In one non-limiting embodiment, the initial lactam amine used was already protected. In an alternative embodiment, the lactam substituted pyrimidine reacts appropriately without needing a protecting group.

The protecting group reagent used in Step 2 can be any suitable reagent that allows installation of any suitable protecting group, including but not limited to Boc-anhydride, Boc-Cl, CBz-Cl, methyl chloroformate, benzyl chloride, benzoyl chloride, allylic chloride, triflic anhydride, Tf-Cl, tosyl anhydride, and Ts-Cl. In one non-limiting embodiment, the protecting group is Boc and the suitable reagent is either Boc-anhydride or Boc-Cl. In an alternative embodiment, the protecting group is CBz and the suitable reagent is CBz-Cl.

The base used in Step 2 can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0] non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, and Trizma. In one non-limiting embodiment, the base is selected from DIPEA, DMAP, DBU, TEA, and pyridine. In an alternative embodiment, multiple bases are used in Step 2.

The solvent used in Step 2 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 2.

The temperature used in Step 2 in non-limiting examples can be from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 2 for about 0.1 to about 20 hours, about 0.5 to about 15 hours, about 1 to about 10 hours, about 1.5 to about 5 hours, or about 2 to about 4 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 3: Preparation of 2'-(alkylthio)-lactam-pyrrolo[2,3-d]pyrimidine

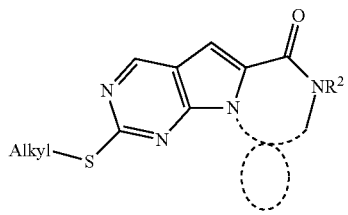

In Step 3 an optionally protected 2-(alkylthio)-4-(lactam) pyrimidine-5-carbaldehyde is reacted with a base in a intramolecular cyclization to afford a 2'-(alkylthio)-lactam-pyrrolo[2,3-d]pyrimidine. The protected alkyl 2-(alkylthio)-4-(lactam)pyrimidine-5-carbaldehyde and base are mixed in a suitable solvent, typically a neutral organic solvent that both the reactant and reagent dissolve in. Any molar ratio of the reactant and reagent can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford a 2'-(alkylthio)-lactam-pyrrolo[2,3-d]pyrimidine. In one non-limiting embodiment, the protected 2-(alkylthio)-4-(lactam) pyrimidine-5-carbaldehyde is tert-butyl 2'-(methylthio)-6'-oxo-6'H-spiro[cyclohexane-1,9'-pyrazino[1',2':1,5]pyrrolo[2,3-d]pyrimidine]-7'(8'H)-carboxylate, the base is tBuOK, the solvent is THF, the temperature is about 5° C., and the time is about 2 hours.

The base used in Step 3 can be any suitable base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, NaOH, tBuOK, NaH, KH, or Trizma. In one non-limiting embodiment, the base is selected from DIPEA, DMAP, DBU, DABCO, TEA, and tBuOK. In an alternative embodiment, multiple bases are used in Step 3.

The solvent used in Step 3 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 3.

The temperature used in Step 3 in non-limiting examples can be from about −50° C. to about 50° C., about −35° C. to about 40° C., about −10° C. to about 30° C., about −5° C. to about 20° C., or from about 0° C. to about 10° C. In one non-limiting embodiment, the temperature is selected from about 0° C. to about 10° C.

The reaction can be allowed to proceed for a sufficient time to obtain the desired yield of product. For example the reaction may proceed in Step 3 for about 0.1 to about 20 hours, for about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 4: Optional Deprotection of 2'-(alkylthio)-lactam-pyrrolo[2,3-d]pyrimidine

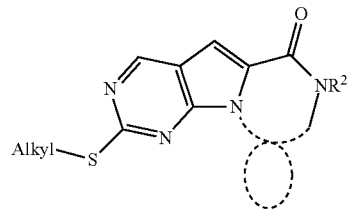

In Step 4 a 2'-(alkylthio)-lactam-pyrrolo[2,3-d]pyrimidine is deprotected to afford a deprotected 2'-(alkylthio)-lactam-pyrrolo[2,3-d]pyrimidine. The protected 2'-(alkylthio)-lactam-pyrrolo[2,3-d]pyrimidine and deprotecting reagent are mixed in a suitable solvent, typically an organic solvent that both reactants dissolve in. Any molar ratio of the reactant and deprotecting reagent can be used that achieves the desired results. Typically a large molar excess of the deprotecting reagent is useful, for example about 5 equiv. of deprotecting reagent to about 1.0 equiv. of 2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford a deprotected 2'-(alkylthio)-lactam-pyrrolo[2,3-d]pyrimidine. In one non-limiting embodiment, the protected 2'-(alkylthio)-lactam-pyrrolo[2,3-d]pyrimidine is tert-butyl 2'-(methylthio)-6'-oxo-6'H-spiro[cyclohexane-1,9'-pyrazino[1',2':1,5]pyrrolo[2,3-d]pyrimidine]-7'(8'H)-carboxylate, the deprotecting reagent is hydrochloric acid, the solvent is water, the temperature is about 25° C., and the time is about 2 hours.

In one non-limiting embodiment, the 2'-(alkylthio)-lactam-pyrrolo[2,3-d]pyrimidine was already unprotected because it was suitable for the prior reactions in the absence of a protecting group. In an alternative embodiment, the protecting group is left on to be removed at a later step.

The deprotecting reagent used in Step 4 can be any suitable reagent that allows deprotection of any suitable protecting group, including but not limited to TFA, acetic acid, aminomethanesulfonic acid, ascorbic acid, benzene sulfonic acid, benzoic acid, formic acid, lactic acid, malic acid, malonic acid, methane sulfonic acid, oxalic acid, phthalic acid, salicyclic acid, succinic acid, sulfamic acid, p-toluenesulfonic acid, trichloroacetic acid, trifluoromethanesulfonic acid, boric acid, hydroiodic acid, hydrobromic acid, hydrochloric acid, hydrofluoric acid, iodic acid, nitric acid, perchloric acid, periodic acid, phosphinic acid, phosphoric acid, palladium on carbon with or without hydrogen gas, platinum on carbon with our without hydrogen gas, triethylsilane, TBAF, and HF. In one non-limiting embodiment, the protecting group is Boc and the suitable reagent is hydrochloric acid. In an alternative embodiment, the protecting group is CBz and the suitable reagent is palladium on carbon with hydrogen gas.

The solvent used in Step 4 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, and water. In an alternative embodiment, a mixture of solvents is used in Step 4. In another alternative embodiment, the deprotecting reagent is used as the solvent.

The temperature used in Step 4 in non-limiting examples can be from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 4 for about 1 to about 40 hours, about 3 to about 35 hours, about 5 to about 30 hours, about 10 to about 25 hours, or about 13 to about 20 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 5: Optional Oxidation of 2'-(alkylthio)-lactam-pyrrolo[2,3-d]pyrimidine

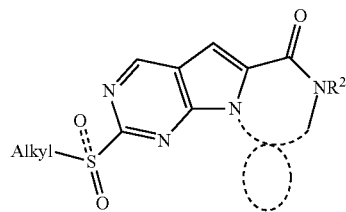

In Step 5 a 2'-(alkylthio)-lactam-pyrrolo[2,3-d]pyrimidine is reacted with an oxidant to afford a 2'-(alkylsulfonyl)-lactam-pyrrolo[2,3-d]pyrimidine or 2'-(alkylsulfinyl)-lactam-pyrrolo[2,3-d]pyrimidine. The 2'-(alkylthio)-lactam-pyrrolo[2,3-d]pyrimidine and oxidant are mixed in a suitable solvent, typically a neutral organic solvent that both reactants dissolve in. Any molar ratio of the reactant and oxidant can be used that achieves the desired results. Typically, a large molar excess of the oxidant is useful, for example about 5 equiv. of oxidant to about 1.0 equiv. of 2'-(alkylthio)-lactam-pyrrolo[2,3-d]pyrimidine. The reaction can be carried out at any temperature that allows the reaction to take place. The reaction is allowed sufficient time to provide the desired yield, after which the batch is purified by any suitable means, including filtration, crystallization, and column chromatography, to afford either a 2'-(alkylsulfonyl)-lactam-pyrrolo[2,3-d]pyrimidine or 2'-(alkylsulfinyl)-lactam-pyrrolo[2,3-d]pyrimidine. In one non-limiting embodiment, the 2'-(alkylthio)-lactam-pyrrolo[2,3-d]pyrimidine is 2'-(methylthio)-7',8'-dihydro-6'H-spiro[cyclohexane-1,9'-pyrazino[1',2':1,5]pyrrolo[2,3-d]pyrimidin]-6'-one, the oxidant is oxone, the solvent is a mixture of water and acetonitrile, the temperature is about 25° C., and the time is about 2 hours.

The oxidant used in Step 5 can be any suitable reagent that allows oxidation to either the sulfone or sulfoxide oxidation state, including but not limited to oxone, hydrogen peroxide, mCPBA, sodium hypochlorite, and sodium chlorite. In one non-limiting embodiment, the product is a sulfone and the oxidant is oxone.

The solvent used in Step 5 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from ACN, water, and dioxane. In an alternative embodiment, a mixture of solvents is used in Step 5, for example, water and ACN.

The temperature used in Step 5 in non-limiting examples can be from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 5 for about 1 to about 40 hours, about 3 to about 35 hours, about 5 to about 30 hours, about 10 to about 25 hours, or about 13 to about 20 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

It should be recognized by one skilled in the art, that the order of steps prescribed herein can be switched while still reaching the same final product.

In one non-limiting embodiment, the lactam amine is already appropriately protected and Step 2 is not necessary. In another embodiment, the reagents and starting materials chosen do not need protection to proceed to the desired product, and Step 2 and Step 4 are not necessary.

In another embodiment, the lactam amine is a compound of Formula I, the 2-(alkylthio)-4-(lactam)pyrimidine-5-carbaldehyde is a compound of Formula II, and the 2'-(alkylthio)-lactam-pyrrolo[2,3-d]pyrimidine is a compound of Formula IV.

IIIC. Process of Preparing 1,4-diazaspiro[5.5]undecan-3-ones from cyclohexanone It has been discovered that 1,4-diazaspiro[5.5]undecan-3-ones can be prepared from cyclohexanones. In one non-limiting embodiment, the 1,4-diazaspiro[5.5]undecan-3-one is initially unprotected and optionally protected during later synthetic steps.

Step 1: Preparation of alkyl (1-cyanocyclohexyl)glycinate

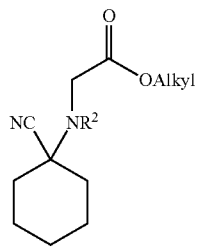

In Step 1 an appropriately substituted alkyl glycinate or salt thereof is reacted with a cyclohexanone in the presence of TMSCN to afford an alkyl (1-cyanocyclohexyl)glycinate. Cyclohexanone and alkyl glycinate are mixed in a suitable solvent, typically a neutral organic solvent that both reactants dissolve in along with a base that will facilitate the reaction. TMSCN is then added slowly to the mixture. Any molar ratio of the two reactants can be used that achieves the desired results. The reaction can be carried out at any temperature that allows the reaction to take place. Due to the exothermic nature of the reaction the temperature is controlled on large scale. The reaction is allowed sufficient time to provide the desired yield, after which the batch is purified by any suitable means, including filtration, crystallization, and column chromatography, to afford an alkyl (1-cyanocyclohexyl)glycinate. In one non-limiting embodiment, the alkyl glycinate is methyl glycinate or a salt thereof, the base is TEA, the solvent is DCM, the temperature is about 35° C. or less, and the time is about 4 hours.

The base used in Step 1 can be any suitable base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, NaOH, tBuOK, NaH, KH, potassium carbonate, or Trizma. In one non-limiting embodiment, the base is selected from DIPEA, TEA, DBU, DABCO, potassium carbonate, and tBuOK. In an alternative embodiment, multiple bases are used in Step 1.

The solvent used in Step 1 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from TEA, ACN, DCM, and DMSO. In an alternative embodiment, a mixture of solvents is used in Step 1.

In an additional embodiment the solvent used in Step 1 is dioxane. In another additional embodiment, the solvent is selected from DCM, EtOAc, ethanol, dioxane, tert-butyl alcohol, and THF.

The temperature used in Step 1 in non-limiting examples can be from about −20° C. to about 50° C., about −10° C. to about 40° C., about 0° C. to about 35° C., or about 10° C. to about 30° C. In one non-limiting embodiment, the temperature is selected from about 10° C. to about 30° C.

The reaction can be allowed to proceed for a sufficient time to obtain the desired yield of product. It should be understood by those of skill in the art that the time and temperature of the reaction are related. For example, if a higher temperature is used a lower reaction time may obtain the desired yield.

Step 2: Preparation of 4-diazaspiro[5.5]undecan-3-one

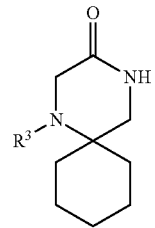

In Step 2 an alkyl (1-cyanocyclohexyl)glycinate or salt thereof is reduced by a hydride source and suitable catalyst, and subsequently undergoes an intramolecular cyclization to afford a 4-diazaspiro[5.5]undecan-3-one. The alkyl (1-cyanocyclohexyl)glycinate is dissolved in a suitable solvent. Then a reductant is added optionally in the presence of a catalyst to afford reduction of the cyano group to an amine. The amine then acts as a nucleophile in a subsequent intramolecular cyclization to afford a 4-diazaspiro[5.5]undecan-3-one. The reaction can be carried out at any temperature that allows the reaction to take place. The reaction is allowed sufficient time to provide the desired yield, after which the batch is purified by any suitable means, including filtration, crystallization, and column chromatography, to afford a 4-diazaspiro[5.5]undecan-3-one. In one non-limiting embodiment, the alkyl (1-cyanocyclohexyl)glycinate is methyl (1-cyanocyclohexyl)glycinate or a salt thereof, the solvent is MeOH, the hydride source is hydrogen gas, the catalyst is platinum oxide, the temperature is about 40° C., and the time is about 3 hours.

The hydride source used in Step 2 can be any suitable hydride source, including but not limited to sodium triacetoxyborohydride, hydrogen gas, sodium borohydride, cyanoborohydride, and ammonia formate. In an alternative embodiment, the hydride source is used stoichiometrically with no catalyst, for example sodium triacetoxyborohydride without platinum on carbon.

The solvent used in Step 2 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from methanol, water, and ethanol. In an alternative embodiment, a mixture of solvents is used in Step 2.

The temperature used in Step 2 in non-limiting examples can be from about −10° C. to about 90° C., about 0° C. to about 80° C., about 10° C. to about 70° C., about 20° C. to about 60° C., or from about 30° C. to about 50° C. In one non-limiting embodiment, the temperature is selected from about 30° C. to about 50° C.

The reaction can be allowed to proceed for a sufficient time to obtain the desired yield of product. For example, the reaction may proceed in Step 2 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

IIID. Process of Preparing 1,4-diazaspiro[5.5]undecan-3-ones from alkyl 2-oxoacetate It has been discovered that 1,4-diazaspiro[5.5]undecan-3-ones can be prepared from alkyl 2-oxoacetate and 1-(aminomethyl)cyclohexan-1-amine which may be optionally protected. In one non-limiting embodiment, the 1,4-diazaspiro[5.5]undecan-3-one is a protected, for example, tert-butyl 3-oxo-1,4-diazaspiro[5.5]undecane-4-carboxylate.

Step 1: Preparation of alkyl (1-(aminomethyl)cyclohexyl)glycinate

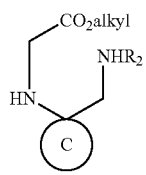

In Step 1 a 1-(aminomethyl)cyclohexan-1-amine is reacted with an alkyl 2-oxoacetate in a reductive amination reaction to afford an alkyl (1-(aminomethyl)cyclohexyl) glycinate. The 1-(aminomethyl)cyclohexan-1-amine and alkyl 2-oxoacetate are mixed in a suitable solvent, typically a neutral organic solvent that both reactants dissolve in along with a catalyst and hydride source that will facilitate the reductive amination reaction. Any molar ratio of the two reactants can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford an alkyl (1-(aminomethyl)cyclohexyl)glycinate. In one non-limiting embodiment, the 1-(aminomethyl)cyclohexan-1-amine is tert-butyl ((1-aminocyclohexyl)methyl)carbamate, the alkyl 2-oxoacetate is ethyl 2-oxoacetate, the catalyst is platinum on carbon, the hydride source is hydrogen gas, the solvent is DCM, the temperature is about 25° C., and the time is about 24 hours.

The hydride source used in Step 1 can be any suitable hydride source, including but not limited to sodium triacetoxyborohydride, hydrogen gas, sodium borohydride, cyanoborohydride, and ammonia formate. In an alternative embodiment, the hydride source is used stoichiometrically with no catalyst, for example sodium triacetoxyborohydride without platinum on carbon.

The solvent used in Step 1 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, EtOAc, ethanol, tert-butyl alcohol and THF. In an alternative embodiment, a mixture of solvents is used in Step 1.

In an additional embodiment the solvent used in Step 1 is dioxane. In another additional embodiment, the solvent is selected from DCM, EtOAc, ethanol, dioxane, tert-butyl alcohol, and THF.

The temperature used in Step 1 in non-limiting examples can be from about −50° C. to about 50° C., about −35 to about 40° C., about −10° C. to about 30° C., about −5° C. to about 20° C., or from about 0° C. to about 10° C. In one non-limiting embodiment, the temperature is selected from about 0° C. to about 10° C.

The reaction can be allowed to proceed for a sufficient time to obtain the desired yield of product. For example, the reaction may proceed in Step 1 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 2: Optional Deprotection of alkyl (1-(aminomethyl)cyclohexyl)glycinate

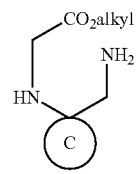

In Step 2 an alkyl (1-(aminomethyl)cyclohexyl)glycinate is deprotected to afford a deprotected alkyl (1-(aminomethyl)cyclohexyl)glycinate. The alkyl (1-(aminomethyl)cyclohexyl)glycinate and deprotecting reagent are mixed in a suitable solvent, typically a solvent that both reactants dissolve in. Any molar ratio of the reactant and deprotecting reagent can be used that achieves the desired results. Typically a large molar excess of the deprotecting reagent is useful, for example about 5 equiv. of deprotecting reagent to about 1.0 equiv. of protected alkyl (1-(aminomethyl)cyclohexyl)glycinate. The reaction can be carried out at any temperature that allows the reaction to take place. The reaction is allowed sufficient time to provide the desired yield, after which the batch is purified by any suitable means, including filtration, crystallization, and column chromatography, to afford a deprotected alkyl (1-(aminomethyl) cyclohexyl)glycinate. In one non-limiting embodiment, the protected alkyl (1-(aminomethyl)cyclohexyl)glycinate is ethyl (1-(((tert-butoxycarbonyl)amino)methyl)cyclohexyl) glycinate, the deprotecting reagent is hydrochloric acid, the solvent is water, the temperature is about 25° C., and the time is about 2 hours.

In one non-limiting embodiment, the alkyl (1-(aminomethyl)cyclohexyl)glycinate was already deprotected because it was suitable for the prior reaction in the absence of a protecting group. In an alternative embodiment, the protecting group is left on to be removed at a later step.

The deprotecting reagent used in Step 2 can be any suitable reagent that allows deprotection of any suitable protecting group, including but not limited to TFA, acetic acid, aminomethanesulfonic acid, ascorbic acid, benzene sulfonic acid, benzoic acid, formic acid, lactic acid, malic acid, malonic acid, methane sulfonic acid, oxalic acid, phthalic acid, salicyclic acid, succinic acid, sulfamic acid, p-toluenesulfonic acid, trichloroacetic acid, trifluoromethanesulfonic acid, boric acid, hydroiodic acid, hydrobromic acid, hydrochloric acid, hydrofluoric acid, iodic acid, nitric acid, perchloric acid, periodic acid, phosphinic acid, phosphoric acid, palladium on carbon with or without hydrogen gas, platinum on carbon with our without hydrogen gas, triethylsilane, TBAF, and HF. In one non-limiting embodiment, the protecting group is Boc and the suitable reagent is hydrochloric acid. In an alternative embodiment, the protecting group is CBz and the suitable reagent is palladium on carbon with hydrogen gas.

The solvent used in Step 2 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, and water. In an alternative embodiment, a mixture of solvents is used in Step 2. In another alternative embodiment, the deprotecting reagent is used as the solvent.

The temperature used in Step 2 in non-limiting examples can be from about −20° C. to about 100° C., about −10° C. to about 80° C., about 0° C. to about 60° C., about 10° C. to about 40° C., or from about 20° C. to about 30° C. In one non-limiting embodiment, the temperature is selected from about 20° C. to about 30° C.

The reaction can be allowed to proceed for a sufficient time to obtain the desired yield of product. For example, the reaction may proceed in Step 2 in about 1 to about 40 hours, in about 3 to about 35 hours, in about 5 to about 30 hours, in about 10 to about 25 hours, or in about 13 to about 20 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 3: Preparation of
4-diazaspiro[5.5]undecan-3-one

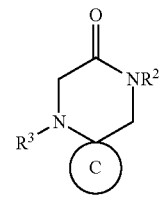

In Step 3 an alkyl (1-(aminomethyl)cyclohexyl)glycinate is reacted with a base in a intramolecular cyclization to afford a 4-diazaspiro[5.5]undecan-3-ones. The alkyl (1-(aminomethyl)cyclohexyl)glycinate and base are mixed in a suitable solvent, typically a neutral organic solvent that both the reactant and reagent dissolve in. Any molar ratio of the reactant and reagent can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford a 4-diazaspiro[5.5]undecan-3-one. In one non-limiting embodiment, the alkyl (1-(aminomethyl)cyclohexyl)glycinate is ethyl (1-(aminomethyl)cyclohexyl)glycinate, the solvent is THF, the temperature is about 5° C., and the time is about 2 hours.

The base used in Step 3 can be any suitable base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0] non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, NaOH, tBuOK, NaH, KH, or Trizma. In one non-limiting embodiment, the base is selected from DIPEA, DMAP, DBU, DABCO, TEA, and tBuOK. In an alternative embodiment, multiple bases are used in Step 3.

The solvent used in Step 3 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 3.

The temperature used in Step 3 in non-limiting examples can be from about −50° C. to about 50° C., about −35 to about 40° C., about −10° C. to about 30° C., about −5° C.

to about 20° C., or from about 0° C. to about 10° C. In one non-limiting embodiment, the temperature is selected from about 0° C. to about 10° C.

The reaction can be allowed to proceed for a sufficient time to obtain the desired yield of product. For example, the reaction may proceed in Step 3 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

IIID. Alternative Process of Preparing 1,4-diazaspiro[5.5]undecan-3-ones from cyclohexanone In an additional embodiment 1,4-diazaspiro[5.5]undecan-3-ones can be prepared from cyclohexanone utilizing a cyano intermediate.

Step 1: Preparation of 1-aminocycloalkyl-1-carbonitrile

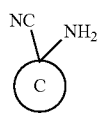

In Step 1 a cyclic ketone is reacted with a source of cyanide and ammonia and optionally additional reagents or catalysts to afford a 1-aminocycloalkyl-1-carbonitrile. The cyclic ketone, cyanide source, and ammonia source are mixed in a suitable solvent, typically a neutral organic solvent that both reactants dissolve in. Any molar ratio of the two reactants can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford a 1-aminocycloalkyl-1-carbonitrile. In one non-limiting embodiment, the cyclic ketone is cyclohexanone, the cyanide source is TMSCN, the ammonia source is ammonia, 1-aminocycloalkyl-1-carbonitrile is 1-(aminomethyl)cyclohexan-1-amine, and the catalyst is titanium isopropoxide. In one embodiment centrifugation is used in the isolation of the 1-aminocycloalkyl-1-carbonitrile. In another embodiment Celite filtration is used in the isolation of the 1-aminocycloalkyl-1-carbonitrile.

The solvent used in Step 1 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, EtOAc, ethanol, tert-butyl alcohol and THF. In an alternative embodiment, a mixture of solvents is used. In one embodiment no solvent is used.

In an additional embodiment the solvent used in Step 1 is dioxane. In another additional embodiment, the solvent is selected from DCM, EtOAc, ethanol, dioxane, tert-butyl alcohol, and THF.

The reaction can be allowed to proceed for a sufficient time to obtain the desired yield of product. For example, the reaction may proceed in Step 1 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 2: Preparation of 1-(aminomethyl)cycloalkyl-1-amine

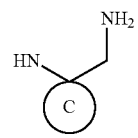

In Step 2 1-aminocycloalkyl-1-carbonitrile is reduced to afford a 1-(aminomethyl)cycloalkyl-1-amine. The 1-aminocycloalkyl-1-carbonitrile and a reducing reagent are mixed in a suitable solvent, typically a solvent that both reactants dissolve in. Any molar ratio of the reactant and reducing reagent can be used that achieves the desired results. Typically a molar excess of the reducing reagent is useful, for example about 2 equiv. of reducing reagent to about 1.0 equiv. of 1-aminocycloalkyl-1-carbonitrile. The reaction can be carried out at any temperature that allows the reaction to take place. The reaction is allowed sufficient time to provide the desired yield, after which the batch is purified by any suitable means, including filtration, crystallization, and column chromatography, to afford 1-(aminomethyl)cycloalkyl-1-amine. In one non-limiting embodiment, the 1-aminocycloalkyl-1-carbonitrile is 1-(aminomethyl)cyclohexan-1-amine, the reducing reagent is lithium aluminium hydride (LAH), the temperature is about 45° C., and the time is about 30 minutes.

The reducing reagent used in Step 2 can be any suitable reagent that allows reduction of the cyano group, including but not limited to LAH, $BH_3$-THF, $BH_3SMe_2$, $H_2$, $H_2$ with Raney Nickel, and $H_2$ with Pd/C.

The solvent used in Step 2 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, and water. In an alternative embodiment, a mixture of solvents is used in Step 2.

The temperature used in Step 2 in non-limiting examples can be from about −20° C. to about 100° C., about −10° C. to about 90° C., about 0° C. to about 80° C., about 10° C. to about 70° C., or from about 20° C. to about 60° C. In one non-limiting embodiment, the temperature is selected from about 30° C. to about 50° C.

The reaction can be allowed to proceed for a sufficient time to obtain the desired yield of product. For example, the reaction may proceed in Step 2 in about 10 minutes to about 3 hours, in about 10 minutes to about 2 hours, in about 10 minutes to about 1 hour, in about 10 to about 50 minutes, or in about 20 to about 40 minutes. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 3: Preparation of Protected 1-(aminomethyl)cycloalkyl-1-amine

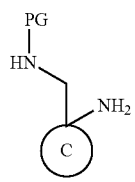

In Step 3 a 1-(aminomethyl)cycloalkyl-1-amine is reacted with a protecting group reagent afford a protected 1-(aminomethyl)cycloalkyl-1-amine. The 1-(aminomethyl)cycloalkyl-1-amine and protecting group reagent are mixed in a suitable solvent, typically a neutral organic solvent that both reactants dissolve in along with a base that will facilitate the installation of the protecting group. Any molar ratio of the two reactants can be used that achieves the desired results. Typically a molar deficiency or equivalence of the protecting group reagent is useful, for example about 0.6, 0.7, 0.8, 0.9, 1, or 1.1 equiv. of protecting group reagent to about 1 equiv. of 1-(aminomethyl)cycloalkyl-1-amine. The reaction can be carried out at any temperature that allows the reaction to take place. The reaction is allowed sufficient time to provide the desired yield, after which the batch is purified by any suitable means, including filtration, crystallization, and column chromatography, to afford a protected 1-(aminomethyl)cycloalkyl-1-amine. In one non-limiting embodiment, the 1-(aminomethyl)cycloalkyl-1-amine is 1-(aminomethyl)cyclohexan-1-amine, the protecting group reagent is Boc-anhydride, the protected 1-(aminomethyl)cycloalkyl-1-amine is tert-butyl ((1-aminocyclohexyl)methyl)carbamate, no base is used, and the temperature is about-70° C.

The protecting group reagent used in Step 3 can be any suitable reagent that allows installation of any suitable protecting group, including but not limited to Boc-anhydride, Boc-Cl, CBz-Cl, methyl chloroformate, benzyl chloride, benzoyl chloride, allylic chloride, triflic anhydride, Tf-Cl, tosyl anhydride, and Ts-Cl. In one non-limiting embodiment, the protecting group is Boc and the suitable reagent is either Boc-anhydride or Boc-Cl. In an alternative embodiment, the protecting group is CBz and the suitable reagent is CBz-Cl.

In one embodiment Step 3 is conducted without the addition of a base. If a base is used the base can be any suitable organic base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, and Trizma.

The solvent used in Step 3 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, dioxane, water, and THF. In an alternative embodiment, a mixture of solvents is used in Step 3.

The temperature used in Step 3 in non-limiting examples can be from about −100° C. to about 20° C., about −90° C. to about 0° C., about −80° C. to about −10° C., about −80° C. to about −40° C., or from about −80° C. to about −60° C. In one non-limiting embodiment, the temperature is selected from about −80° C. to about −60° C.

The reaction can be allowed to proceed for a sufficient time to obtain the desired yield of product. For example, the reaction may proceed in Step 3 for about 0.1 to about 20 hours, about 0.5 to about 15 hours, about 1 to about 10 hours, about 1.5 to about 5 hours, or about 2 to about 4 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 4: Preparation of alkyl (1-(((protecting group)amino)methyl)cycloalkyl)glycinate

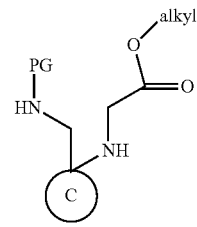

In Step 4 a protected 1-(aminomethyl)cycloalkyl-1-amine is reacted with a base, and alkyl 2-bromoacetate to afford an alkyl (1-(((protecting group)amino)methyl)cycloalkyl) glycinate. The protected 1-(aminomethyl)cycloalkyl-1-amine and base are mixed in a suitable solvent, typically a neutral organic solvent that both the reactant and reagent dissolve in. Any molar ratio of the reactant and reagent can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford an alkyl (1-(((protecting group)amino)methyl)cycloalkyl)glycinate. In one non-limiting embodiment, the protected 1-(aminomethyl)cycloalkyl-1-amine is tert-butyl ((1-aminocyclohexyl)methyl)carbamate, the solvent is acetonitrile, the base is K₂CO₃, and the alkyl (1-(((protecting group)amino)methyl)cycloalkyl) glycinate is methyl (1-(((tert-butoxycarbonyl)amino) methyl)cyclohexyl)glycinate.

The base used in Step 4 can be any suitable base, including but not limited to DIPEA, DMAP, DBU, TEA, pyridine, ammonia, methylamine, ethylamine, propylamine, isopropylamine, dimethylamine, diethylamine, dipropylamine, diisopropylamine, trimethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0] non-5-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, NaOH, tBuOK, NaH, KH, or Trizma. In one non-limiting embodiment, the base is selected from K₂CO₃, Na₂CO₃, and MgCO₃. In an alternative embodiment, multiple bases are used in Step 4.

The solvent used in Step 4 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from acetonitrile, dioxane, water, and THF. In an alternative embodiment, a mixture of solvents is used in Step 4.

The temperature used in Step 3 in non-limiting examples can be from about 0° C. to about 100° C., about 0 to about 90° C., about 0° C. to about 80° C., about 20° C. to about 80° C., or from about 30° C. to about 80° C.

The reaction can be allowed to proceed for a sufficient time to obtain the desired yield of product. For example, the reaction may proceed in Step 4 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

Step 5: Preparation of
4-diazaspiro[5.5]undecan-3-one

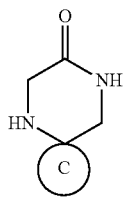

In Step 5 an alkyl (1-(((protecting group)amino)methyl) cycloalkyl)glycinate is deprotected with a deprotecting reagent and then treated with an acid to cause an intramolecular cyclization to afford a 4-diazaspiro[5.5]undecan-3-one. The alkyl (1-(((protecting group)amino)methyl)cycloalkyl)glycinate and deprotecting reagent are mixed in a suitable solvent, typically a solvent that both the reactant and reagent dissolve in. Any molar ratio of the reactant and reagent can be used that achieves the desired results. The reaction can be carried out at any temperature that allows the reaction to take place. The reaction is allowed sufficient time to provide the desired yield, after which the batch is purified by any suitable means, including filtration, crystallization, and column chromatography, to afford a 4-diazaspiro[5.5] undecan-3-one. In one non-limiting embodiment, the alkyl (1-(((protecting group)amino)methyl)cycloalkyl)glycinate is methyl (1-(((tert-butoxycarbonyl)amino)methyl)cyclohexyl)glycinate, the solvent is DCE, the acid is TFA, the deprotecting agent is TFA, the temperature is about reflux, and the 4-diazaspiro[5.5]undecan-3-one is 1,4-diazaspiro [5.5]undecan-3-one.

The deprotecting reagent used in Step 5 can be any suitable reagent that allows deprotection of any suitable protecting group, including but not limited to TFA, acetic acid, aminomethanesulfonic acid, ascorbic acid, benzene sulfonic acid, benzoic acid, formic acid, lactic acid, malic acid, malonic acid, methane sulfonic acid, oxalic acid, phthalic acid, salicyclic acid, succinic acid, sulfamic acid, p-toluenesulfonic acid, trichloroacetic acid, trifluoromethanesulfonic acid, boric acid, hydroiodic acid, hydrobromic acid, hydrochloric acid, hydrofluoric acid, iodic acid, nitric acid, perchloric acid, periodic acid, phosphinic acid, phosphoric acid, palladium on carbon with or without hydrogen gas, platinum on carbon with our without hydrogen gas, triethylsilane, TBAF, and HF. In one non-limiting embodiment, the protecting group is Boc and the suitable reagent is hydrochloric acid. In an alternative embodiment, the protecting group is CBz and the suitable reagent is palladium on carbon with hydrogen gas.

The acid used in Step 5 can be any suitable acid that allows intramolecular cyclization, including but not limited to TFA, acetic acid, aminomethanesulfonic acid, ascorbic acid, benzene sulfonic acid, benzoic acid, formic acid, lactic acid, malic acid, malonic acid, methane sulfonic acid, oxalic acid, phthalic acid, salicyclic acid, succinic acid, sulfamic acid, p-toluenesulfonic acid, trichloroacetic acid, trifluoromethanesulfonic acid, boric acid, hydroiodic acid, hydrobromic acid, hydrochloric acid, hydrofluoric acid, iodic acid, nitric acid, perchloric acid, periodic acid, phosphinic acid, and phosphoric acid. In one non-limiting embodiment the acid is TFA.

The solvent used in Step 5 can be any suitable organic solvent, including but not limited to DMAc, DCM, THF, DMF, TFA, ACN, DMAP, water, acetic acid, acetone, dioxane, benzene, 1-butanol, 2-butanol, tert-butyl alcohol, carbon tetrachloride, chloroform, cyclohexane, hexanes, diethyl ether, diglyme, DME, DMSO, ethanol, ethyl acetate, ethylene glycol, glycerin, heptane, HMPA, methanol, MTBE, NMP, pentane, pyridine, toluene, hydrochloric acid, and triethyl amine. In one non-limiting embodiment, the solvent is selected from DCM, DCE, TFA, and THF. In an alternative embodiment, a mixture of solvents is used in Step 5.

The temperature used in Step 5 in non-limiting examples can be from about 30° C. to about 100° C., about 35 to about 90° C., about 50° C. to about 85° C., about 55° C. to about 85° C., or from about 60° C. to about 85° C.

The reaction can be allowed to proceed for a sufficient time to obtain the desired yield of product. For example, the reaction may proceed in Step 5 in about 0.1 to about 20 hours, in about 0.5 to about 15 hours, in about 1 to about 10 hours, in about 1.5 to about 5 hours, or in about 2 to about 3 hours. It should be understood by those of skill in the art that the time and temperature of the reaction are related. For example, if a higher temperature is used a lower reaction time may obtain the desired yield. Alternatively, if a lower temperature is used a higher reaction time will be necessary to obtain the desired yield, but fewer byproducts may be present.

In one embodiment the 4-diazaspiro[5.5]undecan-3-one is isolated as a salt. In another embodiment, the 4-diazaspiro[5.5]undecan-3-one is isolated as a free-base.

In one embodiment, the 4-diazaspiro[5.5]undecan-3-one salt is dissolved or suspended in a solvent and is then subjected to a base. In one embodiment the solvent is ethanol. In one embodiment the solvent is DCM. In one embodiment the base is K$_2$CO$_3$. In one embodiment the solvent is ethanol and the base is K$_2$CO$_3$. In one embodiment the solvent is DCM and the base is K$_2$CO$_3$.

IV. New Intermediates

In one non-limiting embodiment, a number of the compounds used in the process of preparation described herein are new. Some of these are described below.

In one embodiment, a compound of Formula II is provided:

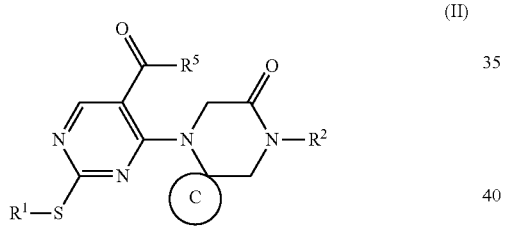

(II)

as well as salts thereof. Formula II is a heteroaryl bonded to a spirocyclic lactam.

Non-limiting examples of compounds falling within Formula II are illustrated below. This disclosure includes all combinations of these definitions so long as a stable compound results.

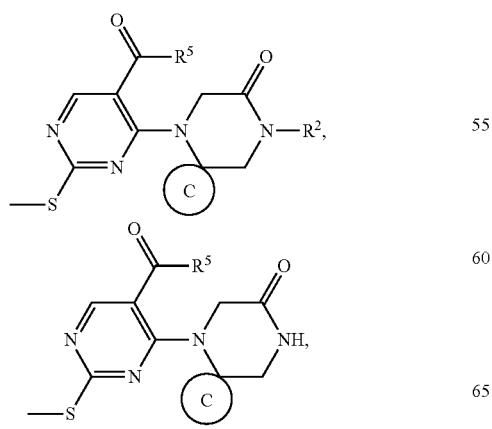

-continued

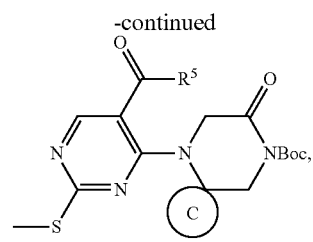

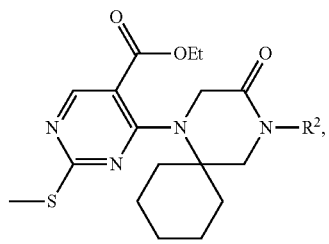

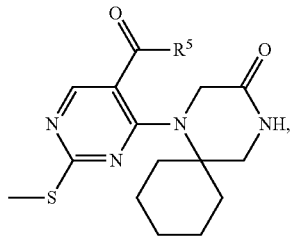

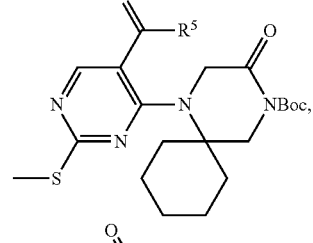

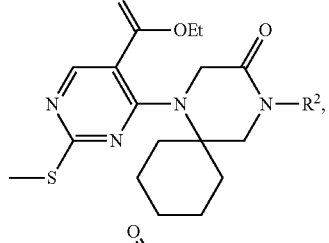

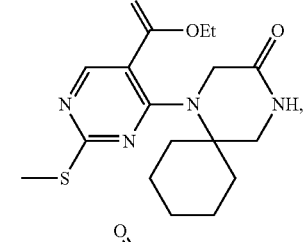

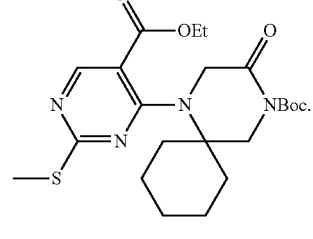

In one aspect this disclosure includes compounds and salts of Formula IIA:

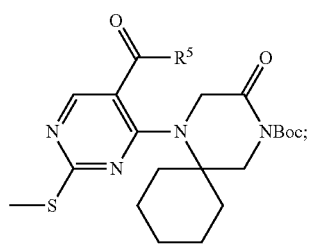
(IIA)

wherein R⁵ is as defined herein. Non-limiting examples of R⁵ are hydrogen, bromine, chlorine, fluorine, iodine, —CF₃, —OEt, —OMe, —NCH₃OMe, and —OC(O)CH₃.

In one aspect this disclosure includes compounds and salts of Formula IIB:

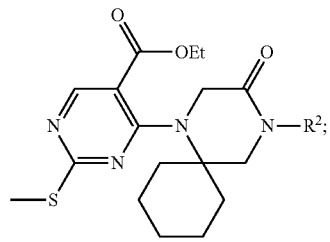
(IIB)

wherein R² is as defined herein. Non-limiting examples of R² are hydrogen, -Boc, -CBz, -Bn, methyl carbamate, and methyl.

In one aspect this disclosure includes compounds and salts of Formula IIC:

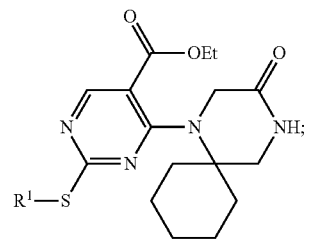
(IIC)

wherein R¹ is as defined herein. Non-limiting examples of R¹ are methyl, —CF₃, -Bn, -Ph, -Et, propyl, and isopropyl.

In one aspect this disclosure includes compounds and salts of Formula IID:

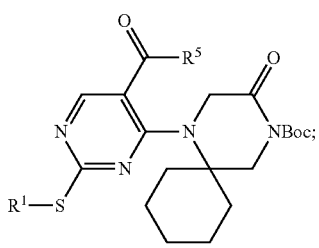
(IID)

wherein R¹ is as defined herein. Non-limiting examples of R¹ are methyl, —CF₃, -Bn, -Ph, -Et, propyl, and isopropyl.

Non-limiting examples of compounds that can be synthesized by the processes presented in the present invention include:

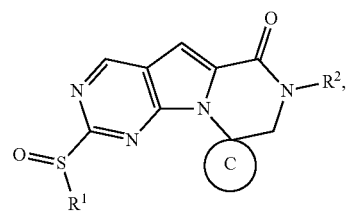

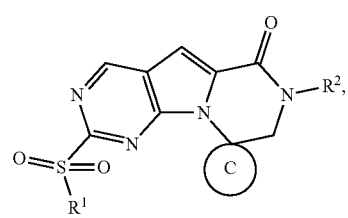

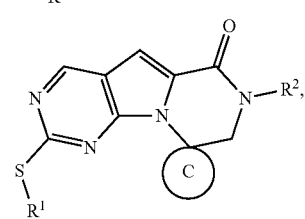

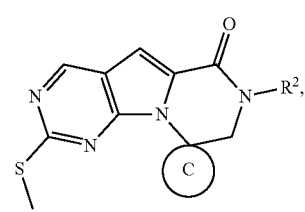

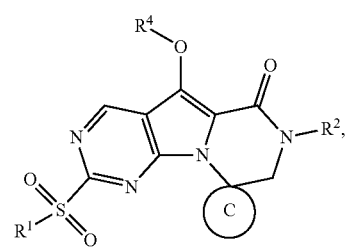

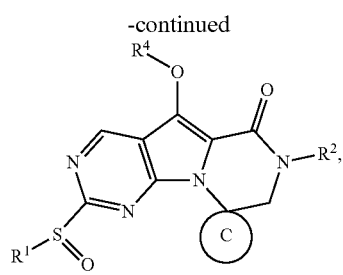
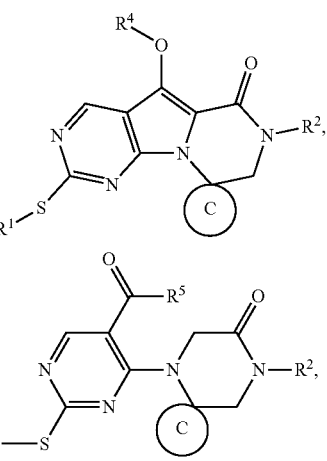
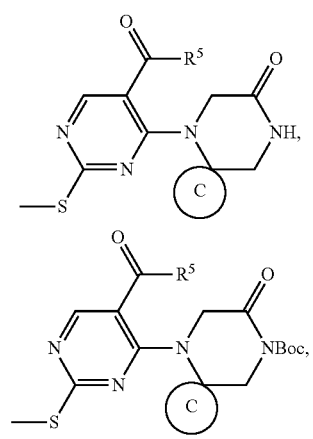
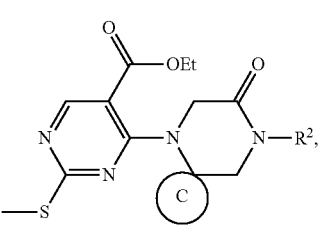
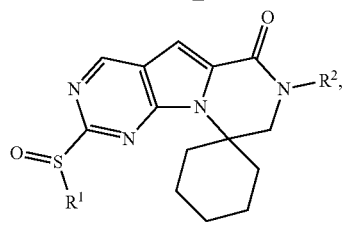
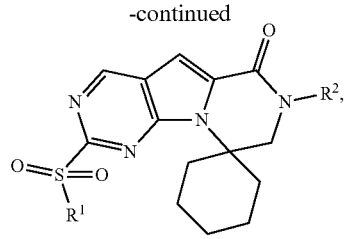
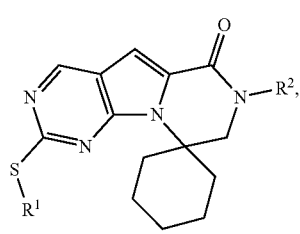
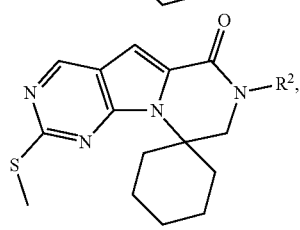
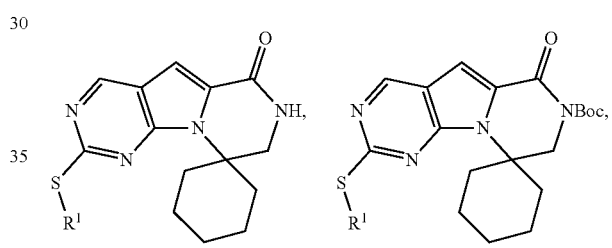
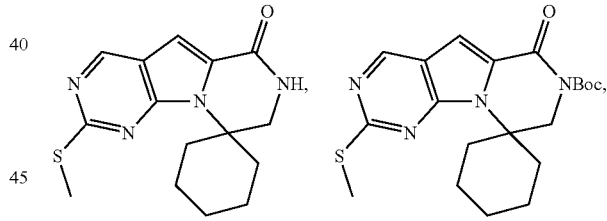
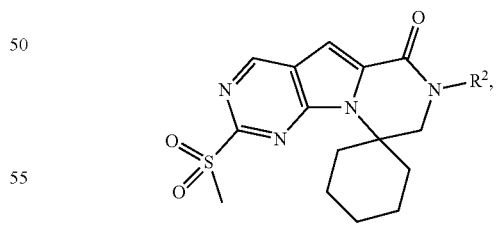
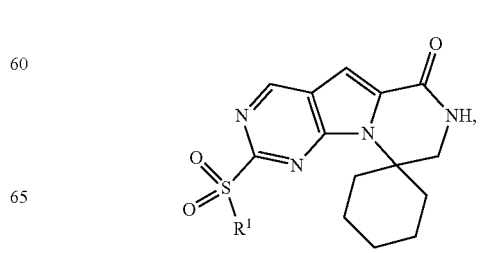

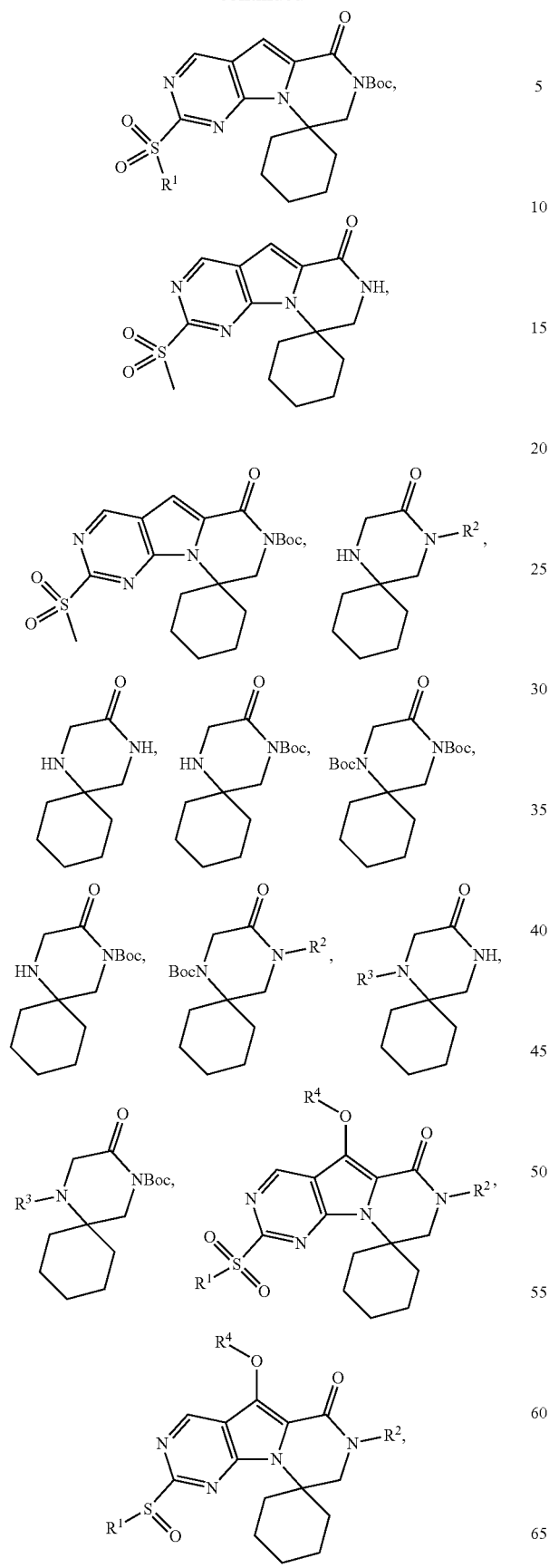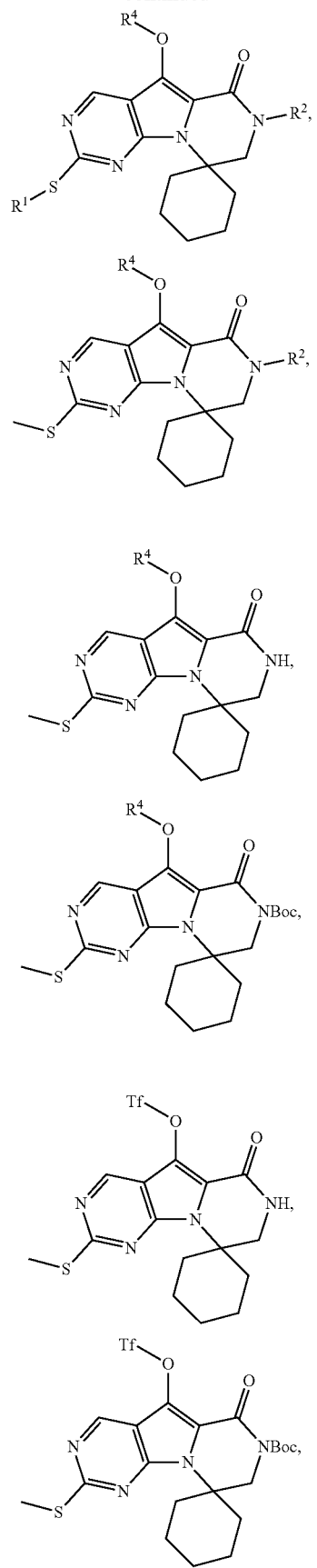

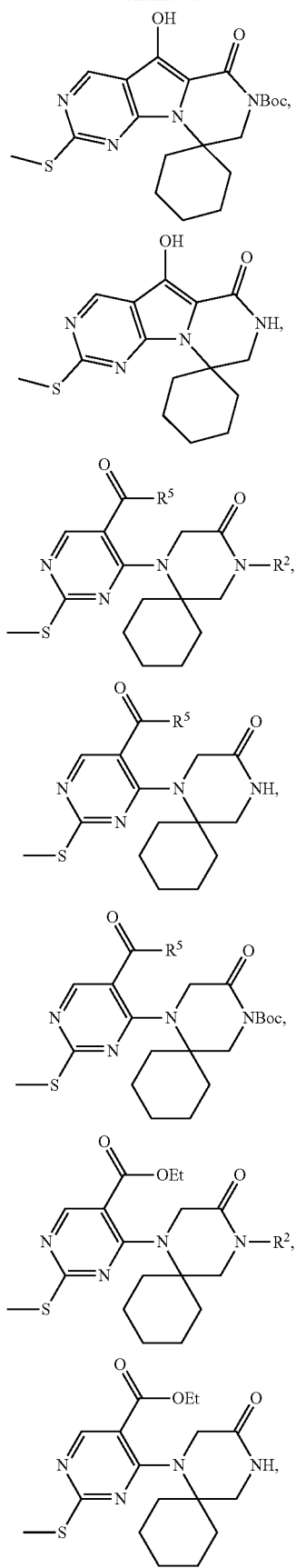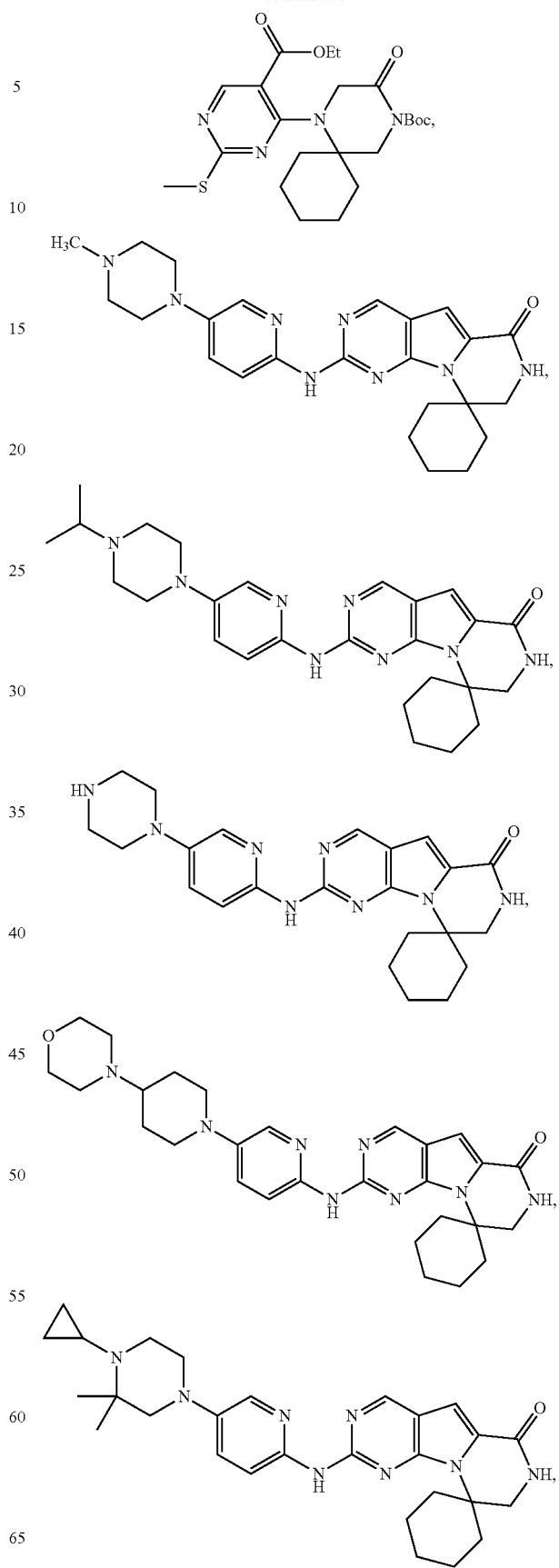

-continued

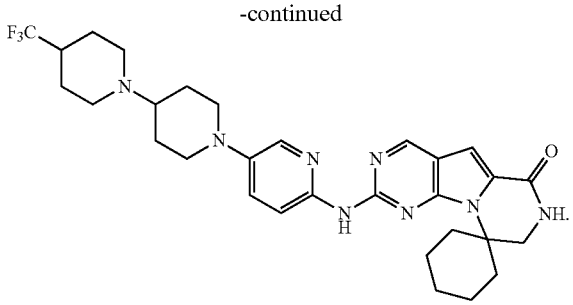

V. Illustrative Examples

According to the present invention the process to prepare compounds of Formula I, Formula II, Formula III, or Formula IV is provided:

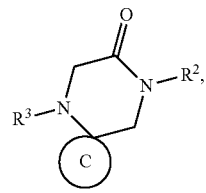
(I)

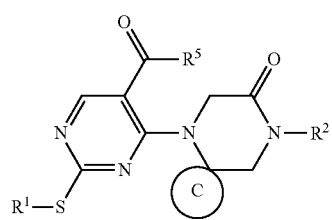
(II)

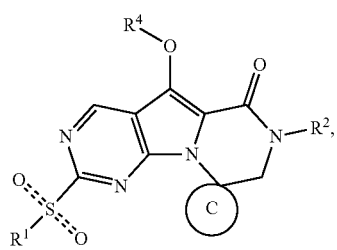
(III)

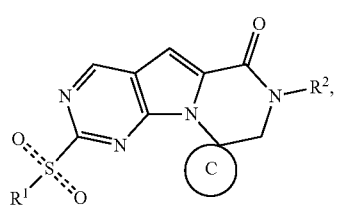
(IV)

as well as salts thereof. In one non-limiting embodiment, the compounds of the above Formulas are used in the synthesis of CDK inhibitors.

ABBREVIATIONS

| | |
|---|---|
| ACN | Acetonitrile |
| AUC | Area Under the Curve |
| Boc | tert-butyloxycarbonyl |
| Boc$_2$O | di-tert-butyl dicarbonate |
| CBZ | Carboxybenzyl |
| DABCO | 1,4-diazabicyclo[2.2.2]octane |
| DBU | 1,8 Diazabicycloundec-7-ene |
| DCM, CH$_2$Cl$_2$ | Dichloromethane |
| DIEA, DIPEA | N,N-diisopropylethylamine |
| DMA, DMAc | N,N-dimethylacetamide |
| DMAP | 4-Dimethylaminopyridine |
| DMF | N,N-dimethylformamide |
| DMSO | Dimethylsulfoxide |
| Et | Ethyl |
| h, hr | Hour |
| HMPA | Hexamethylphosphoramide |
| HPLC | High Pressure Liquid Chromatography |
| K$_2$CO$_3$ | Potassium carbonate |
| mCPBA | meta-Chloroperoxybenzoic acid |
| MTBE | Methyl Tertiary Butyl Ether |
| NMP | N-Methyl-2-pyrrolidone |
| NMR | Nuclear Magnetic Resonance |
| Pd(PPh$_3$)$_4$ | Tetrakis(triphenylphosphine)palladium(0) |
| Pt | Platinum |
| RT | Room temperature |
| TEA | Trimethylamine |
| Tf$_2$O | Trifluoromethanesulfonic anhydride |
| TFA | Trifluoroacetic acid |
| THF | Tetrahydrofuran |

General Methods

The structure of starting materials, intermediates, and final products was confirmed by standard analytical techniques, including NMR spectroscopy and mass spectrometry. Unless otherwise noted, reagents and solvents were used as received from commercial suppliers. Proton nuclear magnetic resonance spectra were obtained on a Bruker AVANCE 500 at 500 MHz in DMSO-d$_6$. HPLC analyses were performed on a Waters HPLC using the below HPLC method.

HPLC Method

| | |
|---|---|
| Column: | Atlantis T3 (150 × 4.6, 3 μm) |
| Column Temperature: | 40° C. |
| Flow Rate: | 1 mL/min |
| Detection: | UV @ 275 nm |
| Analysis Time: | 36 min |
| Mobile Phase A: | Water (with 0.1% Trifluoroacetic Acid) |
| Mobile Phase B: | Acetonitrile (with 0.1% Trifluoroacetic Acid) |
| Sample preparation: | dissolve IPC sample, wet or dry solid (≈1 mg of active compound) in acetonitrile/water (1/1) to achieve complete dissolution. |

HPLC Method Gradient

| Time (Minutes) | % A | % B |
|---|---|---|
| 0 | 100 | 0 |
| 5 | 100 | 0 |
| 23 | 5 | 95 |
| 28 | 5 | 95 |
| 28.1 | 100 | 0 |

Example 1. General Routes of Synthesis

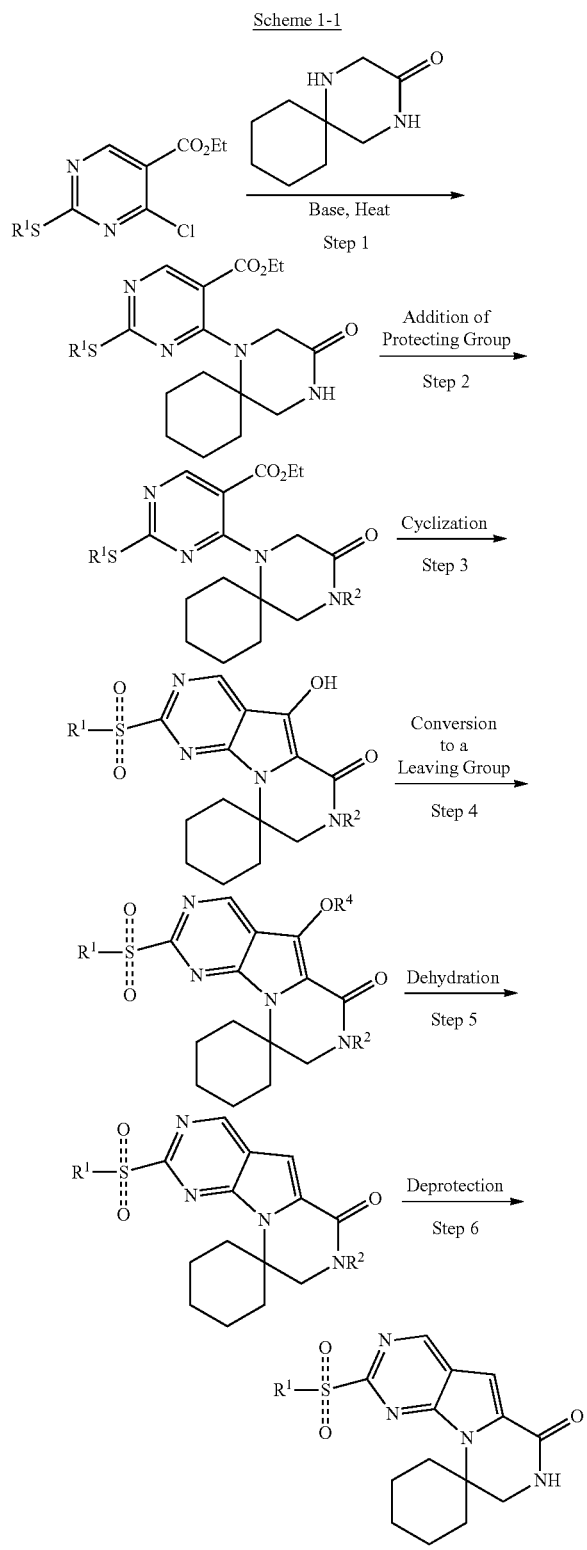

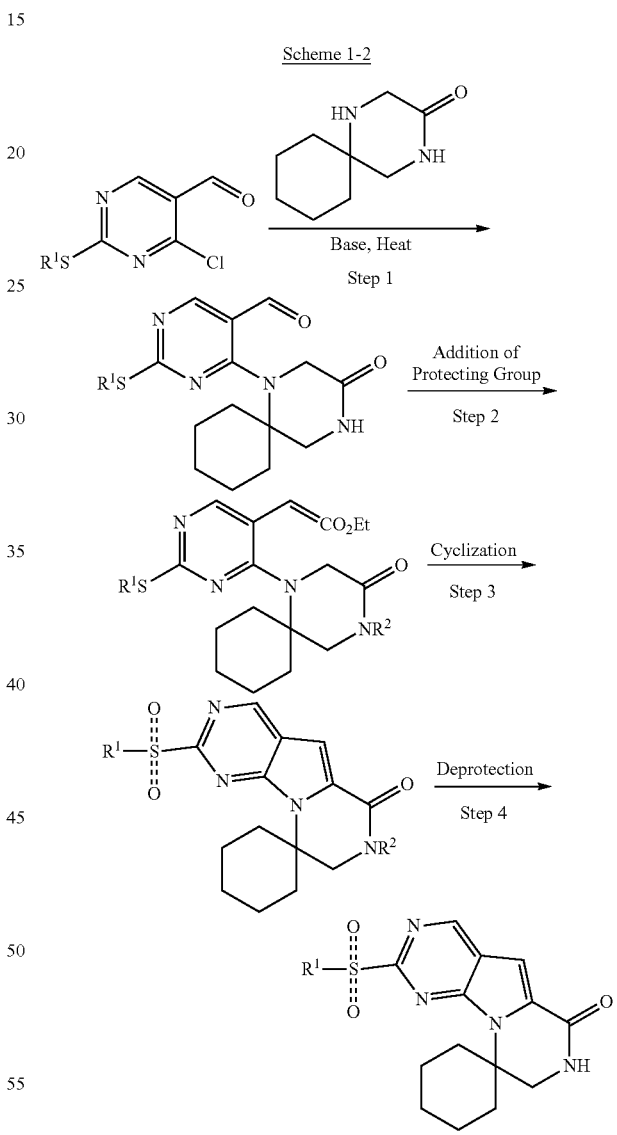

Scheme 1-1: Starting from an appropriately substituted halo pyrimidine, compounds of the present invention can be prepared. In Step 1 the appropriately substituted halo pyrimidine is subjected to 1,4-diazaspiro[5.5]undecan-3-one in the presence of base and heat to afford a substituted spirolactam. In Step 2 the appropriately substituted spirolactam is protected with a group selected from $R^2$. In Step 3 the protected spirolactam is cyclized in the presence of base to afford a fused spirolactam. The fused spirolactam can be optionally oxidized to a sulfoxide or sulfone after Step 3, Step 4, Step 5, or Step 6. Oxidation prior to Step 3 results in undesired byproducts. In Step 4 the hydroxyl group of the fused spirolactam is converted to a leaving group. In Step 5 the leaving group is dehydrated to afford a compound of Formula IV. In Step 6 the compound of Formula IV is optionally deprotected.

Scheme 1-2: Starting from an appropriately substituted halo pyrimidine compounds of the present invention can be prepared. In Step 1 the appropriately substituted halo pyrimidine is subjected to 1,4-diazaspiro[5.5]undecan-3-one in the presence of base and heat to afford a substituted spirolactam. In Step 2 the appropriately substituted spirolactam is protected with a group selected from $R^2$. In Step 3 the protected spirolactam is cyclized in the presence of base to afford a fused spirolactam of Formula IV. The fused spirolactam can be optionally oxidized to a sulfoxide or sulfone after Step 3 or Step 4. Oxidation prior to Step 3 results in undesired byproducts. In Step 4 the compound of Formula IV is optionally deprotected.

to afford a compound of Formula I. In Step 4 the compound of Formula I is optionally protected.

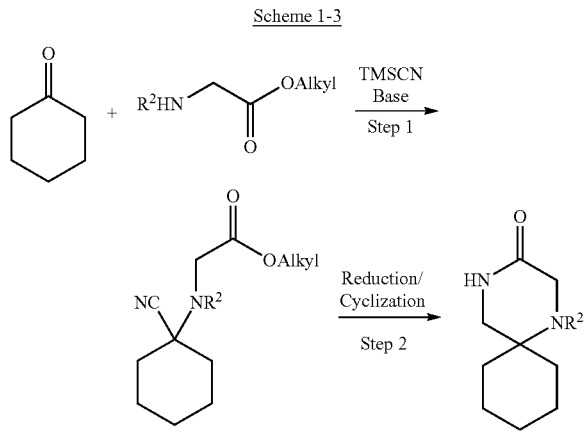

Scheme 1-3: Starting from an appropriately substituted alkyl glycinate, compounds of the present invention can be prepared. In Step 1 the appropriately substituted alkyl glycinate is subjected to cyclohexanone and TMSCN in the presence of base to afford a cyano species. In Step 2 the appropriately substituted cyanospecies is reduced and subsequently cyclized to afford a compound of Formula I.

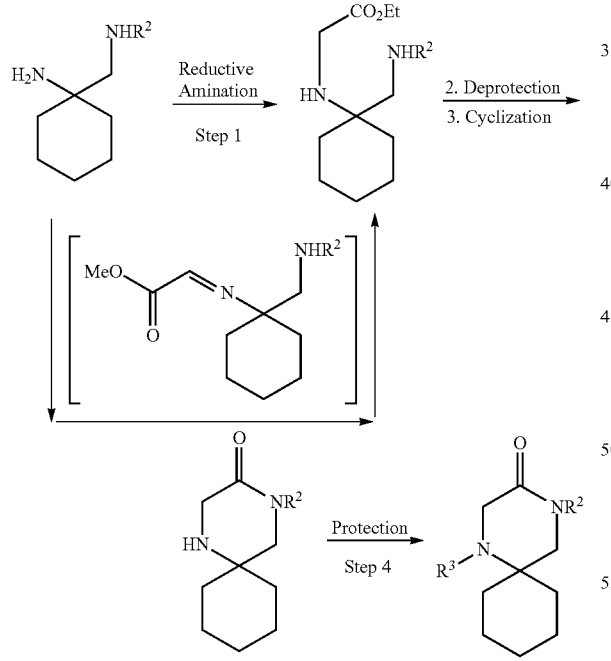

Scheme 1-4: Starting from an appropriately substituted 1-(aminomethyl)cyclohexan-1-amine, compounds of the present invention can be prepared. In Step 1 the appropriately substituted 1-(aminomethyl)cyclohexan-1-amine is reductively aminated with an aldehyde. In Step 2 the appropriately substituted cyclohexane amine is optionally deprotected (i.e.: the group selected from $R^2$ if not H is optionally replaced by H). In Step 3 the cyclohexane amine is cyclized

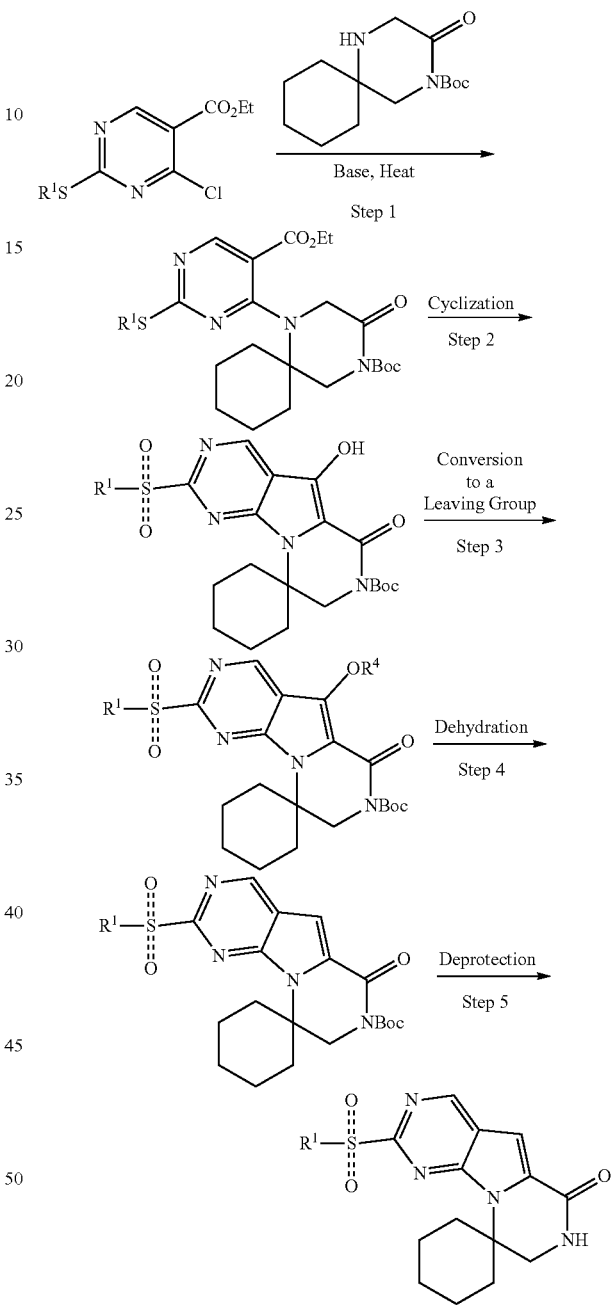

Scheme 1-5: Starting from an appropriately substituted halo pyrimidine, compounds of the present invention can be prepared. In Step 1 the appropriately substituted halo pyrimidine is subjected to 1,4-diazaspiro[5.5]undecan-3-one in the presence of base and heat to afford a substituted spirolactam. In Step 2 the protected spirolactam is cyclized in the presence of base to afford a fused spirolactam. The fused spirolactam can be optionally oxidized to a sulfoxide or sulfone after Step 2, Step 3, Step 4, or Step 5. Oxidation prior to Step 2 results in undesired byproducts. In Step 3 the hydroxyl group of the fused spirolactam is converted to a leaving group. In Step 4 the leaving group is dehydrated to afford a compound of Formula IV. In Step 5 the compound of Formula IV is optionally deprotected.

Scheme 1-6

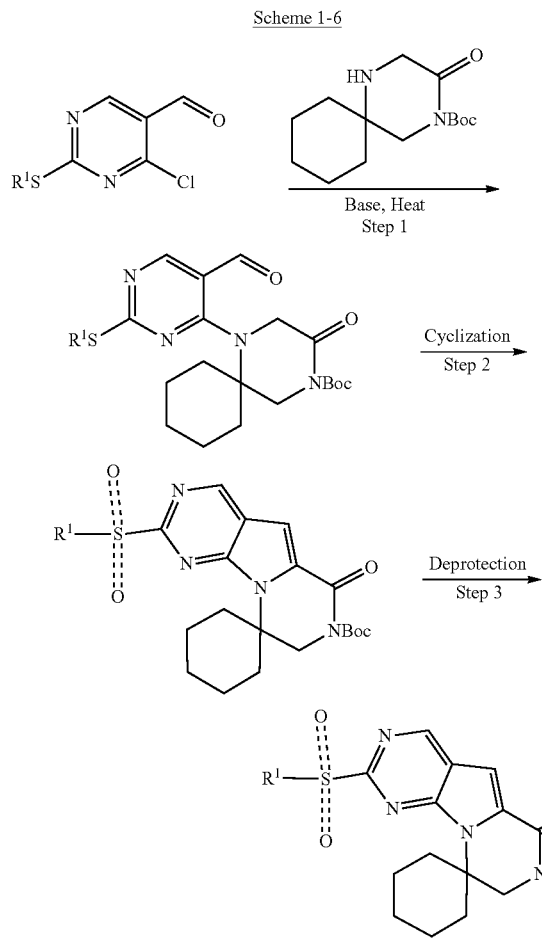

Scheme 1-6: Starting from an appropriately substituted halo pyrimidine compounds of the present invention can be prepared. In Step 1 the appropriately substituted halo pyrimidine is subjected to 1,4-diazaspiro[5.5]undecan-3-one in the presence of base and heat to afford a substituted spirolactam. In Step 2 the protected spirolactam is cyclized in the presence of base to afford a fused spirolactam of Formula IV. The fused spirolactam can be optionally oxidized to a sulfoxide or sulfone after Step 2 or Step 3. Oxidation prior to Step 2 results in undesired byproducts. In Step 3 the compound of Formula IV is optionally deprotected.

Scheme 1-7

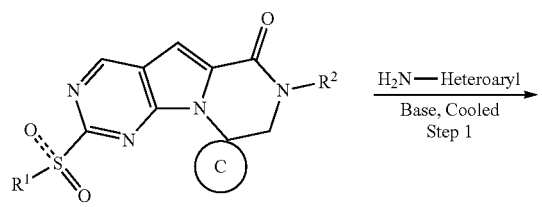

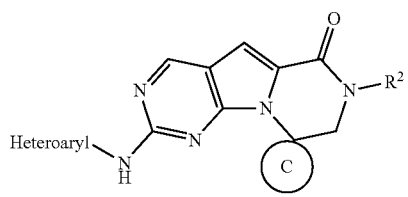

Scheme 1-7: Starting from compound of Formula IV a CDK4/6 inhibitor can be prepared. In Step 1 a heteroaryl amine is subjected to a base and a compound of Formula IV is added slowly under chilled conditions to afford a nucleophilic substitution reaction. The compound of Formula IV can previously be prepared as described in the schemes herein.

Example 2. Representative Routes of Synthesis

Scheme 2-1

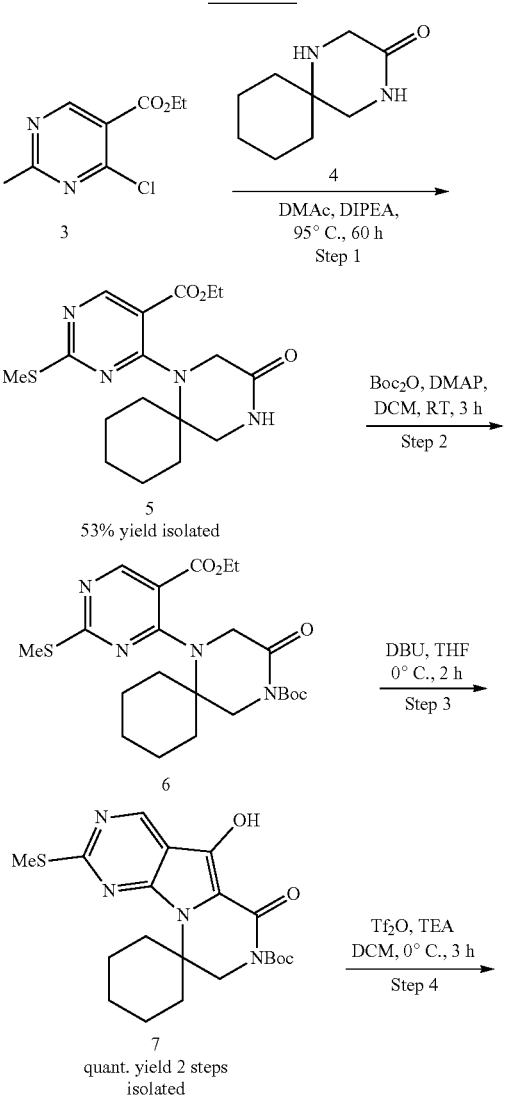

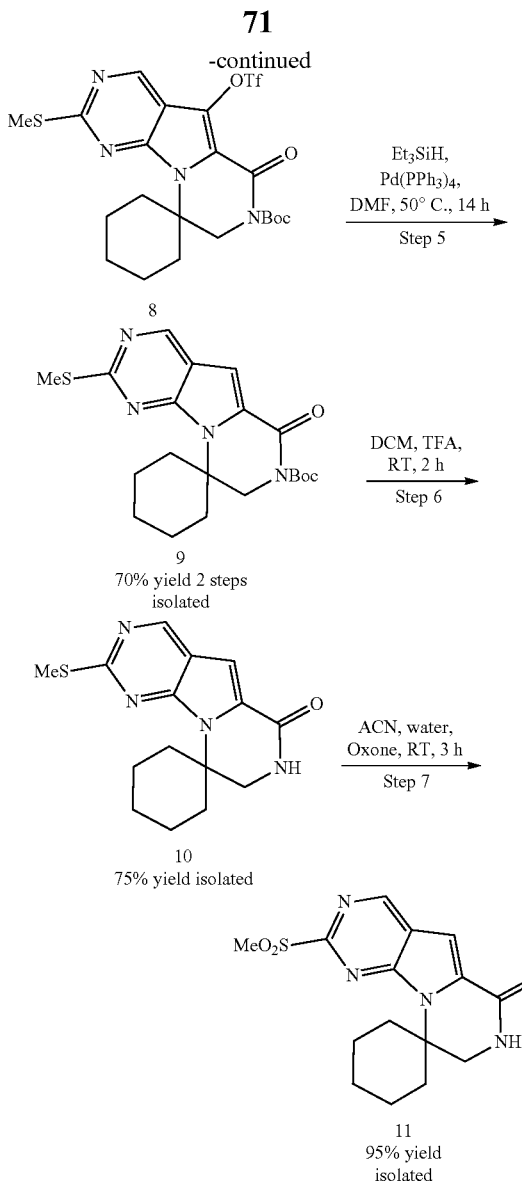

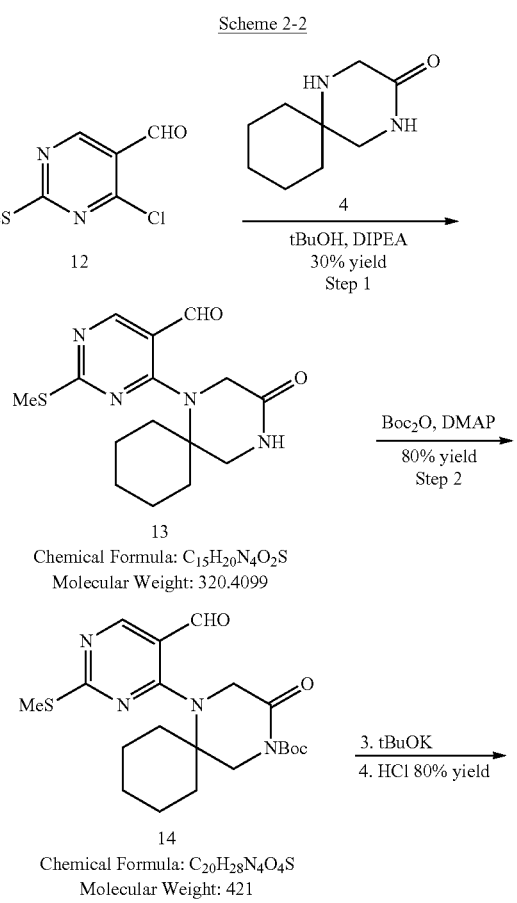

semi-solid nature of compound 6, the material was taken to the next step without further purification. The Dieckmann condensation was initially performed with strong bases such as LiHMDS and tBuOK. A similar result to the aldehyde route (Scheme 2-2) was obtained: a partial deprotection of Boc group was observed that required column chromatography. However, the best results were obtained when DBU was used as base and THF as solvent. The reaction outcome was complete, clean conversion of 6 to 7. Moreover, the product crystallized from the reaction mixture upon seeding, and a quantitative yield was obtained for the two steps.

The hydroxyl group of 7 was removed via a two-step procedure. First, compound 7 was converted completely into triflate 8 using triflic anhydride and triethylamine in dichloromethane. The reaction was found to proceed well at 0° C. Due to the potential instability of the triflate intermediate, it was not isolated. It was immediately taken to the next step and reduced with triethylsilane and palladium tetrakis to afford the product 9 after ethyl acetate crystallization in ~70% yield. The Boc group of 9 was removed using trifluoroacetic acid in dichloromethane to afford 10. Intermediate 10 was converted into the final sulfone 11 using Oxone™ in acetonitrile/water solvent system.

The obtained sulfone 11 was use-tested in the coupling step and was found to perform well. In conclusion, the route to sulfone 11 was developed which eliminated the use of column chromatography with good to excellent yields on all steps.

Scheme 2-1: An ester route is one embodiment, of the present invention. Ideally, the best synthesis scheme would afford crystalline intermediates to provide material of consistent purity without column chromatography, and high yielding steps while using safe and cost effective reagents when possible.

The first step in the ester route is a SNAr nucleophilic substitution of Cl group in commercially available ester 3 using spirolactam 4. Due to low reactivity of 4, a reaction temperature of 85-95° C. was required. Because of the temperature requirements, DIPEA and dimethylacetamide were selected as the base and solvent, respectively. The reaction follows second-order kinetics and usually stalls after ~85% conversion. Therefore, the reaction was typically stopped after 60 hours by first cooling it to room temperature at which point solid formation was observed. The mixture was then partitioned between MTBE and water and product was filtered with excellent purity with ~53% yield of the desired product 5. The obtained compound 5 was protected with a Boc group using Boc anhydride and DMAP as the catalyst and dichloromethane as the solvent. The intermediate 6 was obtained in a quantitative yield. Due to the -continued

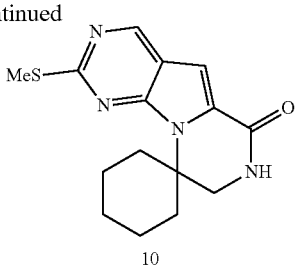

10

Scheme 2-2: The first step of Scheme 2-2 consistently afforded product 13 contaminated with one major impurity found in substantial amount. Thorough evaluation of the reaction impurity profile by LC-MS and 2D NMR was performed, which showed the impurity was structurally the condensation of two aldehyde 12 molecules and one molecule of lactam 4. Therefore, column chromatography was required to purify compound 13, which consistently resulted in a modest 30% yield. A solvent screen revealed that sec-butanol, amyl alcohol, dioxane, and tert-butanol can all be used in the reaction but a similar conversion was observed in each case. However, tert-butanol provided the cleanest reaction profile, so it was selected as a solvent for the reaction. Assessing the impact of varying the stoichiometric ratio of 4 and 12 on the reaction outcome was also investigated. The reaction was performed with 4 equivalents of amine 4 in an attempt to disrupt the 2:1 aldehyde/amine composition of the impurity. The result was only a marginal increase in product 13 formation. The temperature impact on the reaction outcome was evaluated next. The coupling of aldehyde 12 and 4 was investigated at two different temperatures: 50° C. and 40° C. with 1:1 ratio of aldehyde/amine. Reactions were checked at 2 and 4 hours and then every 12 hours. The reaction progress was slow at 50° C. and was accompanied by growth of other impurities. The reaction at 40° C. was much cleaner; however, the conversion was lower in the same period. The mode of addition of the reagents was investigated as well at 80° C. with a slow addition (over 6 hours) of either aldehyde 12 or amine 4 to the reaction mixture. The product distribution did not change and an about 1 to 1 ratio was observed between product and impurity when amine 4 was added slowly to the reaction mixture containing aldehyde 12 and DIPEA at reflux. The product distribution did change when aldehyde 12 was added slowly to the mixture of amine 4 and DIPEA. However, the major product of the reaction was the undesired impurity. Other organic bases were tried as well as different ratios of DIPEA. No product was observed when potassium carbonate was used as a base. The results of the experiments are presented in Table 1 below.

TABLE 1

| Entry | Base | Product (AUC %, 270 nm) | Impurity 22.3 min (AUC %, 270 nm) |
|---|---|---|---|
| 1 | TEA | 55 | 45 |
| 2 | DABCO | none | none |
| 3 | DBU | none | none |
| 4 | Pyridine | none | none |
| 5 | 2,6-lutidine | 35 | 65 |
| 6 | DIPEA 2eq | 55 | 40 |
| 7 | DIPEA 3eq | 46 | 49 |
| 8 | DMAP | none | none |

Compound 13 was successfully formed in three cases: triethylamine, 2,6-lutidine and DIPEA, with the DIPEA result being the best. The use of Boc protected spirolactam 4 had no effect on the impurity formation as well. Its utilization was speculated to be beneficial in performing the coupling step together with the following step, preparation of compound 14.

The major impurity formed during Step 1 of Scheme 2-2 is:

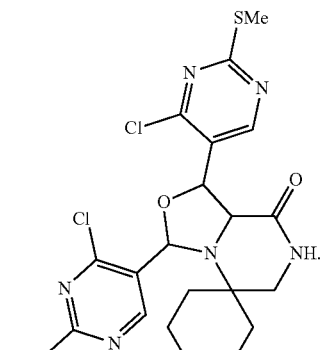

Chemical Formula: C$_{21}$H$_{24}$Cl$_2$N$_6$O$_2$S$_2$
Molecular Weight: 527.4903

The second step (Boc protection of the free lactam) proceeded well using DMAP as a catalyst in dichloromethane at room temperature. The product 14 is a thick oil, and, therefore, cannot be purified by crystallization. The Boc protected intermediate 14 was cyclized successfully into the desired pentacyclic structure 10 upon treatment with a strong base such as LiHMDS or tBuOK. Surprisingly, the Boc group was partially removed during the reaction. The level of deprotection was independent from the internal reaction temperature and was positively correlated with excess of base used. Therefore, the mixture of the desired product 10 and 10-Boc compound was treated with acid to completely deprotect Boc group. The conversion of methyl sulfide into the final sulfone 11 was carried out with Oxone™. Initially a mixture of methanol and water was used for the reaction. As the result, a partial displacement of sulfone by methoxy group was detected. The methanol was replaced with acetonitrile and the sulfone displacement was eliminated.

In summary, the ester route (Scheme 2-1) is preferred because:
1. Formation of the impurity during the first step of Scheme 2-2 was unavoidable and resulted in yields of <35%.
2. Column purification was required to isolate intermediate 14.
3. The aldehyde starting material was not commercially available and required two synthetic steps from the corresponding ester.

Scheme 2-3

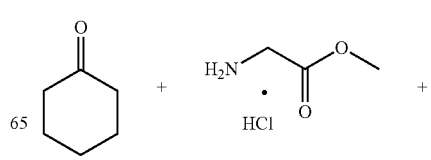

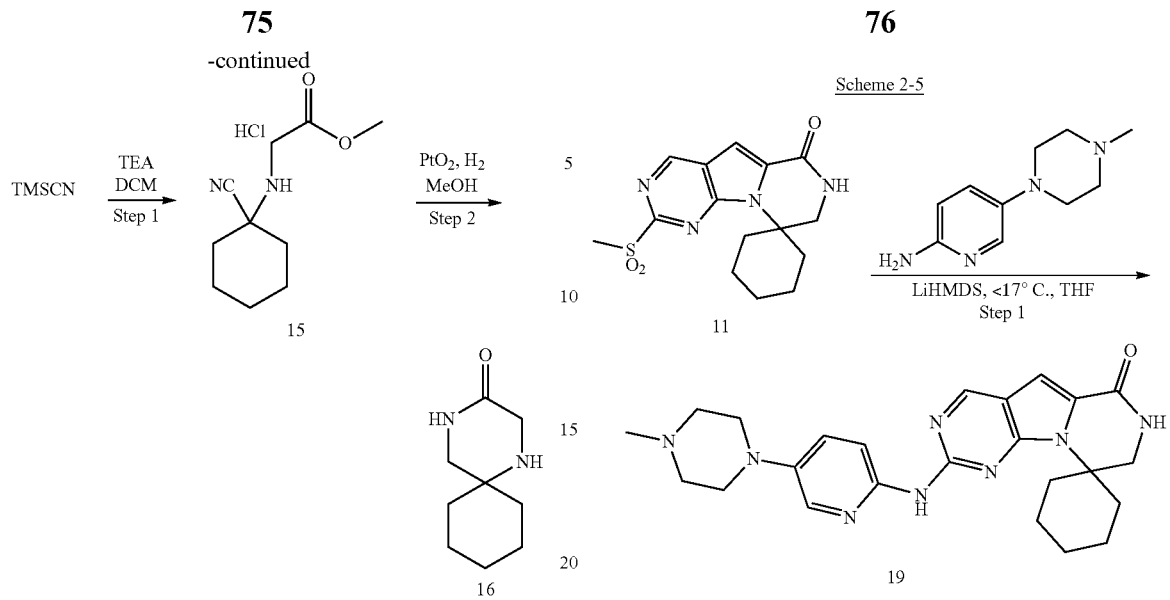

Scheme 2-5

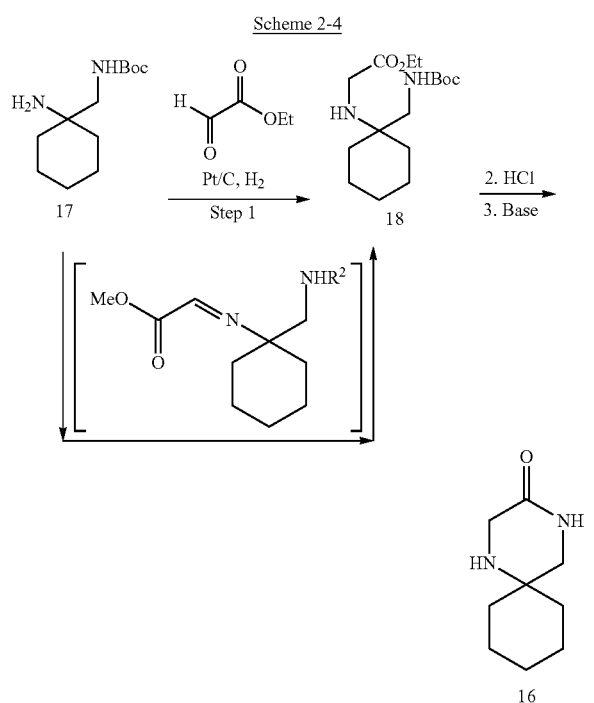

Scheme 2-3: Starting with cyclohexanone, compounds of the present invention can be prepared. In Step 1 the methyl glycinate is subjected to cyclohexanone and TMSCN in the presence of triethyl amine in DCM to afford 15. In Step 2 15 hydrogenated with hydrogen gas in the presence of catalytic platinum oxide and subsequently undergoes an intramolecular cyclization to afford compound 16 which is used in the schemes above.

Scheme 2-5: Starting from compound 11 the CDK 4/6 inhibitor 19 can be prepared. In Step 1 5-(4-methylpiperazin-1-yl)pyridin-2-amine is subjected to LiHMDS and compound 11 is added slowly under chilled conditions to afford a nucleophilic substitution reaction and compound 19. Compound 11 can be prepared as described in the schemes herein.

Scheme 2-4

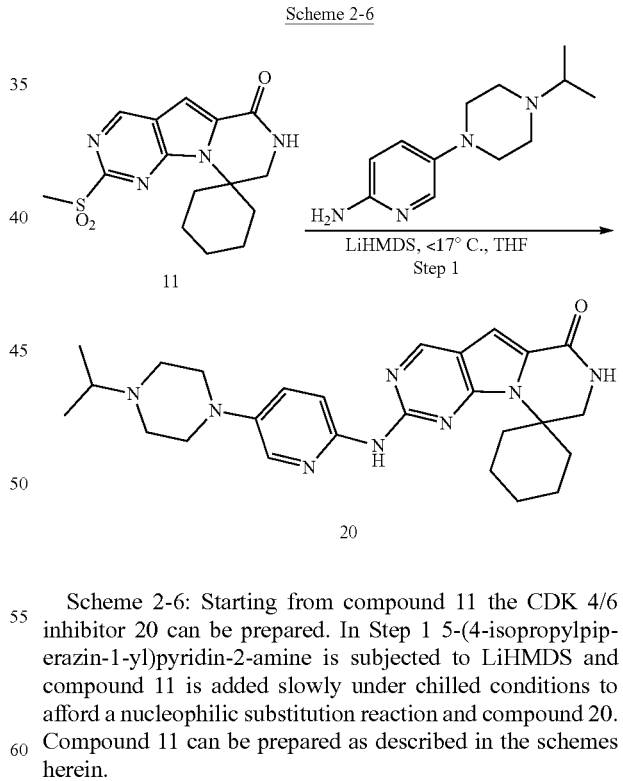

Scheme 2-4: Starting with compound 17, compounds of the present invention can be prepared. In Step 1 compound 17 is subjected to ethyl 2-oxoacetate in the presence platinum on carbon and hydrogen gas to afford compound 18. In Step 2 compound 18 is Boc-deprotected with hydrochloric acid. In Step 3 compound 18 is cyclized to afford compound 16 which is used in the schemes above.

Scheme 2-6: Starting from compound 11 the CDK 4/6 inhibitor 20 can be prepared. In Step 1 5-(4-isopropylpiperazin-1-yl)pyridin-2-amine is subjected to LiHMDS and compound 11 is added slowly under chilled conditions to afford a nucleophilic substitution reaction and compound 20. Compound 11 can be prepared as described in the schemes herein.

Preparation of Compound 5:

A 500 mL, three-neck flask equipped with a mechanical overhead stirrer, thermocouple, $N_2$ inlet, and reflux condenser was charged with ethyl 4-chloro-2-(methylthio)pyrimidine-5-carboxylate 3 (49.2 g, 0.21 mol, 1.00 equiv.), spirolactam 4 (39.2 g, 0.23 mol, 1.10 equiv.), DIPEA (54.7 g, 0.42 mol, 2.00 equiv.), and DMAc (147.6 mL, 3 vol). The batch was heated to 90-95° C., and after 60 h, IPC confirmed ~14% (AUC) of ethyl 4-chloro-2-(methylthio)pyrimidine-5-carboxylate remained. The batch was cooled to RT, and precipitate formation was observed. The suspension was diluted with MTBE (100 mL, 2 vol) and water (442 mL, 9 vol) and stirred for 2 h at RT. The product was isolated by vacuum filtration and washed with MTBE (49 mL, 1 vol). The solid cake was conditioned for 1 h and dried under vacuum at 40° C. for 16 h to afford compound 5 [41.0 g, 53% yield] as an off-white solid with a purity of >99% AUC. $^1$H NMR (CDCl$_3$): δ 8.76 (d, J=2.0 Hz, 1H), 6.51-6.29 (br, 1H), 4.33 (q, J=7.0 Hz, 2H), 3.78 (s, 2H), 3.58 (s, 2H), 2.92 (s, 2H), 2.53 (s, 3H), 1.63-1.37 (m, 12H). LCMS (ESI, m/z=365.3 [M+H]).

Preparation of Compound 6:

A 500 mL, three-neck flask equipped with a mechanical overhead stirrer, thermocouple, N$_2$ inlet was charged with 5 [41.0 g, 0.11 mol, 1.00 equiv.], Boc-anhydride (36.8 g, 0.17 mol, 1.50 equiv.), DMAP (1.37 g, 0.01 mol, 0.10 equiv.), and dichloromethane (287 mL, 7 vol). The batch was stirred for 3 h at RT. IPC confirmed no starting material remained (AUC). The batch was concentrated into a residue under reduced pressure and taken to the next step (a quantitative yield is assumed for this step). An aliquot (200 mg) was purified by column chromatography (heptanes/ethyl acetate 0 to 100%) to afford compound 6. $^1$H NMR (CDCl$_3$): δ 8.64 (s, 1H), 4.31 (q, J=7.0 Hz, 2H), 4.07 (s, 2H), 3.83 (S, 2H), 3.15 (m, 2H), 2.56 (s, 3H), 172 (m, 3H), 1.59 (m, 15H), 1.42 (t, J=7.0 Hz, 3H). LCMS (ESI, m/z=465.2 [M+H]).

Preparation of Compound 7:

A 500 mL, three-neck flask equipped with a mechanical overhead stirrer, thermocouple, N$_2$ inlet was charged with compound 6 [residue from a previous step, quantitative yield assumed, 52.2 g, 0.11 mol, 1.00 equiv.], and THF (261 mL, 5 vol). The batch was cooled to 0° C. and 1,8-diazabicyclo[5.4.0]un-dec-7-ene (17.1 g, 0.11 mmol, 1.00 equiv.) was added keeping the internal temperature in 0-10° C. range. After the addition was complete, the cooling bath was removed and the reaction mixture was allowed to warm up to RT and after 2 h, IPC confirmed no starting material remained. The batch was seeded with the product (1.0 g) and was cooled to 0° C. The slurry was stirred at 0° C. for 2 h. The product was isolated by vacuum filtration and washed with cold (0° C.) THF (50 mL, 1 vol). The solid cake was conditioned for 1 h and dried under vacuum at 40° C. for 16 h to afford 7 [47 g, quantitative yield] as a light orange solid with a purity of >99% AUC. The color of the product changed into yellow once the batch was exposed to air for an extended period of time (~1 day). Material was isolated with substantial amount DBU, according to proton NMR. However, it did not interfere with the next step. $^1$H NMR (CDCl$_3$): δ 8.71 (s, 1H), 4.03 (s, 2H), 2.57 (s, 3H), 1.85 (m, 10H), 1.51 (s, 9H). LCMS (ESI, m/z=419.2 [M+H]).

Preparation of Compound 8:

A 500 mL, three-neck flask equipped with a mechanical overhead stirrer, thermocouple, N$_2$ inlet was charged with 7 [40.8 g, 0.10 mol, 1.00 equiv.], triethylamine (31.5 g, 0.31 mol, 3.20 equiv.), and dichloromethane (408 mL, 10 vol). The batch was purged with N$_2$ for 15 min and was cooled to 0° C. Triflic anhydride (44.0 g, 0.16 mol, 1.60 equiv.) was added keeping the internal temperature in 0-10° C. range. The batch was stirred at 0° C. and after 3 h, IPC confirmed ~7.0% (AUC) of 7 remained. [It was speculated that the product was hydrolyzing back into starting material during the analysis.] Once the reaction was deemed complete, the batch was transferred to a 1 L, separatory funnel and was washed with 50% saturated sodium bicarbonate (200 mL, 5 vol). [It was prepared by mixing saturated sodium bicarbonate (100 mL) with water (100 mL)).] The aqueous layer was separated and was extracted with DCM (2×40 mL, 1 vol). The organic layers were combined and concentrated into a residue under reduced pressure and taken to the next step. LCMS (ESI, m/z=551.6 [M+H]).

Preparation of Compound 9:

A 500 mL, three-neck flask equipped with a mechanical overhead stirrer, thermocouple, N$_2$ inlet was charged with compound 8 [residue from a previous step, quantitative yield assumed, 53.7 g, 0.10 mol, 1.00 equiv.], and THF (110 mL, 2 vol). The solvent was removed under vacuum distillation and the procedure was repeated two times. The flask was charged with triethylsilane (22.7 g, 0.20 mol, 2.00 equiv.), and DMF (268 mL, 5 vol). The batch was degassed by five cycles of evacuation, followed by backfilling with nitrogen. The flask was charged with tetrakis(triphenylphosphine)palladium(0) (11.3 g, 0.01 mol, 0.1 equiv.). The batch was heated to 45-50° C., and after 14 h, IPC confirmed no starting material remained. The batch was transferred to a 500 mL, separatory funnel while still warm. The reaction was partitioned between water (5 vol) and ethyl acetate (5 vol). The aqueous layer was extracted with ethyl acetate (3×3 vol). The organic layers were combined and concentrated down to 2 volumes. The precipitate was filtered and washed with ethyl acetate (2×1 vol). The solid cake was conditioned for 1 h and dried under vacuum at 40° C. for 16 h to afford 9 [27.5 g, 70% yield] as a yellow solid with a purity of ~98% AUC. Proton NMR showed some triphenylphosphine oxide present. $^1$H NMR (DMSO-d$_6$): δ 9.01 (s, 1H), 7.40 (s, 1H), 4.30 (s, 2H), 2.58 (m, 2H), 2.58 (s, 3H), 1.81 (m, 5H), 1.51 (s, 9H). LCMS (ESI, m/z=403.4 [M+H]).

Preparation of Compound 10 from the Scheme 2-1 Route:

A 500 mL, three-neck flask equipped with a mechanical overhead stirrer, thermocouple, N$_2$ inlet was charged 9 (12.8 g, 31.8 mmol, 1.00 equiv.) and dichloromethane (64 mL, 5 vol). Trifluoroacetic acid (18.2 g, 159 mmol, 5.00 equiv.) was added over 20 min and the solution was stirred for 2 h at RT. IPC confirmed reaction was complete. The batch was transferred to a 500 mL, separatory funnel and washed with saturated sodium bicarbonate (200 mL). The aqueous layer was extracted with dichloromethane (3×3 vol). The organic layers were combined and concentrated down to 1 volume. The precipitate was filtered and conditioned for 1 h and dried under vacuum at 40° C. for 16 h to afford 9 [6.72 g, 70% yield] as an off-white solid with a purity of 99.1% AUC. $^1$H NMR (DMSO-d$_6$): δ 8.95 (s, 1H), 8.32 (s, 1H), 7.15 (s, 1H), 3.68 (d, J=1.0 Hz, 2H), 2.86 (m, 2H), 2.57 (s, 3H), 1.92 (m, 2H), 1.73 (m, 3H), 1.39 (m, 3H). LCMS, ESI, m/z=303.2 [M+H]).

Preparation of Compound 10 from Scheme 2-2 Route:

A 50 mL, three-neck flask equipped with a magnetic stirring bar, thermocouple, N$_2$ inlet was charged 14 (680 mg, 1.62 mmol, 1.00 equiv.) and THF (6.8 mL, 10 vol). A 1 M solution of potassium tert-butoxide (3.2 mL, 3.24 mmol, 2.00 equiv.) in THF was added over 10 min and the solution was stirred for 2 h at RT. IPC confirmed reaction was complete. The batch was acidified with 4 N hydrogen chloride solution in dioxane (2.4 mL, 9.72 mmol, 6.00 equiv.) and stirred for additional 1 h. The batch was transferred to a 500 mL, separatory funnel and washed with saturated sodium bicarbonate (100 mL). The aqueous layer was extracted with ethyl acetate (3×20 vol). The organic layers were combined and concentrated down to 3 volumes and product precipitated. The precipitate was filtered and conditioned for 1 h and dried under vacuum at 40° C. for 16 h to afford 9 [489 mg, quantitative yield] as an off-white solid.

Preparation of Compound 11:

A 500 mL, three-neck flask equipped with a mechanical overhead stirrer, thermocouple, $N_2$ inlet was charged with 10 (9.00 g, 29.8 mmol, 1.00 equiv.), and acetonitrile (180 mL, 20 vol). A solution of Oxone™ (45.9 g, 0.15 mol, 5.00 equiv.) in water (180 mL, 20 vol) was added to the batch over 20 min. The batch was stirred for 2 h and IPC confirmed the reaction was complete. The batch was concentrated down to of the original volume and was extracted with dichloromethane DCM (4×10 vol). The organic layers were combined; polish filtered and concentrated down to ~10 vol of DCM. The product was slowly crystallized out by addition of heptanes (~30 vol). The mixture was cooled to 0° C. and the product was filtered and dried under vacuum at 40° C. for 16 h to afford 11 [9.45 g, 95% yield] as an off-white solid with a purity of >99% AUC. $^1H$ NMR ($CDCl_3$): δ 9.24 (s, 1H), 7.78 (s, 1H), 7.46 (s, 1H), 3.89 (d, J=2.0 Hz, 2H), 3.43 (s, 3H), 2.98 (m, 2H), 2.10 (m, 2H), 1.86 (m, 3H), 1.50 (m, 3H). LCMS (ESI, m/z=335.2 [M+H]).

Preparation of Compound 13:

A 250 mL, single-neck flask equipped with a mechanical overhead stirrer, thermocouple, $N_2$ inlet, and reflux condenser was charged with 4-chloro-2-(methylthio)pyrimidine-5-carbaldehyde (2.00 g, 10.6 mmol, 1.00 equiv.), spirolactam 4 (1.96 g, 11.7 mmol, 1.10 equiv.), DIPEA (2.74 g, 21.2 mmol, 2.00 equiv.), and tert-butanol (20 mL, 10 vol). The batch was heated to 80-85° C., and after 24 h, IPC confirmed no aldehyde 12 remained. The batch was cool to RT and concentrated into a residue, which was loaded on silica gel column. The product was eluted with ethyl acetate/heptanes (0% to 100%). The product containing fractions were pulled out and concentrated to afford 13 [0.98 g, 29% yield] as an off-white solid.

Preparation of Compound 14:

A 500 mL, three-neck flask equipped with a mechanical overhead stirrer, thermocouple, $N_2$ inlet was charged with 13 [0.98 g, 3.00 mmol, 1.00 equiv.], Boc-anhydride (4.90 g, 21.5 mmol, 7.00 equiv.), DMAP (36 mg, 0.30 mmol, 0.10 equiv.), and dichloromethane (7 mL, 7 vol). The batch was stirred for 3 h at RT. IPC confirmed no starting material remained. The batch was cool to RT and concentrated into a residue, which was loaded on silica gel column. The product was eluted with ethyl acetate/heptanes (0% to 100%). The product containing fractions were pulled out and concentrated to afford 14 [0.98 g, 29% yield] as an off-white solid.

Preparation of Compound 15:

To a suspension of methyl glycinate (500 g, 3.98 mol, 1 eq) in DCM (10 L) was added TEA dropwise at rt under nitrogen atmosphere, followed by the addition of cyclohexanone (781 g, 7.96 mol, 2 eq) dropwise over 15 min. To the resulting mixture was added TMSCN (591 g, 5.97 mol, 1.5 eq) dropwise over 1 hour while maintaining the internal reaction temperature below 35° C. After stirred at rt for 2 hrs, the suspension became a clear solution. The progress of the reaction was monitored by H-NMR.

When the methyl glycinate was consumed completely as indicated by H-NMR analysis, the reaction was quenched by water (5 L). The layers were separated. The aqueous layer was extracted with DCM (1 L). The combined organic phase was washed with water (5 L×2) and dried over $Na_2SO_4$ (1.5 Kg). After filtration and concentration, 1.24 Kg of crude 15 was obtained as oil.

The crude 15 was dissolved in IPA (4 L). The solution was treated with HCl/IPA solution (4.4 mol/L, 1.1 L) at RT. A large amount of solid was precipitated during the addition. The resulting suspension was stirred for 2 hrs. The solid product was collected by vacuum filtration and rinsed with MTBE (800 mL). 819 g of pure 15 was obtained as a white solid. The yield was 88.4%. $^1H$-NMR (300 MHz, $CD_3OD$) 4.20 (s, 2H), 3.88 (s, 3H), 2.30-2.40 (d, J=12 Hz, 2H), 1.95-2.02 (d, J=12 Hz, 2H), 1.55-1.85 (m, 5H), 1.20-1.40 (m, 1H).

Preparation of Compound 16:

To a solution of 15 (10 g, 43 mmol) in MeOH (100 mL) was added methanolic hydrochloride solution (2.44 mol/L, 35.3 mL, 2 eq) and $PtO2$ (0.5 g, 5 wt %). The reaction suspension was stirred with hydrogen bubble at 40° C. for 6 hours. H-NMR analysis showed consumption of 15. To the reaction mixture was added $K_2CO_3$ (15 g, 108 mmol, 2.5 eq) and the mixture was stirred for 3 hrs. The suspension was filtered and the filtrate was concentrated to dryness. The residual oil was diluted with DCM (100 mL) and resulting suspension was stirred for 3 hrs. After filtration, the filtrate was concentrated to provide crude 16 (6.6 g) as an oil. The crude 16 was diluted with EtOAc/hexane (1:1, 18 mL) at rt for 2 hrs. After filtration, 16 (4 g) was isolated. The obtained 16 was dissolved in DCM (16.7 mL) and hexane (100 mL) was added dropwise to precipitate the product. After further stirred for 1 h, 2.8 g of the pure 16 was isolated as a white solid. The yield was 39%. HPLC purity was 98.3%; MS (ESI): 169.2 (MH+); 1H-NMR (300 MHz, $D_2O$) 3.23 (s, 3H), 3.07 (s, 3H), 1.37-1.49 (m, 10H).

Preparation of Compound 19:

5-(4-methylpiperazin-1-yl)pyridin-2-amine (803.1 g; 3.0 equivalents based on sulfone 11) was charged to a 22 L flask. The flask was blanketed with $N_2$ and anhydrous THF added (12.4 kg). The resulting black-purple solution was cooled in an ice bath to <5° C. 1M LiHMDS (4.7 L; 1.2 equivalents based on sulfone 11) was added via an addition funnel in three equal additions to keep the temperature below 10° C. Upon the completion of the addition, the reaction mixture was warmed to 16° C. The sulfone 11 (455.1 g; 1.00 equivalents) was added in five additions. Reaction proceeded until HPLC analysis of an IPC sample indicated less than 3% of sulfone 11 remained. To quench the reaction, the contents of the 22 L flask were transferred to a 100 L flask containing water. After stirring for 30 minutes at <30° C., the crude product was collected by filtration, washed with water and dried to afford 19 (387 g, 99.1% purity, 63.7% yield).

Preparation of Compound 20:

5-(4-isopropylpiperazin-1-yl)pyridin-2-amine (1976.2 g; 3.0 equivalents based on sulfone 11) was charged to a 50 L flask. The flask was blanketed with $N_2$ and anhydrous THF added (10.7 kg). The resulting black-purple solution was cooled in an ice bath to <5° C. 1M LiHMDS (9.6 kg; 3.6 equivalents based on sulfone) was added via an addition funnel at a rate to keep the temperature below 10° C. Upon the completion of the addition, the reaction mixture was warmed to 16° C. over 120 minutes by removing the ice bath. The sulfone (1000 g; 1.00 mol) was added in five additions. The reaction proceeded until HPLC analysis of an IPC sample indicated less than 1% of sulfone 11 remained. After completion of the reaction, ammonium chloride was added to the reaction mixture. The mixture stirred at <32° C. for at least 30 minutes and the solids collected by filtration to afford 20 (900 g, 99.1% purity, 64.2% yield).

Alternate Route to Spirolactam Via Cyclohexanone:

Scheme 2-7

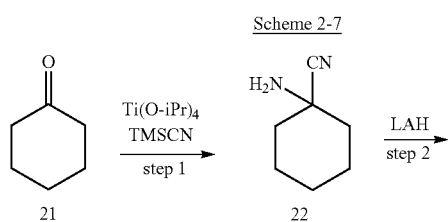

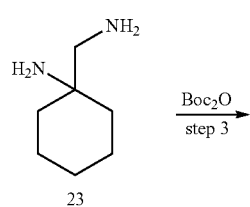

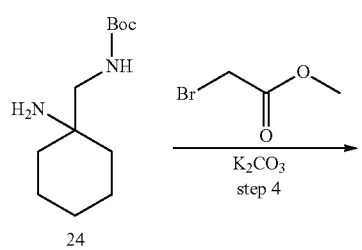

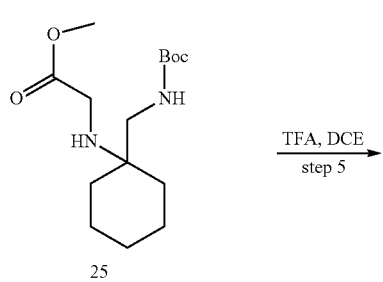

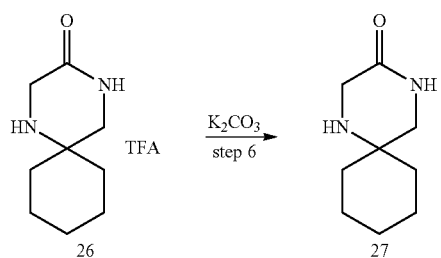

In one embodiment the spirolactam is made via the synthetic scheme above. By reducing the nitrile group before addition of the glycinate group the reaction sequence proceeds in higher yield. The chemistry used in Step 1 is described in the literature (*J. Org. Chem.* 2005, 70,8027-8034), and was performed on a kilogram scale. The chemistry to convert Compound 24 into the spirolactam was also demonstrated on kilogram scale. The Boc protection of Compound 23, is carried out at −70° C. in order to limit formation of the di-Boc protected product. Experimental details of a 200 g pilot run are described below.

Step 1

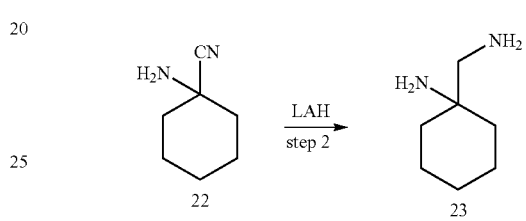

200 g of cyclohexanone 21 was converted to 22 using Ti(Oi-Pr)$_4$/TMSCN/NH3. After work-up, 213 g of 22 was obtained. The H-NMR was clean. The yield was 84%. The titanium salts were removed by vacuum filtration. In one embodiment, the titanium salts are removed by centrifugation or Celite filtration.

Step 2

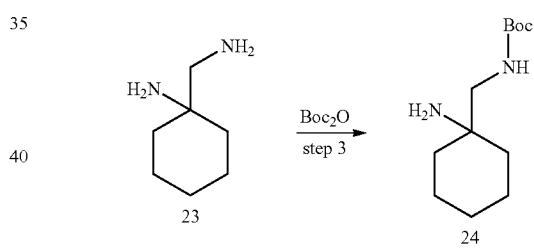

190 g of 22 was mixed with LAH (2 eq) in MTBE for 30 minutes at 45° C. After work-up, 148 g of crude 23 was obtained.

Step 3

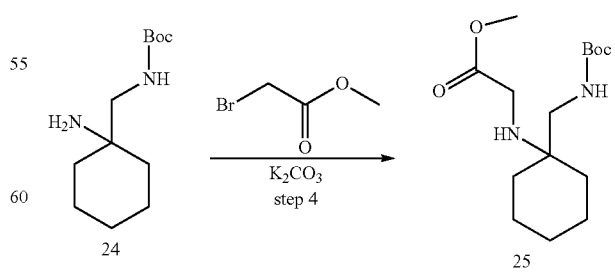

136 g of the crude 23 from step 2 was converted to 24 with 0.9 eq of Boc$_2$O at −70° C. The reaction was completed and worked up. After concentration, 188 g of 24 was obtained. The yield was 86%. The H-NMR and C-NMR spectra confirmed that the compound was pure.

Step 4

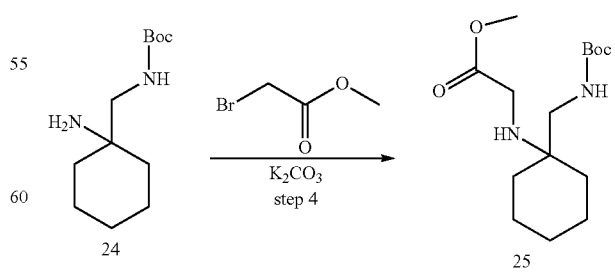

188 g of 24 was subjected to methyl 2-bromoacetate and K$_2$CO$_3$ in acetonitrile to afford 25. 247 g of crude 25 was obtained.

Step 5

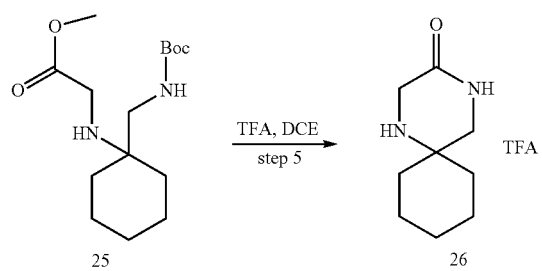 [SMILES: COC(=O)CNC1(CNC(=O)OC(C)(C)C)CCCCC1 ; O=C1CNC2(CCCCC2)CN1]

247 g of 25 was subjected to TFA in DCE heated to reflux to afford 26. After work-up, 112 g of 6 as TFA salt was obtained. H-NMR was clean.

Step 6

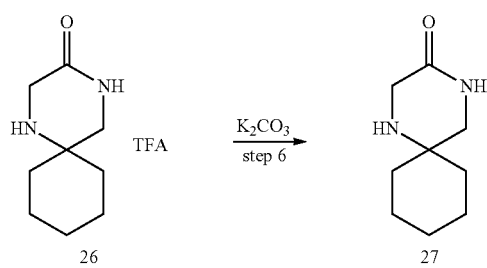 [SMILES: O=C1CNC2(CCCCC2)CN1 ; "K2CO3" ; O=C1CNC2(CCCCC2)CN1]

Compound 26 was stirred in EtOH in the presence at room temperature overnight to afford 27. In one embodiment DCM is used as the solvent instead of EtOH.

Example 3. Purge of Residual Palladium from Step 5 Scheme 2-1

Figure 3:
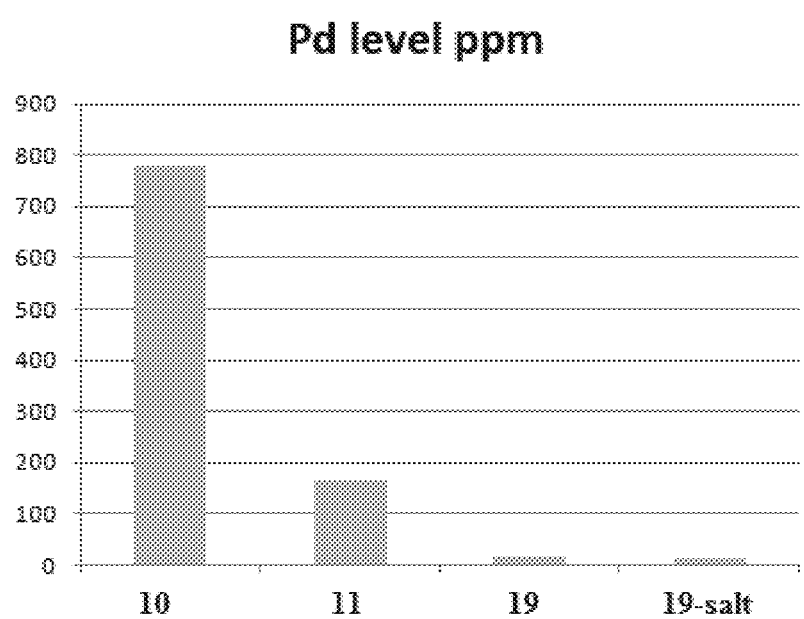
FIG. 3 illustrates the progressive decrease of Palladium levels measured in parts per million from compound 10 to 11 to 19 to the salt of 19. The final concentration of palladium is 1.47%. See example 3.
Figure 4:
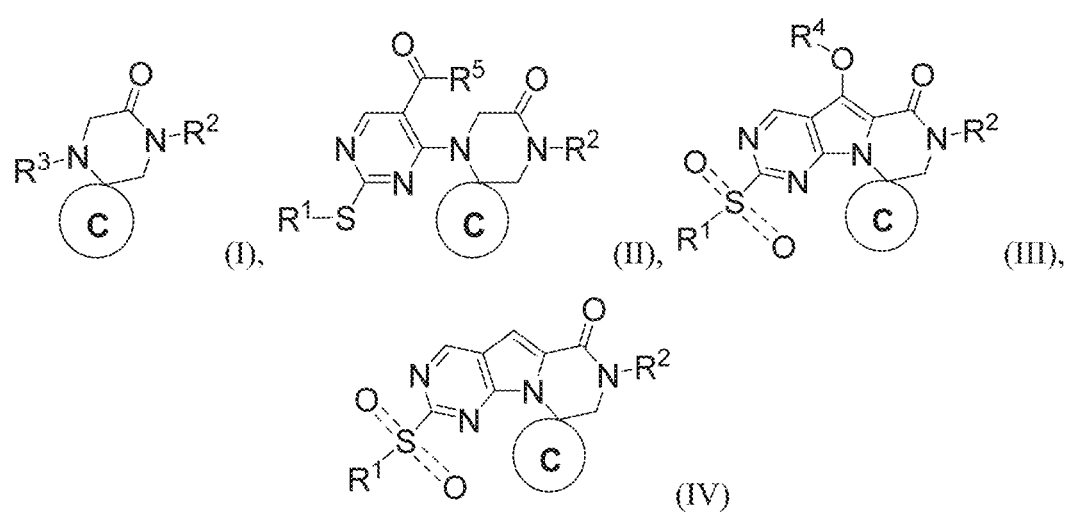
FIG. 4 is Formula I, Formula II, Formula III, and Formula IV.

Since palladium was used in Step 5 of Scheme 2-1, the levels of residual Pd present in the subsequent synthetic steps was determined. Table 2 below and FIG. 3 show the palladium levels in the isolated solids.

TABLE 2

| Step   | Step 5 | Step 6 | Step 7 | 19 FB | 19 Salt |
|--------|--------|--------|--------|-------|---------|
| Pd ppm | 14700  | 779    | 164    | 19    | 14      |

The material after Step 5 was isolated containing 1.47% (14700 ppm) of residual palladium. This data represents the highest level of palladium in the worst case scenario. The workup conditions of the latter steps purged nearly all of the palladium and the final product, 19 bis HCl salt, contained 14 ppm of Pd, which is below the standard 20 ppm guideline. The Pd levels will likely be even lower once the catalyst loading is optimized in Step 5.

19

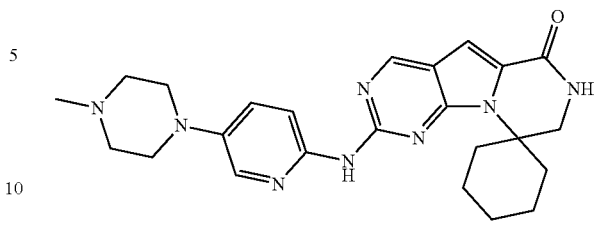

The process developed in this route was a significant improvement over the one used for the first generation synthesis. Overall, the scheme consists of seven steps with five isolations, all by crystallization. No silica column chromatography is employed in the synthesis, which makes the process highly scalable. The process workup conditions can successfully purge the 1.47% of residual palladium after step 5 of Scheme 2-1.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A compound of Formula II:

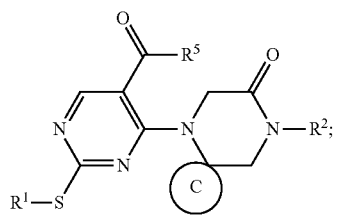

(II)

wherein:

represents a carbocycle of 3 to 8 carbons connected in a spiro-fashion to the lactam ring;

$R^1$ is selected from alkyl, aryl, haloalkyl, and arylalkyl;

$R^2$ is selected from hydrogen, carbamate, aryl, alkyl, allyl, and arylalkyl; and $R^5$ is selected from hydrogen, halogen, —N(alkyl)(alkoxy), —NCH$_3$OMe, alkoxy, aryloxy, —OCH$_2$aryl, —OC(O)alkyl, —OC(O)aryl, and —OC(O)arylalkyl.

2. The compound of claim 1 selected from:
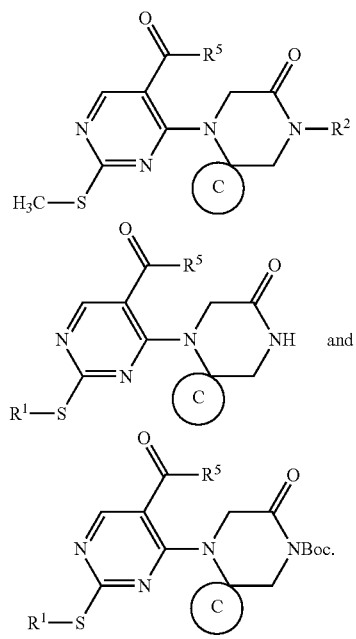
3. The compound of claim 1 selected from:
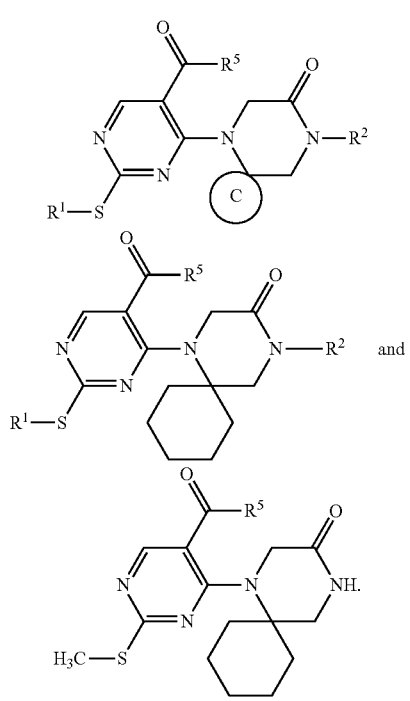
4. The compound of claim 1 selected from:
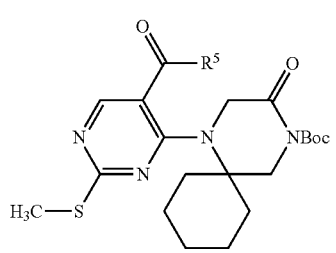
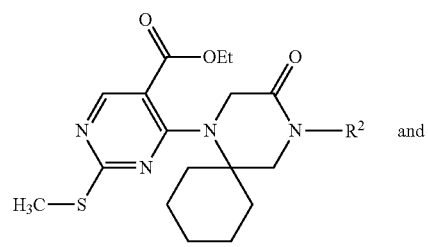
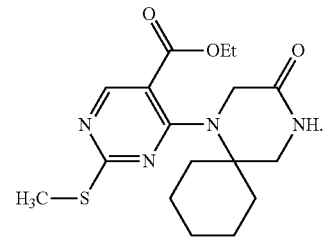
5. The compound of claim 1 selected from:
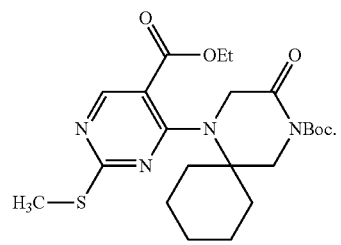 [SMILES: CCOC(=O)c1cnc(SC)nc1N1CC(=O)N(C(=O)OC(C)(C)C)CC12CCCCC2]
* * * * *